(12) United States Patent
Shuler

(10) Patent No.: US 10,149,930 B2
(45) Date of Patent: Dec. 11, 2018

(54) METHODS AND DRESSING SYSTEMS FOR PROMOTING HEALING OF INJURED TISSUE

(71) Applicant: Michael Simms Shuler, Athens, GA (US)

(72) Inventor: Michael Simms Shuler, Athens, GA (US)

(73) Assignee: J&M SHULER, INC., Athens, GA (US)

( * ) Notice: Subject to any disclaimer, the term of this patent is extended or adjusted under 35 U.S.C. 154(b) by 775 days.

(21) Appl. No.: 13/867,100

(22) Filed: Apr. 21, 2013

(65) Prior Publication Data

US 2014/0018752 A1 Jan. 16, 2014
US 2016/0346445 A9 Dec. 1, 2016

Related U.S. Application Data

(63) Continuation of application No. 12/855,019, filed on Aug. 12, 2010, now Pat. No. 8,447,375.
(Continued)

(51) Int. Cl.
*A61M 1/00* (2006.01)
*A61B 5/145* (2006.01)
(Continued)

(52) U.S. Cl.
CPC ....... *A61M 1/0088* (2013.01); *A61B 5/14539* (2013.01); *A61B 5/445* (2013.01);
(Continued)

(58) Field of Classification Search
CPC ............ A61M 1/0088; A61M 2205/18; A61M 2205/3313; A61M 2205/3344;
(Continued)

(56) References Cited

U.S. PATENT DOCUMENTS 4,460,354 A 7/1984 Weilbacher et al.
4,559,035 A 12/1985 Benjamin et al.
(Continued)

FOREIGN PATENT DOCUMENTS

EP 1304966 5/2003
WO WO 1997/005838 2/1997
(Continued)

OTHER PUBLICATIONS

European Search Report for EP App. No. 10822386.8, dated Jul. 22, 2014, 7 pages.
(Continued)

*Primary Examiner* — Andrew J Mensh
(74) *Attorney, Agent, or Firm* — Fish & Richardson P.C.

(57) ABSTRACT

A dressing system is disclosed which has a sponge and a near infrared spectroscopy sensor positioned adjacent to the sponge for monitoring oxygenation levels of tissue adjacent to the sponge. The dressing system may further include a tube coupled to the sponge for removing fluid from the sponge. The dressing system comprises: a sponge; and a tensioning system coupled to the sponge. The tensioning system further comprises a central longitudinal member coupled to the sponge; and at least one tensioning member coupled to the central longitudinal member. A sequential compression system comprises: an envelope sleeve dressing; and a bladder that is both expandable and retractable. A tissue filler system is also described and includes a plurality of tubes; wherein each of the plurality of tubes further comprises apertures; and a pump coupled to at least one of the tubes which obviates the need for any sponge or wound screen.

19 Claims, 34 Drawing Sheets

Related U.S. Application Data

(60) Provisional application No. 61/233,797, filed on Aug. 13, 2009, provisional application No. 61/234,857, filed on Aug. 18, 2009, provisional application No. 61/245,789, filed on Sep. 25, 2009.

(51) Int. Cl.
- *A61F 13/00* (2006.01)
- *A61B 5/00* (2006.01)
- *A61B 5/01* (2006.01)
- *A61B 5/1455* (2006.01)

(52) U.S. Cl.
CPC .. *A61F 13/00055* (2013.01); *A61F 13/00068* (2013.01); *A61B 5/0059* (2013.01); *A61B 5/01* (2013.01); *A61B 5/14552* (2013.01); *A61M 2205/18* (2013.01); *A61M 2205/3313* (2013.01); *A61M 2205/3344* (2013.01)

(58) Field of Classification Search
CPC ... A61B 5/14539; A61B 5/445; A61B 5/0059; A61B 5/01; A61B 5/14552; A61F 13/00055; A61F 13/00068
USPC ........................................................ 604/540
See application file for complete search history.

(56) References Cited

U.S. PATENT DOCUMENTS

| | | | |
|---|---|---|---|
| 4,886,502 | A | 12/1989 | Poirier et al. |
| 4,969,880 | A * | 11/1990 | Zamierowski .... A61F 13/00068 604/180 |
| 5,071,409 | A | 12/1991 | Rosenberg |
| 5,100,396 | A | 3/1992 | Zamierowski |
| 5,176,663 | A | 1/1993 | Svedman et al. |
| 5,261,893 | A | 11/1993 | Zamierowski |
| 5,358,494 | A | 10/1994 | Svedman |
| 5,527,293 | A | 6/1996 | Zamierowski |
| 5,549,584 | A | 8/1996 | Gross |
| 5,636,643 | A | 6/1997 | Argenta et al. |
| 5,645,081 | A | 7/1997 | Argenta et al. |
| 5,678,564 | A | 10/1997 | Lawrence et al. |
| 5,755,706 | A | 5/1998 | Kronenthal et al. |
| 5,911,222 | A | 6/1999 | Lawrence et al. |
| 6,045,541 | A | 4/2000 | Matsumoto et al. |
| 6,048,337 | A | 4/2000 | Svedman |
| 6,071,267 | A | 6/2000 | Zamierowski |
| 6,142,982 | A | 11/2000 | Hunt et al. |
| 6,176,868 | B1 | 1/2001 | Detour |
| 6,345,623 | B1 | 2/2002 | Heaton et al. |
| 6,458,109 | B1 | 10/2002 | Henley et al. |
| 6,468,237 | B1 | 10/2002 | Lina |
| 6,685,681 | B2 | 2/2004 | Anker et al. |
| 6,695,823 | B1 | 2/2004 | Lina et al. |
| 6,752,794 | B2 | 6/2004 | Lockwood et al. |
| 6,764,462 | B2 | 7/2004 | Risk, Jr. et al. |
| 6,767,334 | B1 | 7/2004 | Randolph |
| 7,004,915 | B2 | 2/2006 | Boynton et al. |
| 7,022,113 | B2 | 4/2006 | Lockwood et al. |
| 7,108,683 | B2 | 9/2006 | Zamierowski |
| 7,117,869 | B2 | 10/2006 | Heaton et al. |
| 7,276,051 | B1 | 10/2007 | Henley et al. |
| 7,338,482 | B2 | 3/2008 | Lockwood et al. |
| 7,361,184 | B2 | 4/2008 | Joshi |
| 7,413,571 | B2 | 8/2008 | Zamierowski |
| 7,438,705 | B2 | 10/2008 | Karpowicz et al. |
| 7,520,872 | B2 | 4/2009 | Biggie et al. |
| 7,524,286 | B2 | 4/2009 | Johnson |
| 7,524,315 | B2 | 4/2009 | Blott et al. |
| 7,532,953 | B2 | 5/2009 | Vogel |
| 7,534,927 | B2 | 5/2009 | Lockwood et al. |
| 7,608,066 | B2 | 10/2009 | Vogel |
| 7,651,484 | B2 | 1/2010 | Heaton et al. |
| 7,723,560 | B2 | 5/2010 | Lockwood et al. |
| 7,837,673 | B2 | 11/2010 | Vogel |
| 7,867,206 | B2 | 1/2011 | Lockwood et al. |
| 7,883,494 | B2 | 2/2011 | Martin |
| 7,922,703 | B2 | 4/2011 | Riesinger |
| 7,927,318 | B2 | 4/2011 | Risk, Jr. et al. |
| 7,951,100 | B2 | 5/2011 | Hunt et al. |
| 7,967,810 | B2 | 6/2011 | Freedman |
| 7,988,680 | B2 | 8/2011 | Lockwood et al. |
| 8,057,446 | B2 | 11/2011 | Kane et al. |
| 8,066,243 | B2 | 11/2011 | Svedman et al. |
| 8,142,405 | B2 | 3/2012 | Vogel |
| 8,162,909 | B2 | 4/2012 | Blott et al. |
| 8,187,210 | B2 | 5/2012 | Hunt et al. |
| 8,350,116 | B2 | 1/2013 | Lockwood et al. |
| 8,372,049 | B2 | 2/2013 | Jaeb et al. |
| 8,376,972 | B2 | 2/2013 | Fleischmann |
| 8,425,478 | B2 | 4/2013 | Olson |
| 8,444,613 | B2 | 5/2013 | Svedman et al. |
| 8,447,375 | B2 | 5/2013 | Freedman et al. |
| 8,460,258 | B2 | 6/2013 | Jones et al. |
| 8,460,273 | B2 | 6/2013 | Freedman et al. |
| 2001/0031943 | A1 | 10/2001 | Urie |
| 2002/0065494 | A1* | 5/2002 | Lockwood .......... A61M 1/0058 604/313 |
| 2002/0115967 | A1 | 8/2002 | Svedman |
| 2002/0143286 | A1 | 10/2002 | Tumey |
| 2002/0150720 | A1* | 10/2002 | Howard ................. A61F 13/02 428/131 |
| 2002/0183702 | A1 | 12/2002 | Henley |
| 2003/0050594 | A1* | 3/2003 | Zamierowski ...... A61M 1/0058 604/46 |
| 2003/0139255 | A1 | 7/2003 | Lina |
| 2003/0163160 | A1 | 8/2003 | O'Malley et al. |
| 2003/0208149 | A1 | 11/2003 | Coffey |
| 2004/0006319 | A1 | 1/2004 | Lina et al. |
| 2004/0054338 | A1 | 3/2004 | Bybordi et al. |
| 2004/0064111 | A1 | 4/2004 | Lockwood et al. |
| 2004/0064132 | A1 | 4/2004 | Boehringer et al. |
| 2004/0265040 | A1 | 12/2004 | Rosenberg |
| 2005/0070858 | A1 | 3/2005 | Lockwood et al. |
| 2005/0085795 | A1* | 4/2005 | Lockwood .............. A61F 13/02 604/543 |
| 2006/0041238 | A1 | 2/2006 | Bowen |
| 2006/0065494 | A1 | 3/2006 | Kim |
| 2006/0129137 | A1 | 6/2006 | Lockwood et al. |
| 2006/0155260 | A1* | 7/2006 | Blott .................... A61M 1/0001 604/543 |
| 2006/0282028 | A1 | 12/2006 | Howard et al. |
| 2007/0038247 | A1 | 2/2007 | Lebner et al. |
| 2007/0167926 | A1 | 7/2007 | Blott et al. |
| 2007/0225634 | A1 | 9/2007 | Ferren et al. |
| 2007/0225663 | A1* | 9/2007 | Watt ....................... A61F 13/02 604/313 |
| 2008/0167593 | A1 | 7/2008 | Fleischmann |
| 2008/0208011 | A1 | 8/2008 | Shuler |
| 2009/0177051 | A1* | 7/2009 | Arons .................. A61B 5/0059 600/306 |
| 2009/0221977 | A1 | 9/2009 | Blott et al. |
| 2010/0191196 | A1 | 7/2010 | Heagle |
| 2010/0191198 | A1 | 7/2010 | Heagle |
| 2010/0262091 | A1 | 10/2010 | Larsson |
| 2010/0280428 | A1 | 11/2010 | Widgerow et al. |
| 2010/0292549 | A1 | 11/2010 | Shuler |
| 2011/0034888 | A1 | 2/2011 | Aali |
| 2011/0054283 | A1 | 3/2011 | Shuler |
| 2011/0106026 | A1 | 5/2011 | Wu et al. |
| 2011/0125110 | A1 | 5/2011 | Cotton |
| 2011/0172617 | A1 | 7/2011 | Riesinger |
| 2011/0213319 | A1 | 9/2011 | Blott et al. |
| 2012/0041403 | A1 | 2/2012 | Bennett et al. |
| 2012/0316518 | A1 | 12/2012 | Croizt et al. |
| 2013/0096520 | A1 | 4/2013 | Lockwood et al. |
| 2013/0138060 | A1 | 5/2013 | Haggstrom et al. |
| 2013/0144230 | A1 | 6/2013 | Wu et al. |
| 2013/0165821 | A1 | 6/2013 | Freedman et al. |
| 2013/0165878 | A1 | 6/2013 | Heagle |

(56) References Cited

U.S. PATENT DOCUMENTS

| | | |
|---|---|---|
| 2013/0172834 A1 | 7/2013 | Heagle |
| 2013/0274695 A1 | 10/2013 | Freedman et al. |

FOREIGN PATENT DOCUMENTS

| | | |
|---|---|---|
| WO | WO 2007/041642 | 4/2007 |
| WO | WO 2008/100440 | 8/2008 |
| WO | WO 2009/062327 | 5/2009 |
| WO | WO 2009/093116 | 7/2009 |
| WO | WO 2011/091045 | 7/2011 |

OTHER PUBLICATIONS

International Preliminary Report on Patentability for PCT/US2010/045262, dated Feb. 14, 2012, 6 pages.
International Search Report and Written Opinion for PCT/US2010/045262, dated Jun. 17, 2011, 7 pages.
U.S. Appl. No. 60/853,000, filed Oct. 20, 2006, Freedman.
U.S. Appl. No. 61/643,840, filed May 7, 2012, Freedman.
U.S. Appl. No. 61/554,080, filed Nov. 1, 2011, Freedman.
U.S. Appl. No. 13/843,507, filed Mar. 15, 2013, Freedman.
Argenta et al., "Vacuum-Assisted Closure: A New Method For Wound Control And Treatment: Clinical Experience," *Annals of Plastic Surgery*, 1997, 38(6): 563-577.
Argenta et al., "Vacuum-Assisted Closure: A New Method For Wound Control And Treatment: Basic Foundation," *Annals Of Plastic Surgery*, 1997, 38(6): 553-562.
Brock et al., "Temporary Closure of Open Abdominal Wounds: The Vacuum Pack," *Am Surg.*, 1995, 61(1): 30-35.
Buckman, "Vacuum Assisted Wound Closure System," *Drexel University white paper*, Jul. 15, 2006.
Davydov et al., "Concepts for Clinical Biological Management of the Wound Process in the Treatment of Purulent Wounds Using Vacuum Therapy," *The Kremlin Papers; Perspectives in Wound Care from the Russian Medical Journal*, 1991, 132-135.
Davydov et al., "The Bacteriological and Cytological Assessment of Vacuum Therapy of Purulent Wounds," *The Kremlin papers, Perspectives in Wound Care from the Russian Medical Journal*, 1988, 48-52.
Davydov et al., "Vacuum Therapy in the Treatment of Purulent lactation Mastitis," *The Kremlin papers, perspectives in Wound Care from the Russian Medical Journal*, 1986, 66-70.
Kostiuchenok et al., "The Vacuum Effect in the Surgical Treatment of Purulent Wounds," *The Kremlin Papers, Perspectives in Wound Care from the Russian Medical* Journal, 1986, 18-21.
Scherer et al., "The vacuum assisted closure device: A method for securing skin grafts and improving graft survival," *Arch Surg.*, 2002, 137(8): 930-933.
Singh et al., "Dynamic Wound Closure for Decompressive Leg Fasciotomy Wounds," *Am Surg*, 2008, 74(3): 217-220.
Usupov et al., "Active Wound Drainage," *The Kremlin Papers, Perspectives in Wound Care from the Russian Medical Journal*, 1987, 42-45.
Valenta, "Using the Vacuum Dressing Alternative for Difficult Wounds," *American J. of Nursing*, 1994, 44-45.
Van der Velde and Hudson, "VADER (vacuum-assisted dermal recruitment: a new method of wound closure," *Annals of Plastic Surgery*, 2005, 55(6): 660-664.
Wackenfors, et al., "Effects of vacuum-assisted closure therapy on inguinal wound edge microvascular blood flow," *Wound Repaire and Regeneration*, 2004, 12(6): 600-606.
Webb, "New Techniques in Wound Management: Vacuum-assisted Wound Closure," *J. Am Acad Orthop Surg*, 2002, 10(5): 303-311.
Zannis et al, "Comparison of Fasciotomy Wound Closures Using Traditional Dressing Changes and the Vacuum-assisted Closure Device," *Annals of Plastic Surgery*, 2009, 62(4): 407-409.
Zorilla, et al, "Shoelace technique for gradual closure of fasciotomy wounds," *The Journal of Trama*, 2005, 59(6): 1515-1517.
Australian Office Action in Australian Application No. 2012332941, dated Jul. 13, 2016, 2 pages.
Canadian Office Action in Application No. 2,769,671, dated May 16, 2017, 4 pages.

\* cited by examiner

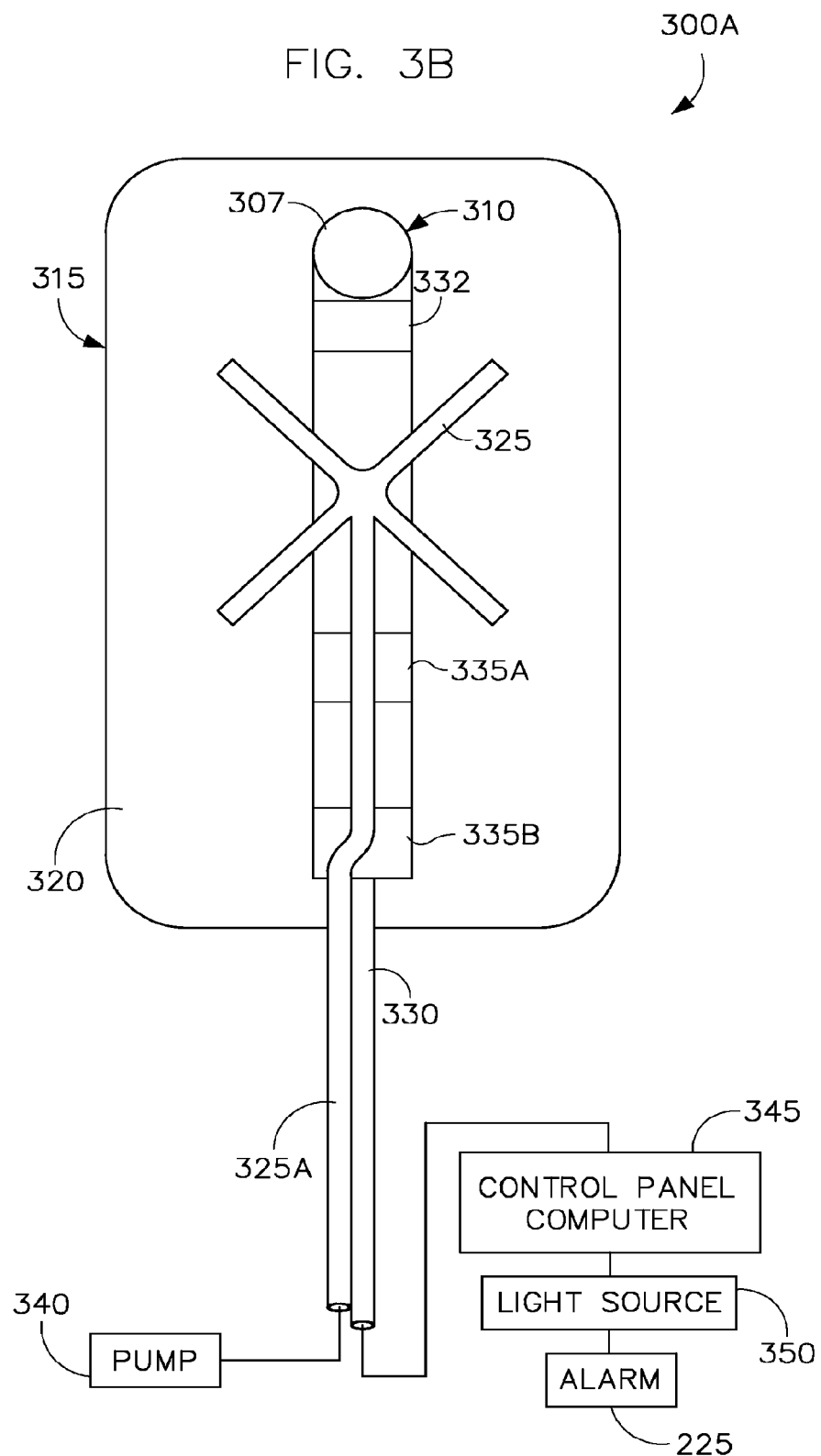

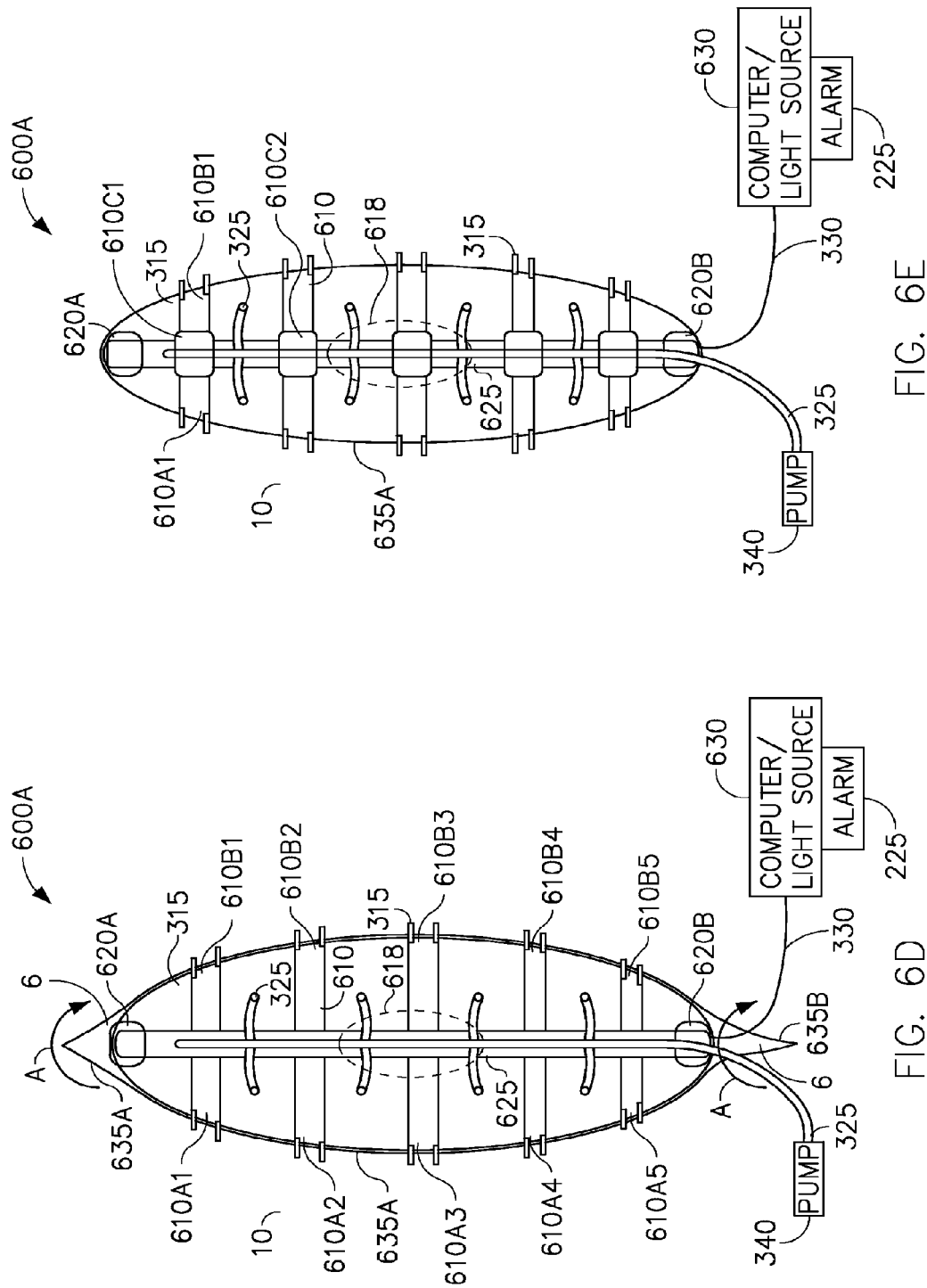

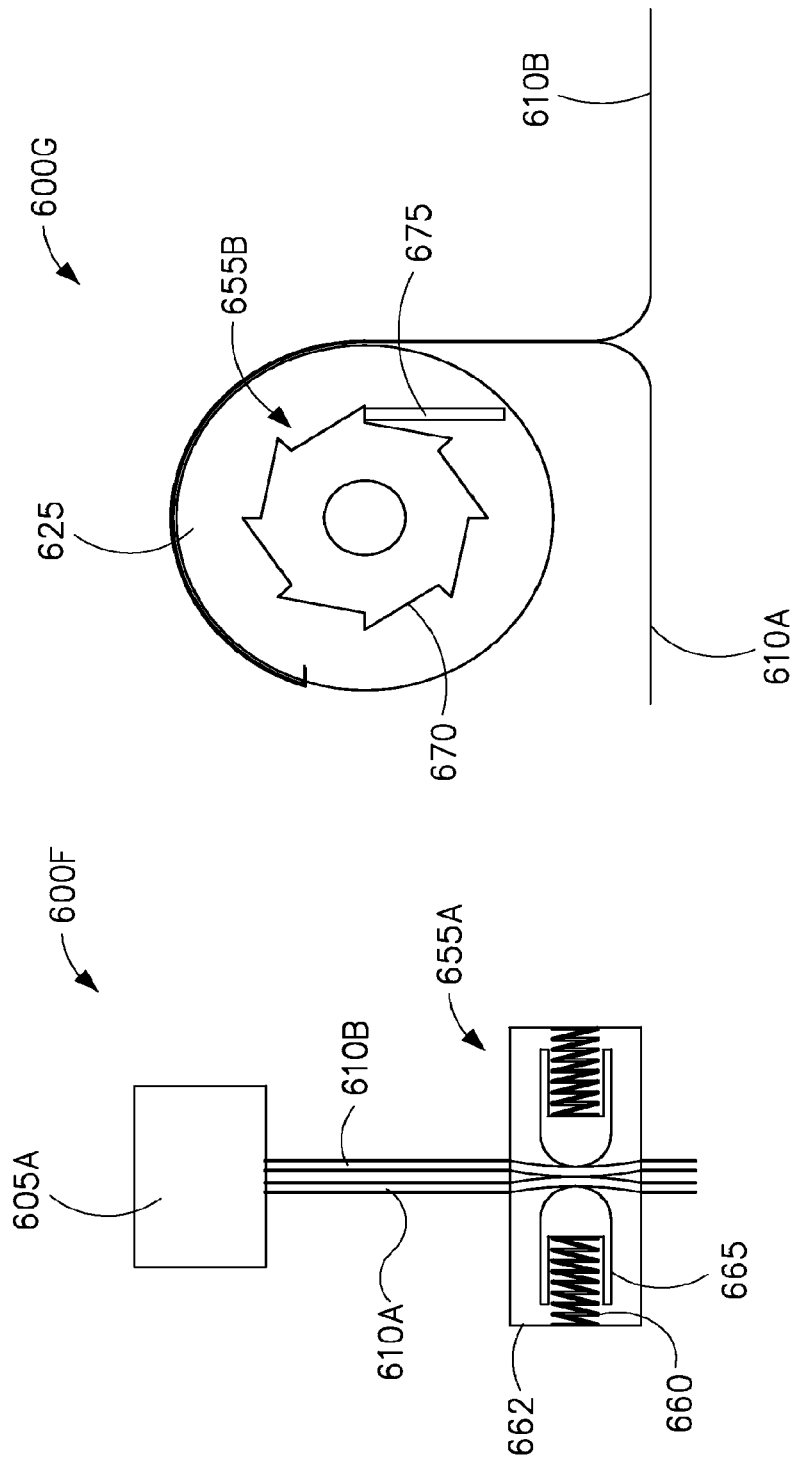

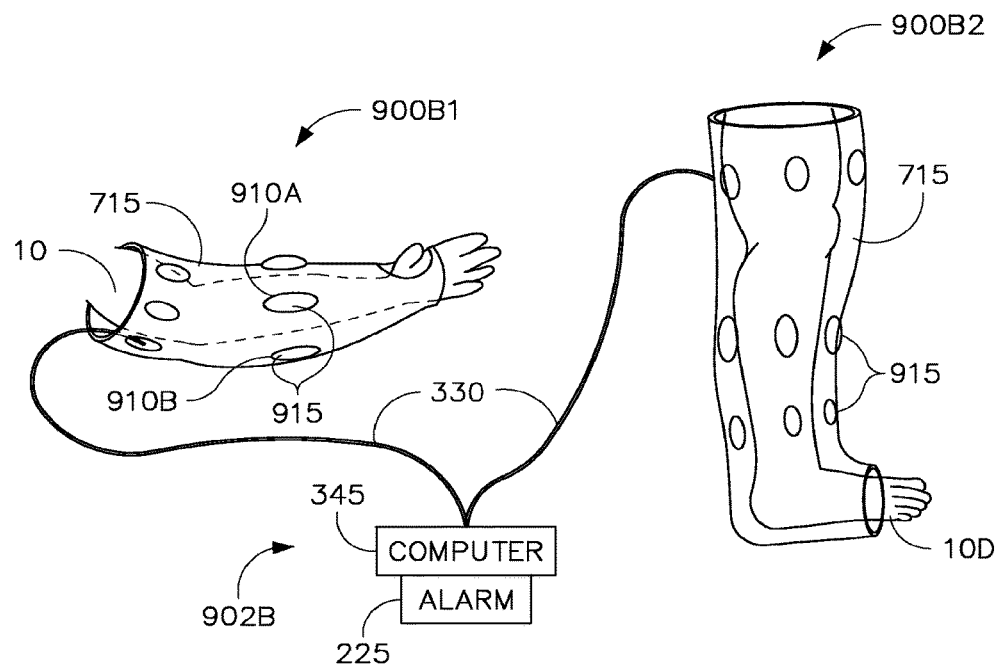
FIG. 9C
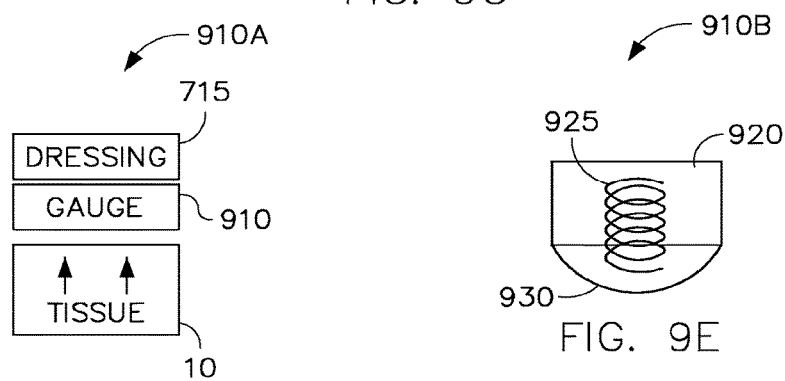
FIG. 9D
FIG. 9E
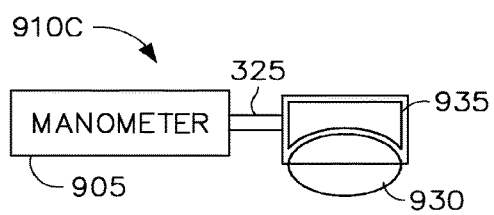
FIG. 9F
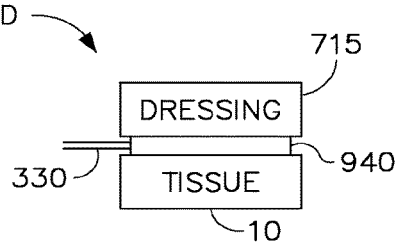
FIG. 9G

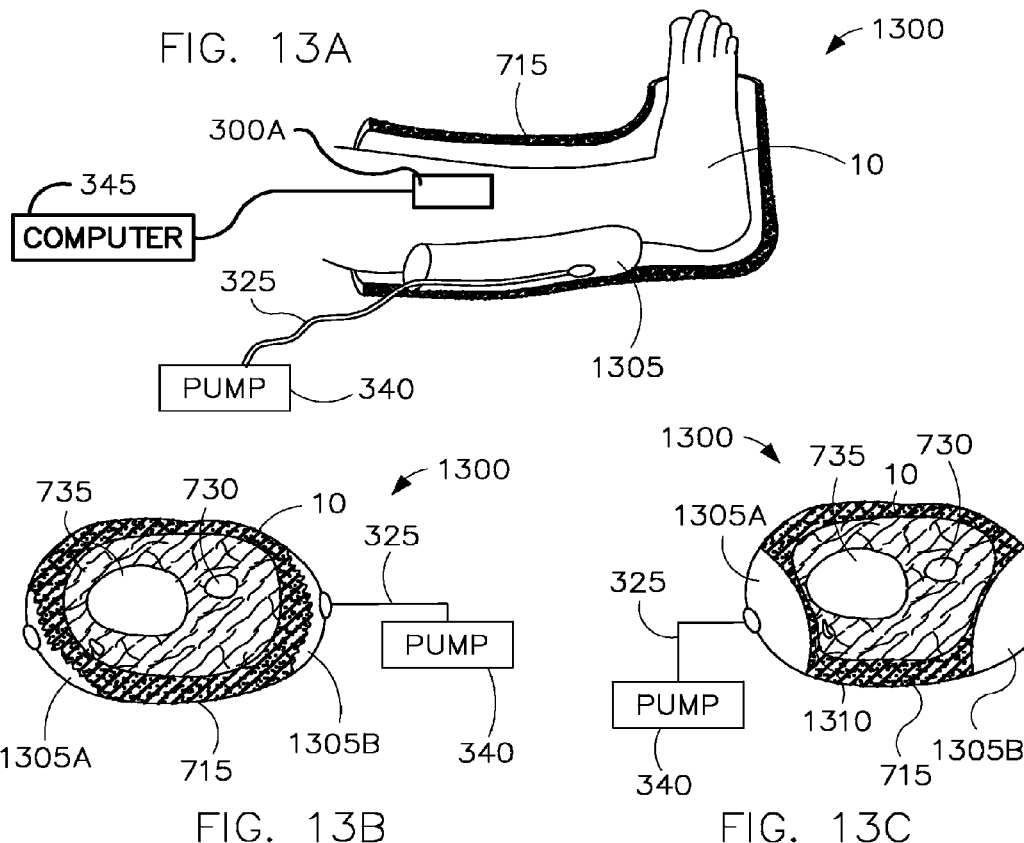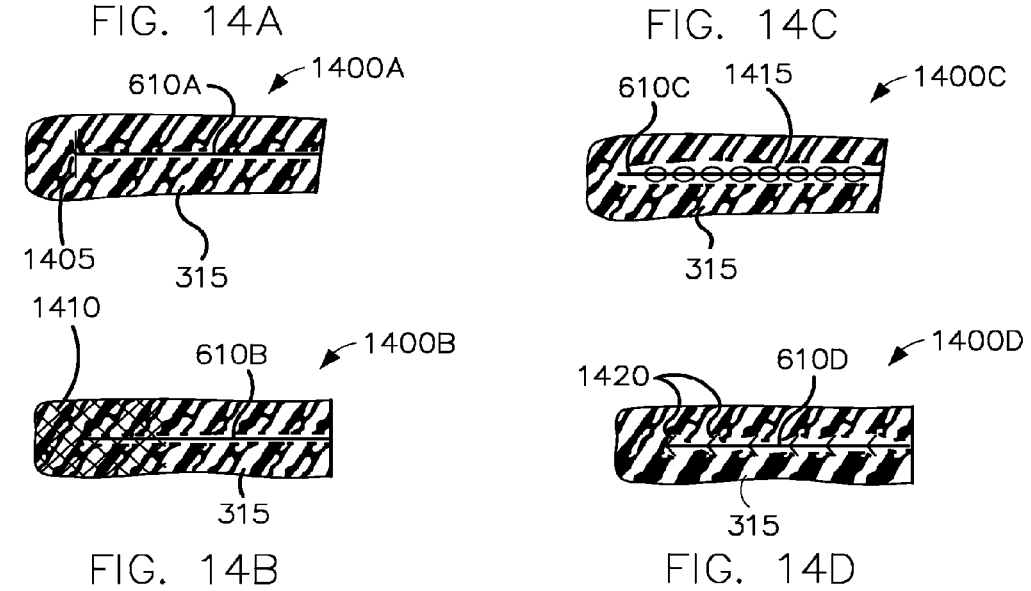

FIG. 15A
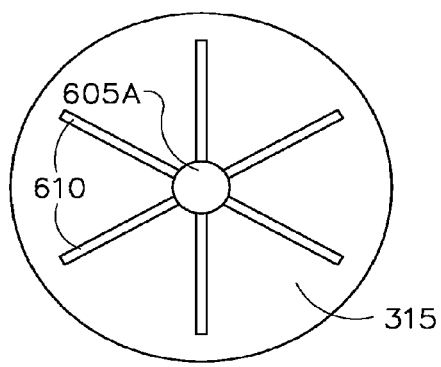
FIG. 15B
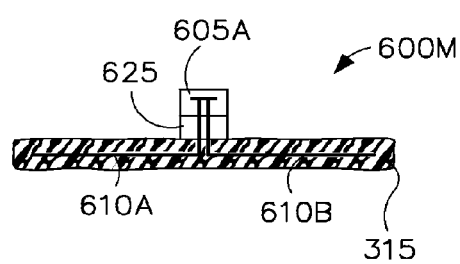
FIG. 15C
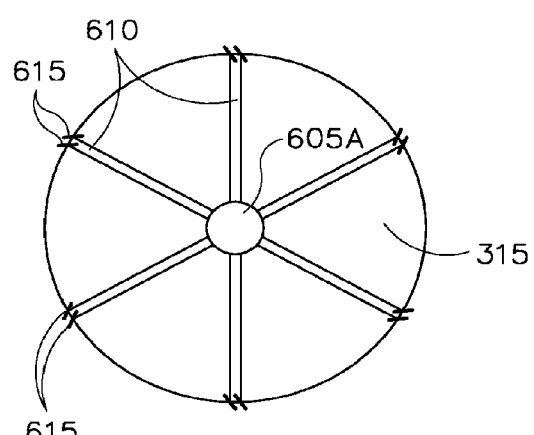
FIG. 15D
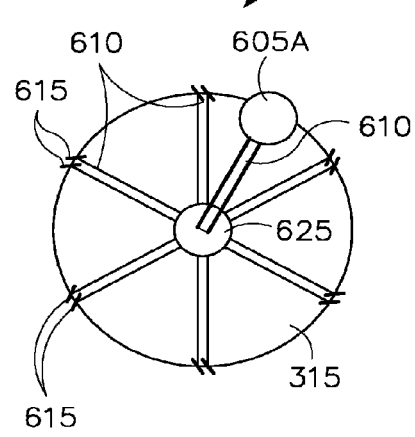
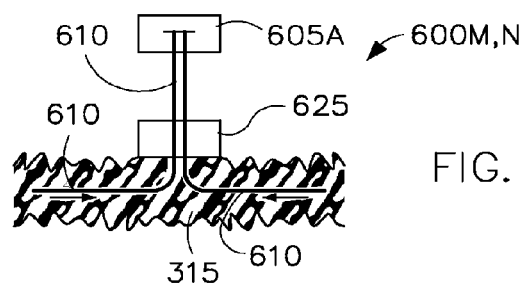
FIG. 15E

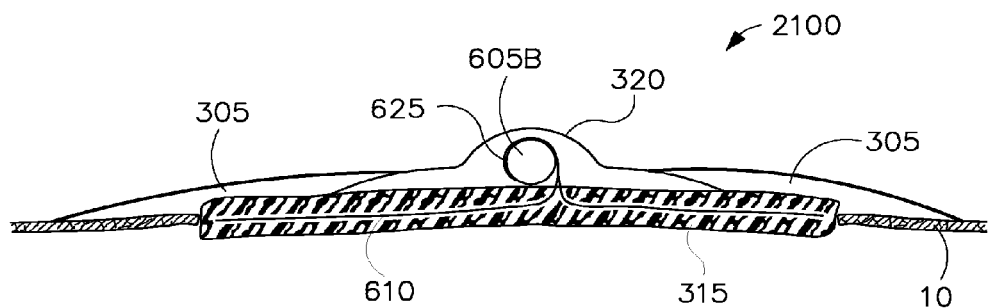
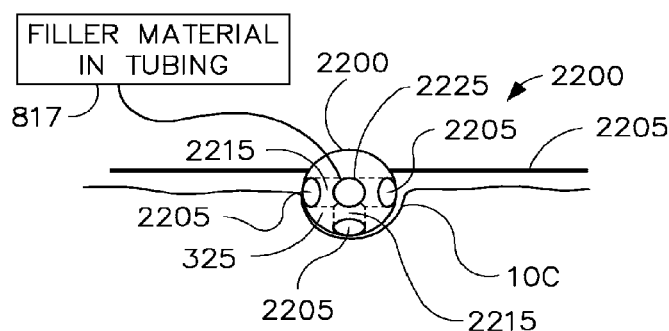
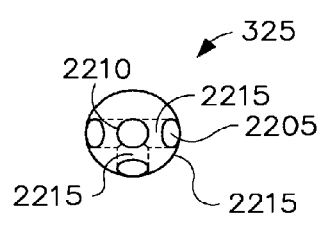
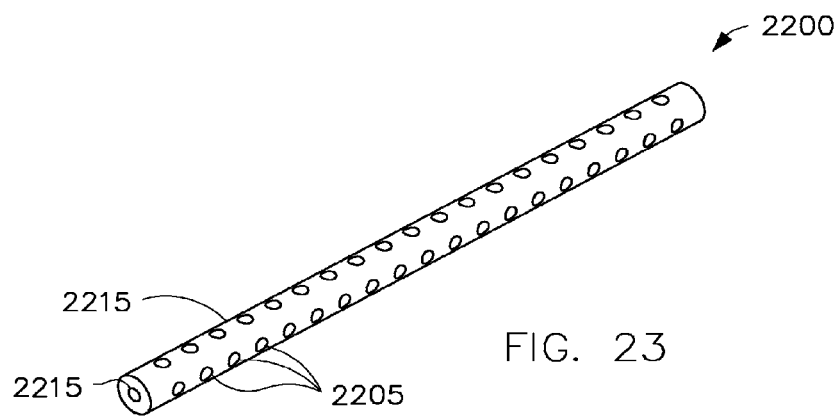

METHODS AND DRESSING SYSTEMS FOR PROMOTING HEALING OF INJURED TISSUE

STATEMENT REGARDING RELATED APPLICATIONS

This is a continuation of U.S. application Ser. No. 13/867,100, filed on Apr. 21, 2013, which claims priority under 35. U.S.C. § 119(e) to: (1) provisional patent application entitled, "Smart Dressing for Wounds or Injured Extremities," filed on Aug. 13, 2009 and assigned U.S. application Ser. No. 61/233,797; (2) provisional patent application entitled, "Smart Dressing for Wounds or Injured Extremities," filed on Aug. 18, 2009 and assigned U.S. application Ser. No. 61/234,857; and (3) provisional patent application entitled "Smart Dressing for Wounds or Injured Extremities," filed on Sep. 25, 2009 and assigned U.S. application Ser. No. 61/245,789. The contents of these aforementioned patent applications are hereby incorporated by reference in their entirety.

FIELD OF INVENTION

The invention generally relates to patient wound care, and more specifically to systems and methods for treating open wounds.

BACKGROUND

Animal tissue, such as human tissue, is susceptible to injury. Injuries that pierce, tear or cut tissue can be difficult to heal especially when the pierced, torn or cut tissue traverses a large area relative to the entire surface of the animal. Typical injuries which are difficult to heal include those from burns and traumatic injuries. Additionally, chronic diseases such as diabetes results in chronic wounds and tissue break down. Frequently, injured tissue may also be the result of intentional medical procedures, such as a fasciotomy.

A fasciotomy is a surgical procedure where the fascia is cut to relieve tension or pressure (and treat the resulting loss of circulation to an area of tissue or muscle). Complications related to this medical procedure usually involve the formation of scar tissue after the operation. Another challenge of this medical procedure is the ability to cover and/or close the tissue which is intentionally cut during the procedure.

Other medical procedures which are difficult to heal from include skin grafts used to cover open, wounded tissue. While skin grafts are intended to promote healing by covering an open wound, they are difficult to heal because of hematomas, fluid collection, and movement that can occur near or within the skin graft.

Over time as wounds heal, the edges of the skin retract. This retraction ultimately may cause the wound to become larger and more difficult to get closed. Larger wounds typically require more invasive measures to close such as skin graft or free flaps which include skin, soft tissue and typically a blood supply such as an artery and veins.

Conventional dressings, such as bolster dressings, that are frequently used to treat the injured tissue discussed above suffer from many problems and/or drawbacks. One problem is the ability to remove excess fluid build-up that can occur near and/or within the wounded tissue. When such fluid build-up occurs, this increases the chances for higher bacterial counts which in-turn causes infection in the wounded area of the patient. Additionally, hematomas can lift skin grafts off the underlying tissue bed and separate the graft from its blood and nutrient supply causing graft failure. Other problems include the ability to promote closing of the open wound while the wound heals.

What is needed in the art is a method and system that may promote the healing of wounds in tissue by removing excess fluid from wounds as well as applying appropriate forces to edges of a wound in order to bring the edges closer together for a complete closure of a wound, without the need of other medical procedures, such as skin grafts.

SUMMARY OF THE INVENTION

According to one exemplary aspect, a dressing system comprises: a sponge; a near infrared spectroscopy (NIRS) sensor positioned adjacent to the sponge for monitoring oxygenation levels of tissue adjacent to the sponge; and a tube coupled to the sponge for removing fluid from the sponge and applying a negative pressure gradient to the tissue.

According to another exemplary aspect, a dressing system comprises: a sponge; a tensioning system coupled to the sponge. The tensioning system further comprises a central longitudinal member coupled to the sponge; and at least one transverse tensioning member coupled to the central longitudinal member. This embodiment couples two strategies for would management, a negative pressure device to stimulate local blood flow and healing while reducing soft tissue swelling with a tensioning device to approximate the skin edges as soft tissue swelling reduces while preventing wound contracture. Additional monitoring technologies, such as, but not limited to, NIRS, pH, and temperature can be added to the device.

According to a further exemplary aspect, a sequential compression system comprises: an envelope sleeve dressing; and a bladder that is both expandable and retractable. This sequential compression system may transiently compress tissue to promote blood flow and return of blood to the heart in the venous system to prevent the stasis of blood. Hemostasis as well as endothelial injury are two of the three aspects of Virchow's triad (hypercoagulability, hemostasis and endothelial/blood vessel injury) which is known to promote clotting. By preventing hemostasis with sequential compression, one goal is to prevent deep vein thrombosis (DVT's) or clots (typically in the legs) which cause swelling and pain. Additionally, these DVT's can ultimately migrate towards the heart and cause clots in the lungs known as pulmonary embolism which can be fatal.

According to an additional exemplary aspect, a tissue filler system comprises: a plurality of tubes; each of the plurality of tubes further comprises apertures; and a pump coupled to at least one of the tubes. This tissue filler system may eliminate the need for a sponge all together while allowing for tensioning and negative pressure gradient. By removing the sponge, such a dressing may allow for longer applications without the need for frequent changes of the dressing due to tissue in-growth which are costly and painful to the patient. Additionally, the residue left behind by a sponge dressing can cause inflammatory reactions and is a risk for infection.

BRIEF DESCRIPTION OF THE DRAWINGS

In the Figures, like reference numerals refer to like parts throughout the various views unless otherwise indicated. For reference numerals with letter character designations such as "102A" or "102B", the letter character designations may differentiate two like parts or elements present in the same figure. Letter character designations for reference numerals may be omitted when it is intended that a reference numeral to encompass all parts having the same reference numeral in all Figures.

FIG. 3B is a diagram illustrating an elevation view of the dressing system comprising a wound-vacuum combined with a near infrared spectroscopy (NIRS) sensor of FIG. 3A according to one exemplary embodiment of the invention;

FIG. 6D is a diagram illustrating an elevation view of the dressing system without tension applied in full expansion of FIG. 6A according to one exemplary embodiment of the invention;

FIG. 6E is a diagram illustrating an elevation view of the dressing system of FIG. 6A in which tension forces have been exerted by the tensioning device causing the sponge to contract according to one exemplary embodiment of the invention;

FIG. 6R is a diagram illustrating a cross-sectional view of a dressing system with another type of locking mechanism for the end tensioning mechanism according to one exemplary embodiment of the invention;

FIG. 6S is a diagram illustrating a cross-sectional view of a dressing system with another type of locking mechanism according to one exemplary embodiment of the invention;

FIG. 9C is a diagram illustrating another pressure monitor and possible locations for the monitors for a dressing system according to one exemplary embodiment of the invention;

FIG. 9D is a diagram illustrating the environment for an exemplary pressure transducer according to one exemplary embodiment of the invention;

FIG. 9E is a diagram illustrating a pressure transducer for a pressure monitoring system according to one exemplary body of the invention;

FIG. 9F is a diagram illustrating another pressure transducer for a pressure monitoring system according to one exemplary embodiment of the invention;

FIG. 9G is a diagram illustrating another pressure transducer for a pressure monitoring system according to one exemplary embodiment of the invention;

FIG. 13A is a side view of a sequential compression dressing system according to one exemplary embodiment of the invention;

FIG. 13B is a cross-sectional view of the sequential compression dressing system of FIG. 13A in a deflated state according to one exemplary embodiment of the invention;

FIG. 13C is a cross-sectional view of the sequential compression dressing system of FIG. 13B in an inflated state according to one exemplary embodiment of the invention;

FIG. 14A is a diagram illustrating a cross-sectional view of a first anchoring mechanism for a tension member of a tensioning device according to one exemplary embodiment of the invention;

FIG. 14B is a diagram illustrating a cross-sectional view of a second anchoring mechanism for a tension member of a tensioning device according to one exemplary embodiment of the invention;

FIG. 14C is a diagram illustrating a cross-sectional view of a third anchoring mechanism for a tension member of a tensioning device according to one exemplary embodiment of the invention;

FIG. 14D is a diagram illustrating a cross-sectional view of a fourth anchoring mechanism for a tension member of a tensioning device according to one exemplary embodiment of the invention;

FIG. 15A is a diagram illustrating an elevation view of a dressing system with the tensioning device in a radial design for a circular wound according to one exemplary embodiment of the invention;

FIG. 15B is a diagram illustrating cross-sectional view of the dressing system with the tensioning device of FIG. 15A according to one exemplary embodiment of the invention;

FIG. 15C is a diagram illustrating an elevation view of a dressing system 600N with the tensioning device 610 according to one exemplary embodiment of the invention;

FIG. 15D is a diagram illustrating an elevation view of the dressing system 600N of FIG. 15C with the end tensioning device 605A in an extended position according to one exemplary embodiment of the invention;

FIG. 15E is a diagram illustrating cross-sectional view of the dressing systems 600M, N of FIGS. 15A and 15C in an compressed state according to one exemplary embodiment of the invention;

FIG. 21 is a diagram illustrating a cross-sectional view of a shell system for covering and protecting a dressing system and allow for an airtight seal according to one exemplary embodiment of the invention;

FIG. 22A is a diagram illustrating a cross-sectional view of a suction device that may be used without a sponge for a wound according to one exemplary embodiment of the invention;

FIG. 22B is a diagram illustrating a cross-sectional view of the suction device of FIG. 22A without the wound environment according to one exemplary embodiment of the invention;

FIG. 23 is a diagram illustrating a side view of the suction device of FIG. 22 according to one exemplary embodiment of the invention;

DETAILED DESCRIPTION

The word "exemplary" is used herein to mean "serving as an example, instance, or illustration." Any aspect described herein as "exemplary" is not necessarily to be construed as preferred or advantageous over other aspects.

Figure 1A:
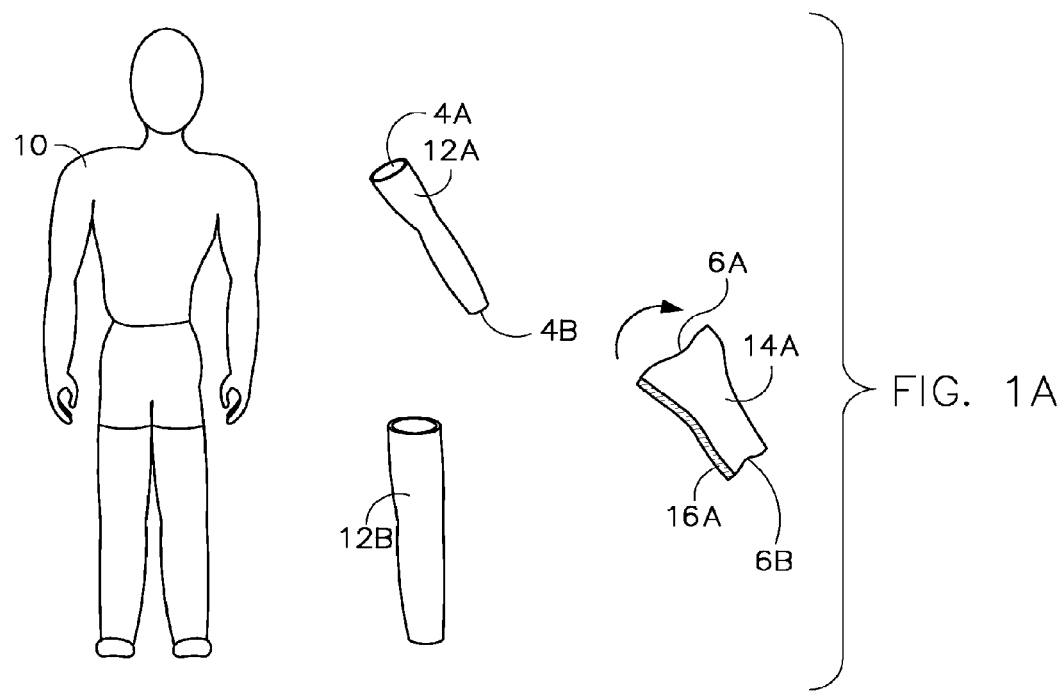
FIG. 1A is a diagram illustrating a few different exemplary embodiments for an envelope dressing applied to wounds on or in animal tissue.

Referring now to FIG. 1A, this figure is a diagram illustrating a few different exemplary embodiments for an envelope dressing 12 applied to wounds on animal tissue, such as on a human body 10. The envelope dressing 12 can be made from materials such as, but not limited to, rubber, plastic, or nylon. One ideal physical property for the material would be that it is elastic so that the material may expand or contract. Additionally, elastic material would allow for compression to control/manage edema/swelling within the soft tissues. The material, in some exemplary embodiments, will not include any latex in order to avoid any potential allergic reactions by an animal, like a human.

The dressings can be designed for specific location on the body such as the torso/chest/abdomen, the pelvis, the face/head, the lower extremity or the upper extremity. Similar to site specific plates for orthopedic stabilization, these dressings can incorporate different designs and applications suited for specific locations on the body. These dressings would be designed based on treatment goals, common problems with the area, anatomy, desired conditions to be monitored.

The material for the envelope dressing 12 may be impervious or non-impervious to liquids. The material for the envelope dressing 12 could also be made from a material that is transparent so that medical personnel can easily view the wound on the body 10 which is being covered by the dressing 12. The material may have multiple layers to allow for irrigation of wounds.

The material may be meshed in its makeup to allow for expansion and/or irrigation of a wound. The material may comprise elements which are bioabsorbable in order to prevent frequent changing of the dressing 12. The material may also include an antibacterial embedded therein in order to fight any local infections within the wound being covered by the dressing 12. The material may also comprise a carrier for bone morphogenic proteins (BMPs) or other biological factors in order to promote tissue healing. The material may also comprise channels or other parts of a delivery system for growth factors. According to one exemplary embodiment, the dressing 12 may comprise silicon for scar therapy softening.

The material for the envelope dressing 12 should allow the dressing 12 to be reusable for the same patient instead of being disposable like common ordinary dressings. The envelope dressing 12 may be made for different sizes and anatomic locations. For example, the first envelope dressing 12A may comprise a preformed shape designed for a specific area such as the forearm or full arm (from the hand to shoulder).

The preformed shape would dictate that certain portions of the envelope dressing 12A would have physical features that match its corresponding anatomical region. For example, a first end 4A of the envelope dressing 12A may have a first diameter, while the second end 4B of the envelope dressing 12A has a second diameter. If the first end 4A is designed to be close to the shoulder of the human body 10, then the first diameter will likely have a size which is greater than the second diameter corresponding to the second end 4B of the envelope dressing 12A.

The second envelope dressing 12B may comprise a preformed shape designed for specific areas such as the lower leg, and full leg (from the foot to the groin). Other anatomical areas may include, but are not limited to, the abdomen, chest, pelvis, head, face, hand, foot, etc. The dressing 12 may comprise a preformed tube that is elastic or one that is a wrap type design that allows for attachment of one end to the other, such as wrap 14A. For tubular embodiments, the employ dressing 12 would slide or cover over an entire extremity or maimed torso region. Application of the dressing could be applied by multiple methods but not limited to a slip on/over design. Alternative methods could include a lace up method, a zipper or Velcro.

The wrap 14A may comprise a fastening mechanism 16A that could comprise an adhesive strip or hook and loop fasteners sold under the well-known trade name Velcro™. Like the preformed tube, the wrap 14A may also have a preformed shape that matches its intended anatomical region. This means if the first wrap 14A is designed for a human leg, then the first end 6A of the wrap 14A may have a first length which is greater than a second length corresponding to the second and 6B of the rap 14A, when the wrap 14A is in an open or on unattached state. The exemplary embodiments of FIG. 1A illustrate how different parts of human anatomy may have different dressing designs and shapes.

Figure 1B:
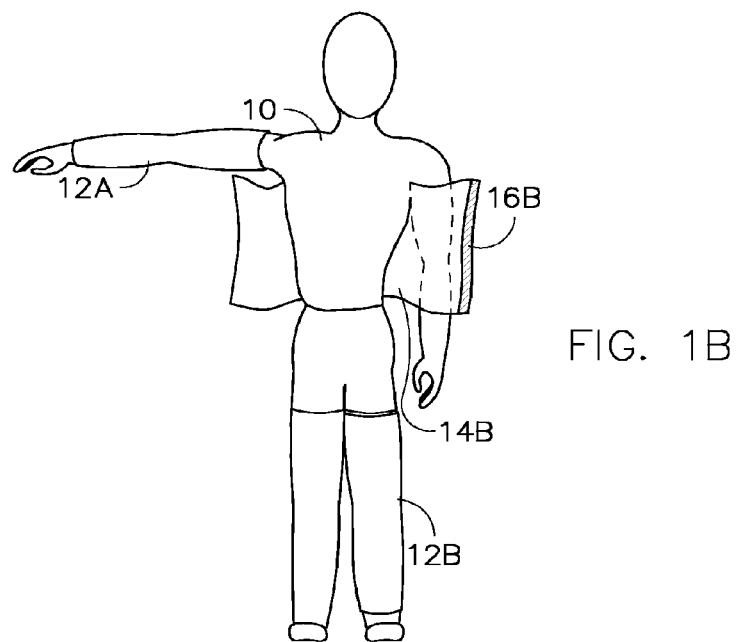
FIG. 1B is a diagram illustrating another envelope dressing according to one exemplary embodiment of the invention.

FIG. 1B is a diagram illustrating another envelope addressing comprising a wrap 14B according to one exemplary embodiment of the invention. In this exemplary embodiment, the wrap 14B is designed for the anatomical region of the torso of a human body. Specifically, the wrap 14B may be shaped for the abdomen and comprises a fastening mechanism 16B. The fastening mechanism 16B may be similar to the fastening mechanism 16A of FIG. 1A and it may comprise an adhesive strip or strips, or hook, lace, and loop fasteners.

Figure 2A:
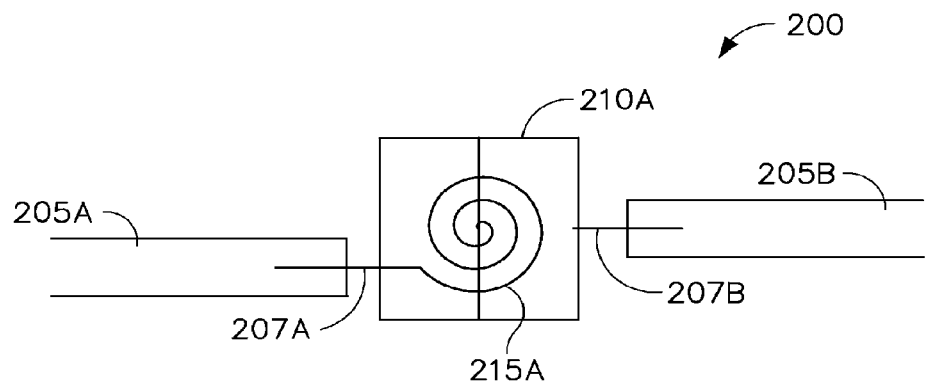
FIG. 2A is a diagram illustrating a tension sensor and FIG. 2B is a diagram illustrating a tension monitor system comprising the tension sensor of FIG. 2A that reacts to applied forces according to one exemplary embodiment of the invention.

FIG. 2A is a diagram illustrating a tension sensor or actuator 200 according to one exemplary embodiment of the invention. The tension sensor or actuator 200 and can be incorporated into any of the envelope dressings 12 and perhaps 14 described above and illustrated in FIG. 1. The tension sensor or actuator 200 may comprise a housing 210 that is coupled to a spring 215A. The spring 215A can comprise a torsional spring, however, other springs are within the scope of the invention and may include, but are not limited to, extension or tension springs and the like.

The tension sensor 200 may be coupled to a pair of ends 205 that are part of an envelope dressing 12. A first end 205A of the dressing 12 may include a first fastener 207A that couples to the spring 215A. A second end 205B of the dressing 12 may include a second fastener 207B that couples to the housing 210A. The first and second fasteners 207A, B may comprise wires, screws, hooks, clasps, or other like mechanical fasteners. The housing 210 for the tension monitor 200 may comprise any type of durable materials such as metal, plastic, ceramic, and other like materials.

Figure 2B:
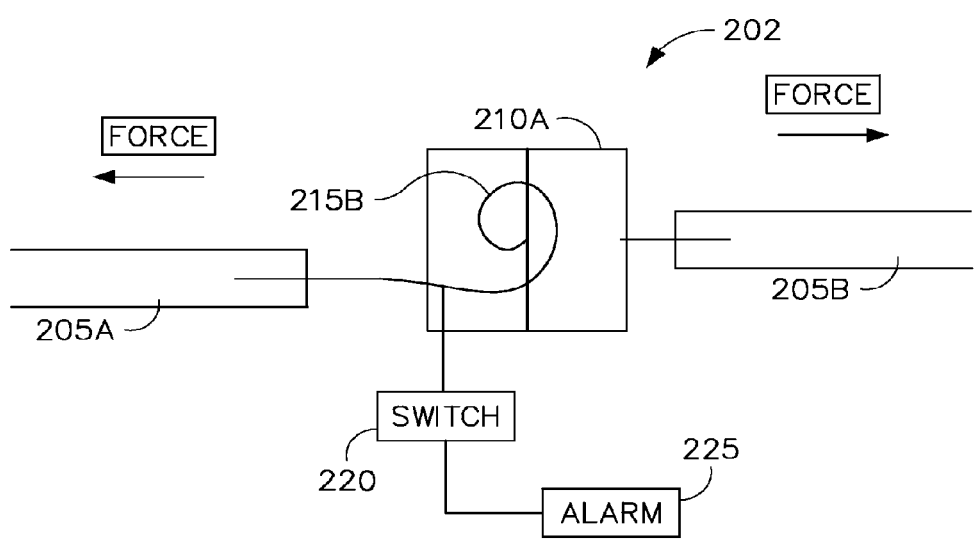

FIG. 2B is a diagram illustrating a tension monitor system 202 comprising the tension sensor 200 of FIG. 2A that reacts to applied forces according to one exemplary embodiment of the invention. In this exemplary embodiment, forces are applied to the first and second ends 205A, 205B of an envelope dressing 12. These forces could be the result of an expansion of the due to swelling of a wound in the human body 10.

The tension monitor system 202 may comprise a switch 220 that is coupled to the expanded spring 215B. The switch 220, in turn, may be coupled to an alarm 225. The switch to 20 may activate the alarm 225 when the spring 215 is in its expanded state as illustrated in FIG. 2B. The switch to 220 may comprise any one of a mechanical switch or an electrical switch or a combination of both types as apparent to one of ordinary skill in the art. The alarm 225 may comprise an audio type of alerting device such as a speaker. Alternatively, or in addition to, the alarm 225 may comprise a visual device such as a light emitting diode (LED) or other type of light device.

The tension monitor system 202 may monitor the tension placed on the envelope dressing 12 and it may sound alarm 225 is a certain threshold tension with respect to the dressing 12 was exceeded. The alarm 225 will likely be used to alert a clinician. The purpose of the tension monitor system 202 would be to allow for appropriate tension for an envelope dressing 12 or wrap 14 without causing the dressing 12 or wrap 14 to prevent blood flow to a particular wound being covered by the dressing 12 or wrap 14. The tension monitor system 202 may prevent over tensioning/tightening of the skin edges which would prevent blood flow and healing while causing tissue necrosis/death.

Figure 3A:
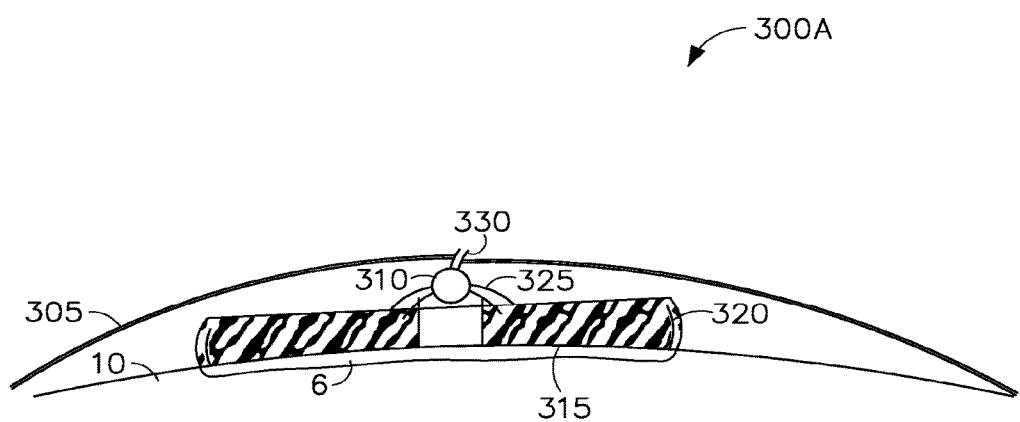
FIG. 3A is a diagram illustrating a cross-sectional view of a dressing system comprising a wound-vacuum combined with a near infrared spectroscopy (NIRS) sensor according to one exemplary embodiment of the invention.

FIG. 3A is a diagram illustrating a cross-sectional view of a dressing system 300A comprising a wound-vacuum 340 combined with a near infrared spectroscopy (NIRS) sensor 310 according to one exemplary embodiment of the invention. The dressing system 300A may comprise a sponge 315, a shell 320, suction tubing 325, conduits 330 for the NIRS sensor 310, and a covering 305. Conventional NIRS systems in their current form are usually unable to monitor open wounds/exposed tissue due to exudate build up and scabbing. The combination of a system to remove exudate and prevent light blockage would allow NIRS to monitor open tissue. The inventive system 300A may allow a NIRS sensor to be placed on an open wound. The vacuum system via suction tubing 325 may remove any wound/tissue exudate that would ultimately block the ability of NIRS sensor to obtain a reading.

The sponge 315 can comprise a porous material that can absorb liquids, such as, but not limited to, blood, and exudate that may be emitted from a wound 6. The sponge 315 may comprise synthetic materials such as, Polyvinyl acetate (PVA) (very dense, highly absorbent material with no visible pores) and polyester, and other like rubbery synthetic polymers such as a silicone, a plastic mat (not illustrated) with channels, ridges, bumps, or other like fluid channels to allow for suction of fluids and/or transmission of fluids. The porous material can be made from foamed plastic polymers, such as double-blown polyester. The sponge may have a high water retention ability, approaching or equalling PVA, but with visible pores.

The sponge 315 can be used on open wounds 6 within animal tissue 10. The shape of the sponge 315 can comprise a rectangle having a size on the order of 3 to 5 cm×6 to 8 cm. However, other shapes, such as, but not limited to, oval, elliptical, square, and the like are within the scope of the invention. Further, other sizes for the sponge 315 which are larger or smaller than the exemplary ranges disclosed above are within the scope of the invention.

The sponge 315 can absorb exudate that could interfere with the NIRS sensor 310 if the sponge 315 were not present. The shell 320 which encloses or encompasses the sponge 315 can comprise a solid material such as plastic or rubber. The cover 305 which is positioned over and encompasses the shell 320 and holding the shell in place can comprise an adhesive, cloth like material similar to a bandage. The cover 305 and shell 320 can form an airtight seal over the open wound 6 in the body tissue 10. According to an alternate exemplary embodiment, an adhesive perimeter may be provided around the sponge 315 to create a airtight seal instead of a film over the sensor.

The NIRS sensor 310 may be positioned between a side of the sponge 315 and the cover 305. Further details of the NIRS sensor 310 will be described below in connection with FIG. 3B.

FIG. 3B is a diagram illustrating an elevation view of the dressing system 300A comprising a wound-vacuum 340 combined with a near infrared spectroscopy (NIRS) sensor 310 of FIG. 3A according to one exemplary embodiment of the invention. In this FIG. 3B, the adhesive cover 305 is not illustrated so that further details of the dressing system 300A can be seen.

The NIRS sensor 310 may comprise a light emitter 307, a superficial light sensor 335A, a deep tissue light sensor 335B, and a skin sensor 332. The light emitter 307 can comprise an optical waveguide, such as an optical fiber, which is coupled to a light source 350, such as a light emitting diode (LED) laser. The light sensors 335 can comprise photodiodes or other similar light detecting equipment.

The superficial light sensor 335A may detect reflected light from shallow areas of the monitored tissue 10 while the deep tissue light sensor 335B may detect reflected light from deeper areas of the monitored tissue 10 within the wound 6. The skin sensor 332 can detect pigmentation of the skin so that the light source 307 can adjust its intensity in response to the detected pigmentation by the skin sensor 332.

The NIRS sensor 310 can detect oxygenation levels within the blood that flows near or adjacent to the wound 6. Low oxygenation levels or the absence of any oxygenation levels can indicate a hematoma or poor blood circulation which are undesirable and which would require intervention by medical personnel. Alternatively, the NIRS readings may demonstrate devitalized or dead tissue which could become a nidus for infection and would require surgical debridement.

The NIRS sensor 310 may be coupled to a control panel of a computer 345 by a conduit 330 that can encase communication cables connected to the light emitter 307 and the light sensors 335. The computer 345 can be coupled to or can comprise an alarm 225. The alarm 225 can comprise an audible and/or visual indicator. An audible indicator may include a speaker while a visual indicator may comprise a light source such as a blinking LED. The alarm 225 may be activated by the computer 345 when the low absence of an oxygenation level condition discussed above is detected.

The suction tubing 325 can comprise relatively thin, hollow conduits that are positioned within the sponge 315 in order to draw or suck out liquid/exudate absorbed by the sponge 315 from the wound 6 in the tissue 10. As illustrated in FIG. 3B, the four ends of the suction tubing 325 form an "X" shape in which each end is positioned within the sponge 315 for creating a vacuum adjacent to the ends. The tubing 325 can be made from a range of polymers, and may include, but is not limited to silicone rubber latex and thermoplastic elastomers. Silicone may be one of the most common choices because it is inert and unreactive to body fluids and a range of medical fluids with which it might come into contact. Other materials may include, but are not limited to, plastic and hard rubbers, or a combination thereof.

The four ends of the suction tubing 325 may meet together at a junction and feed into a single exit tube 325A which is coupled to a pump 340. The pump 340 can be of any type which is appropriate for creating a vacuum adjacent to the wound 6 for removing fluids and/or particulates that can be emitted from the wound. Exemplary pumps include, but are not limited to, displacement pumps, buoyancy pumps, compressed-air-powered double-diaphragm pumps, impulse pumps, hydraulic ram pumps, velocity pumps, centrifugal pumps, radial flow pumps, axial flow pumps, mixed flow pumps, and eductor-jet pumps, just to name a few.

The computer 345, light source 350, and alarm 225 can be housed within a single unit or housing as appropriate and as determined by one of ordinary skill the art. Alternatively, each component could be separate from one another depending upon the wound care environment and relative sizes of the respective components.

Figure 4:
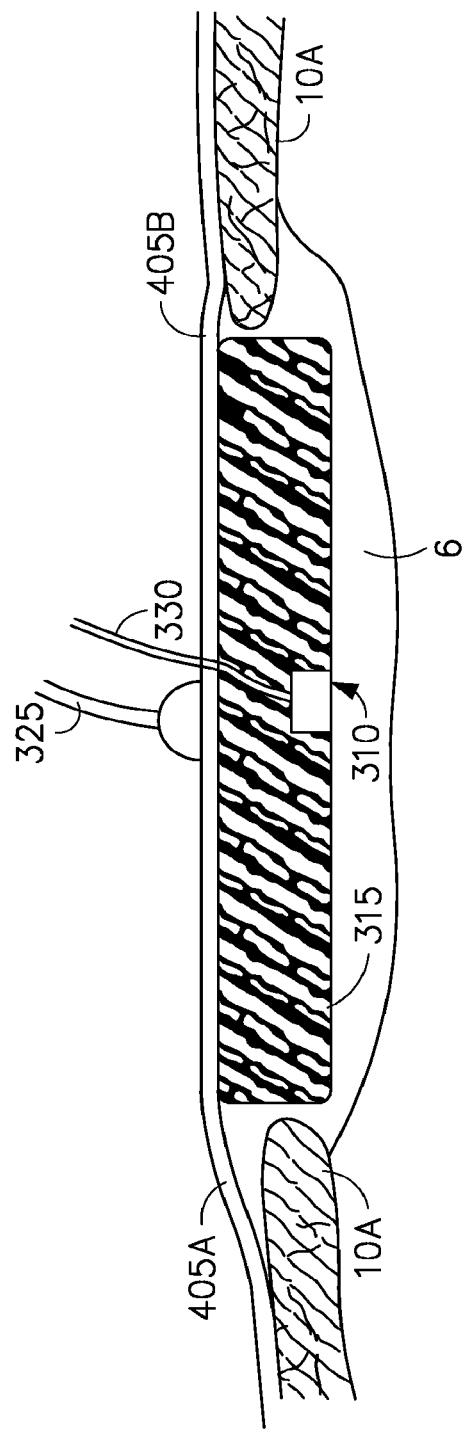
FIG. 4 is a diagram illustrating a cross-sectional view of another dressing system comprising a wound-vacuum combined with a near infrared spectroscopy (NIRS) sensor according to one exemplary embodiment of the invention.

FIG. 4 is a diagram illustrating a cross-sectional view of another dressing system 300B comprising a wound-vacuum combined with a near infrared spectroscopy (NIRS) sensor 310 according to one exemplary embodiment of the invention. Specifically, this system 300B comprises a larger wound dressing that incorporates the NIRS sensor 310 as part of the device to monitor tissue viability/perfusion under the dressing. The dressing system 300B illustrated in FIG. 4 also shares several elements which are similar to those of the dressing system 300A in FIG. 3. Therefore, only the differences between these two figures will be discussed and described in further detail below.

In this exemplary embodiment, the NIRS sensor 310 may be positioned within the sponge 315 and adjacent to the wound 6. This exemplary embodiment allows for monitoring of tissue viability under the sponge 315 and may allow for continued monitoring of perfusion and as well as parameters related to healing for the wound 6. The dressing system 300B may further comprise another cover 405 which may be similar to cover 305 of FIG. 3.

In the exemplary embodiment illustrated in FIG. 4, the wound 6 may be significantly larger relative to the wound 6 illustrated in FIGS. 3A-3B. Also the wound 6 may have an oval or an elliptical shape. The sponge 315 would be designed to mirror this shape. The relative size of the sponge 315 may include a large diameter of approximately 40 cm and a smaller diameter of approximately 20 cm. However, one of ordinary skill in the art will appreciate that other magnitudes larger or smaller than those disclosed are clearly within the scope of the invention. Further, one of ordinary skill in the art recognizes that other shapes such as square, rectangular, and the like are within the scope of the invention. Additionally, the sponge will be able to be trimmed to fit different size wounds.

Figure 5:
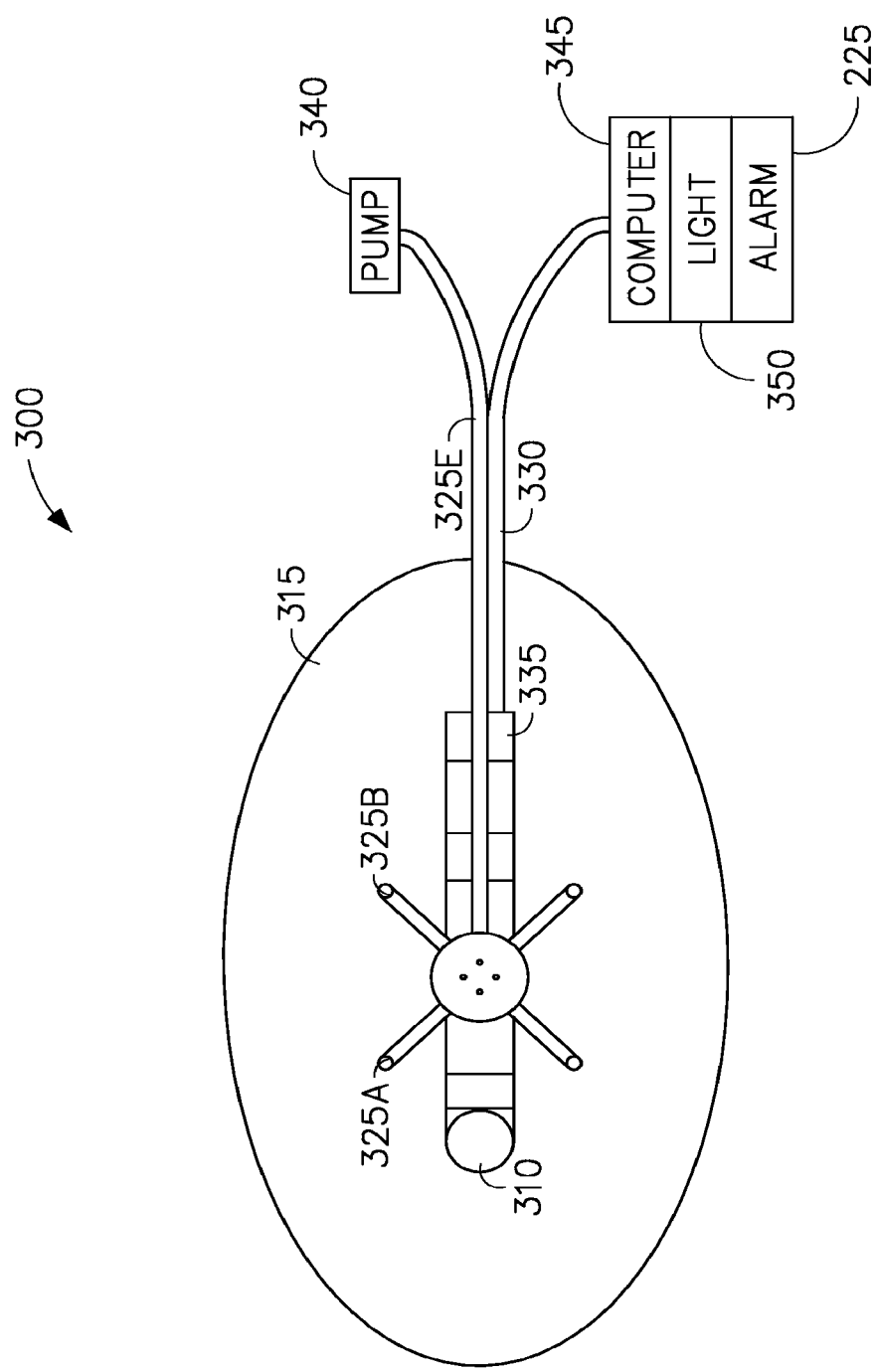
FIG. 5 is a diagram illustrating an elevation view of the wound-vacuum combined with the NIRS device of FIG. 4 according to one exemplary embodiment of the invention.

FIG. 5 is a diagram illustrating an elevation view of the dressing system 300B comprising a wound-vacuum combined with a near infrared spectroscopy (NIRS) sensor 310 of FIG. 4 according to one exemplary embodiment of the invention. The sponge 315 in this exemplary embodiment may comprise an oval or elliptical shape as noted above.

In this exemplary embodiment, the computer 345, light source 350, and the alarm 225 are illustrated as being housed in a single unit or a unitary casing. As noted previously, these elements may be housed in a single casing or they may occupy separate housings as appropriate for a particular monitoring situation and as determined by one of ordinary skill in the art.

Figure 6A:
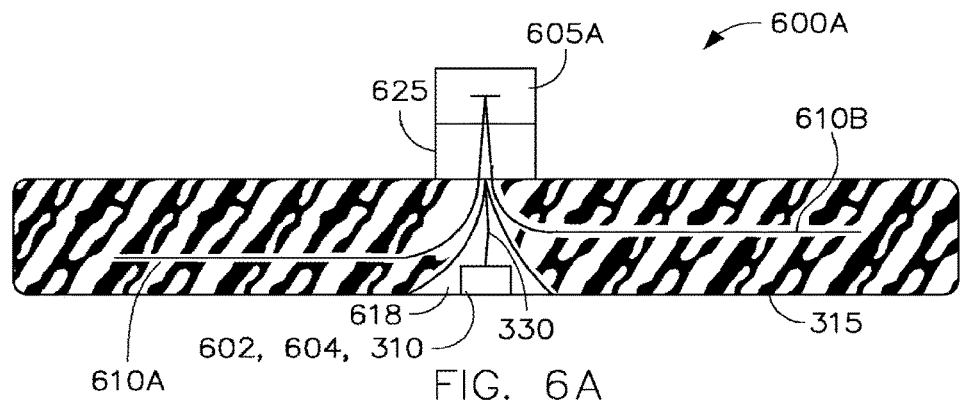
FIG. 6A is a diagram illustrating a cross-sectional view of another dressing system comprising a wound-vacuum combined with a NIRS sensor and a tensioning device according to one exemplary embodiment of the invention.

FIG. 6A is a diagram illustrating a cross-sectional view of another dressing system 600A comprising a wound-vacuum combined with a NIRS sensor 310 and a tensioning device 610 according to one exemplary embodiment of the invention. In this exemplary embodiment, the dressing system 600A may comprise two sponges: a first sponge 315 and a second sponge 618. The first sponge 315 can comprise materials similar to the sponges 315 described above.

However, the second sponge 618 may comprise materials similar to those of the first sponge 315 but with a higher strength, modulus, and/or density such that the stiffness or rigidity of the second sponge 618 is higher relative to the first sponge 315. The second sponge 618 will generally remain stationary relative to the entire system 600A while the first sponge 315 may move and contract under compressive or tension type of forces. Relative to the first sponge 315 which may have an elliptical or oval shape, the second sponge 618 may comprise a prismatic shape in which the second sponge 618 may take the form a triangular prismatic shaped beam.

The dressing system 600A may further comprise an end tensioning mechanism 605A. The end tensioning mechanism 605A can comprise an anchor member that can grasp or retain an end section of the tension device 610, also referred to as an endoskeleton. The end tensioning mechanism 605A may be positioned upon a central longitudinal member 625 that has holes or apertures through which the tension members 610A, 610B can be pulled therethrough.

The tension device or endoskeleton 610 may comprise a first tension member 610A and a second tension member 610B. The endoskeleton 610, end tensioning mechanism 605A, and central longitudinal member 625 may comprise a heavy duty, repeated use material such as nylon ribbon or a sturdy plastic ribbon. However, other materials, such as, but not limited to metal, are within the scope of the invention. This material for the endoskeleton 610 and particularly, the tension members 610A, 610B allow for compression or retraction of the sponge 315 when tensile forces are applied to the tension members 610A, 610B with the end tensioning mechanism 605A. Additionally, the tensioning mechanism 605 may be separated so each side of the wound 6 can be tensioned independently through having two independent longitudinal spines and separate cranks (See FIGS. 6X & Y described below.)

According to this exemplary embodiment, additional sensors beyond the NIRS sensor 310 can be provided such as a pH sensor 602 and a thermometer 603. The pH sensor 602 can monitor the relative acidity of the wound area while the thermometer 603 can monitor temperature in regions of tissue adjacent to the thermometer 603.

Figure 6B:
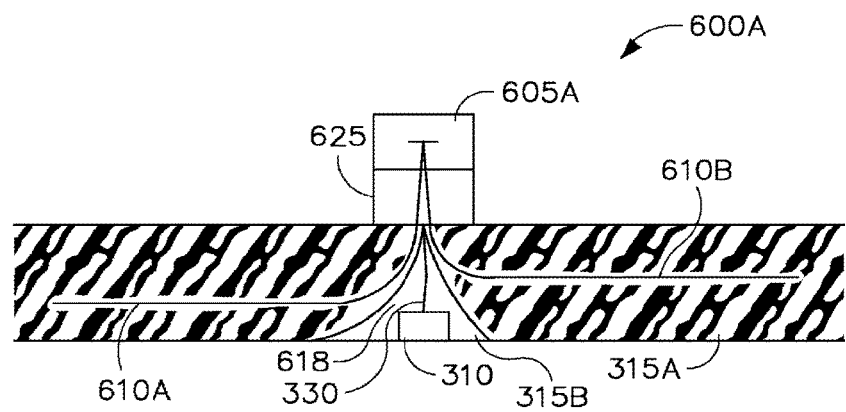
FIG. 6B is a diagram illustrating an increased magnification of the cross-sectional view of the dressing system of FIG. 6A according to one exemplary embodiment of the invention.

FIG. 6B is a diagram illustrating an increased magnification of the cross-sectional view of the dressing system 600A of FIG. 6A according to one exemplary embodiment of the invention. The triangular prismatic shaped beam second sponge 618 is more readily apparent in this exemplary Figure.

Figure 6C:
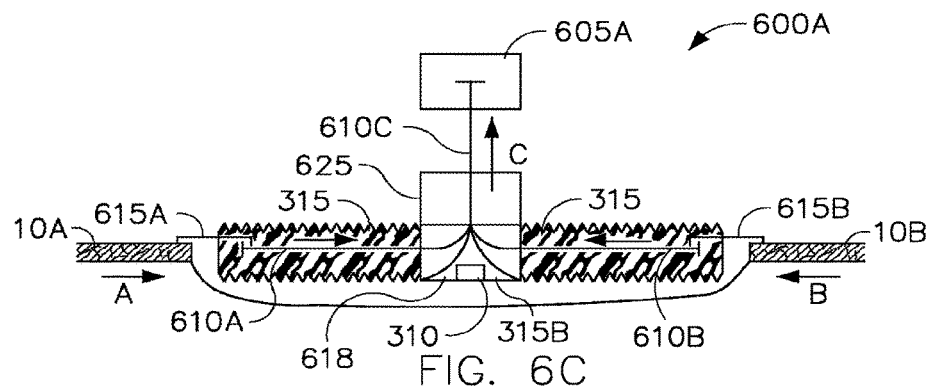
FIG. 6C is a diagram illustrating another cross-sectional view of the dressing system in which tension forces are applied to the dressing system according to one exemplary embodiment of the invention.

FIG. 6C is a diagram illustrating another cross-sectional view of the dressing system 600A in which tension forces are applied to the dressing system 300A according to one exemplary embodiment of the invention. In this exemplary embodiment, the end tensioning mechanism 605A is pulled in a direction as indicated by arrow C. Further, the central longitudinal member 625 has been removed from this view so that the movement of the tensioning device 610, and particularly its tensioning members 610A, 610B is readily seen. Meanwhile, the central longitudinal member 625 is present in a working embodiment, though not illustrated in this Figure.

Section 610C of the endoskeleton 610 may comprise two members which are positioned together because of the tension force exerted on the end tensioning mechanism 605A. Meanwhile, FIG. 6C only illustrates section 610 C to comprise a single member when in fact two members may form the section. The two members of section 610C may comprise portions of the first tension member 610A and the second tension member 610B.

The movement of section 610C causes the first tension member 610A to move in a direction as indicated by arrow A. The movement of section 610C also causes the second tension member 610B to move in a direction as indicated by arrow B.

The first tension member 610A and the second tension member 610B are secured to portions of the sponge 315 as well as to skin sections 10A, 10B. The first and second tension members 610A, 610B may be attached to skin sections 10A, 10B by one or more fastening mechanisms 615A, B. The fastening mechanisms 615A, B may comprise staples, suture threads, metal rings, and other like fastening devices. According to one preferred and exemplary embodiment, the fastening mechanisms 615A, B may comprise staples.

With the fastening mechanisms 615A, B, the tension members 610A,B will pull skin sections 10A, B towards each other when tensile forces such as indicated by arrows A, B are applied to these tension members 610A, B. This action also causes sections of the first sponge 315 coupled to the tension members 610A, B to compress. Meanwhile, the second sponge 618 because it has a higher rigidity or stiffness relative to the first sponge 315, does not undergo any compression or very little or minute amounts of compression with respect to its volume relative to the volume of the first sponge 315. This provides a stable housing for NIRS, suction, pH monitoring, etc.

The application of these tensile forces to the two tension members 610A, B in a gradual manner over time allows the wound 6 to heal more rapidly and consistently without the use of skin grafts and other types of ancillary surgical procedures. The compressive nature of the sponge 315 allows the dressing system 600A to adjust its relative size while the size of the wound 6 is being reduced due to healing and movement of the skin sections 10A, 10B.

FIG. 6D is a diagram illustrating an elevation view of the dressing system 600A of FIG. 6A according to one exemplary embodiment of the invention. The dressing system 600A illustrated in FIG. 6D shares several elements which are similar to those of the dressing system 300 in FIG. 3. Therefore, only the differences between these two figures will be discussed and described in further detail below.

The endoskeleton 610 may comprise a plurality of ribs as seen from this view that are made of respective pairs of tensioning members 610A, 610B. In the exemplary embodiment illustrated in FIG. 6D, there are five pairs of tensioning members that include a first pair 610A1, 610 B1; a second pair 610A1, 610B2; a third pair 610A3, 610B3; a fourth pair 610A4, 610B4; and a fifth pair 610A5, 610 B5. Each tensioning member 610 may be coupled to a central longitudinal member 625 that intersects each tensioning member 610 at an approximately 90 degree angle.

The sponge 315 generally has an area that is approximately the same size as the wound 6 in the tissue 10. In the exemplary embodiment illustrated in FIG. 6D, there are two ends 635A, 635B of the wound 6, which are not covered by the sponge 315 because of the shape of the wound 6.

The central longitudinal member 625 may be referred to as a spine relative to the tensioning members 610 which can be referred to as ribs. At each end of the central longitudinal member 625 can comprise a bearing 620 or other type of holding mechanism that allows for the central longitudinal member 625 to rotate as indicated by directional arrows A illustrated in FIG. 6D.

Each tensioning member 610 may comprise a substantially planar material, like a solid tape analogous to a how a conventional, flexible tape measure may be constructed, which is both stiff and flexible. See FIG. 19 which is described more fully below and which further explains this flexible tape measure-like structure. As illustrated in FIG. 6D, each tensioning member 610 has a first end which is coupled to an edge of tissue 10 by two fastening mechanisms, such as staples 615. One of ordinary skill the art will appreciate that fewer or additional fastening mechanisms can be used without departing from the scope of the invention. Each tensioning member 610, as discussed above, also has a second end which is attached to the central longitudinal member 625.

As mentioned previously, the central longitudinal member 625 or spine may be permitted to rotate through the use of a pair of bearings 620A, 620B or other similar holy mechanisms. Because each tensioning number 610 is attached to the central longitudinal member 625, each tensioning member 610 "rolls up" and wraps around the central longitudinal member 625 as it is rotated. This rotation of the central longitudinal member 625 in combination with the "rolling up" of the tensioning members 610 causes the first ends of the tensioning member 610 attached to the tissue 10 by fasteners 615 two contract and move towards each other as illustrated in FIG. 6E.

FIG. 6E is a diagram illustrating an elevation view of the dressing system 600A of FIG. 6A in which tension forces have been exerted by the tensioning device 610 according to one exemplary embodiment of the invention. The dressing system 600A illustrated in FIG. 6E shares several elements which are similar to those of the dressing system 600A in FIG. 6D. Therefore, only the differences between these two figures will be discussed and described in further detail below.

As mentioned above, the central longitudinal member 625 or spine of the dressing system 600A is permitted to rotate so that each tensioning member 610 "rolls up" and wraps around the central longitudinal member 625 as it is rotated. The portions of the tensioning member 610 that are collected or rolled up on the central longitudinal member 625 form spools of material 610 C1-C5 that are wrapped around the central longitudinal member 625 as illustrated in FIG. 6E.

FIG. 6D illustrates how the tensioning members 610 can further close the wound 6 as the tensing members 610 are reeled or rolled up on the central longitudinal member 625. Compared to FIG. 6D, the two ends 635A, 635B of the wound 6 are no longer present in FIG. 6E because the width across the wound 6 has been reduced due to healing and due to the tension forces exerted by the tensioning member 610 on the tissue 10. Specifically, the tensioning member 610 in combination with the staples 615 have pulled the edges of the tissue 10 closer together relative to each other. The suction may reduce edema so that the edges of the wound 6 can be more closely approximated while the tension draws the edges in as well. FIG. 6D also illustrates how the sponge 315B, having an oval shape, which houses the NIRS device is stationary and does not compress or retract with tension of the tensioning members 610. The sponge 315B may comprise a less compliant or flexible material relative to the compressive sponge 315 in order to reduce or prevent compression but which still allows for transmission of the negative pressure to the wound 6. Also the sponge 315B housing the NIRS device may also have other shapes as needed, such as, but not limited to, rectangular, square, circular, and other similar geometrical shapes.

FIG. 6E also illustrates how the suction tubing 325 may be contracted when the tensioning member 610 are reeled or wound up on the central longitudinal member 625. The suction tubing 325 may be pulled up or moved up towards the pump 340 as the central longitudinal member 625 is rotated so that any excess suction tubing is positioned appropriately within the sponge 315 as it is contracted by the tensioning members 610. The tubing will usually be stable enough that they do not collapse and prevent transmission of the suction during tensioning.

Figure 6F:
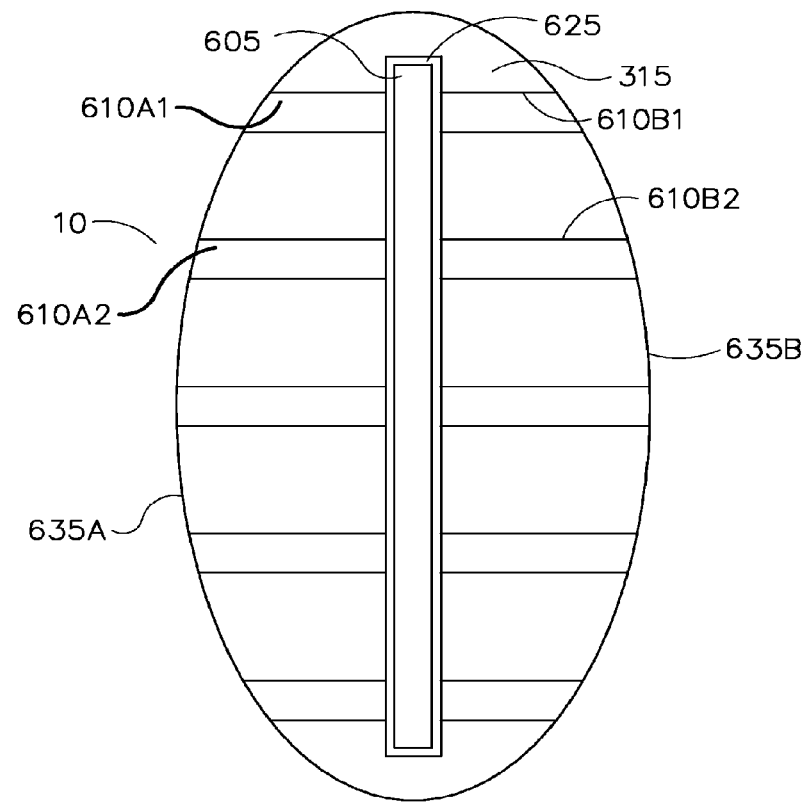
FIG. 6F is a diagram illustrating an elevation view of a dressing system without a NIRS device with the tensioning device of FIGS. 6A-6C according to one exemplary embodiment of the invention.

FIG. 6F is a diagram illustrating an elevation view of a dressing system 600B with the tensioning device 610 of FIGS. 6A-6C without a NIRS device according to one exemplary embodiment of the invention. The dressing system 600B illustrated in FIG. 6F shares several elements which are similar to those of the dressing system 600A in FIGS. 6D-6E. Therefore, only the differences between these figures will be discussed and described in further detail below.

The tensioning device 610 comprises the end tension mechanism 605A which is positioned on the central longitudinal member 625. As noted previously, end the tension mechanism 605A can comprise an end section of the tension device 610 and it may be coupled to a first tension member 610A and a second tension member 610B. According to this exemplary embodiment, the dressing system 600B does not comprise a NIRS sensor 310. Further, while fastening mechanisms such as staples 615 have not been illustrated, they are likely used with this embodiment for connecting to the tissue 10 to the tension members or ribs 610, 610B.

According to this exemplary embodiment, the end tensioning mechanism 605A can comprise a longitudinal prismatic beam member that has a rectangular cross section. However, one of ordinary skill the art will appreciate that other shapes for the cross section, such as circular, elliptical, or other polygonal shapes are included within the scope of the invention.

Figure 6G:
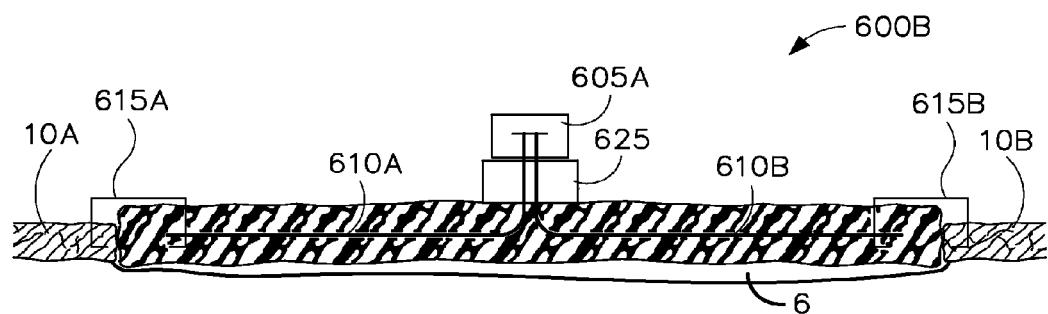
FIG. 6G is a diagram illustrating a cross-sectional view of the dressing of FIG. 6F without any tensile forces applied to the dressing system according to one exemplary embodiment of the invention.

FIG. 6G is a diagram illustrating a cross-sectional view of the dressing system 600B of FIG. 6F without any tensile forces applied to the dressing system 600B according to one exemplary embodiment of the invention. As noted previously, the tensioning members 610A, 610B may be coupled to the tissue 10 with fastening mechanisms, such as staples 615.

In this view of FIG. 6G, the coupling between the end tension mechanism 605A in the tensioning members 610 A,B is illustrated. As discussed above in connection with FIG. 6F, the tensioning members 610 A,B flow or moved through apertures within the central longitudinal member 625 when the end tension mechanism 605A is moved apart and away from the central longitudinal member 625.

Figure 6H:
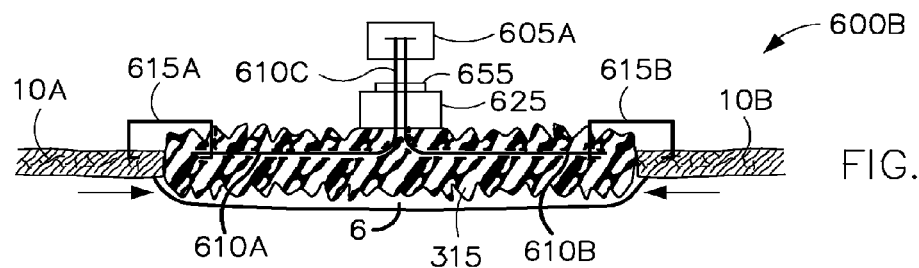
FIG. 6H is a diagram illustrating a cross-sectional view of the dressing system of FIG. 6F with tensile forces applied to the dressing system according to one exemplary embodiment of the invention.

FIG. 6H is a diagram illustrating a cross-sectional view of the dressing system 600B of FIG. 6F with tensile forces applied to the dressing system 600B according to one exemplary embodiment of the invention. According to this exemplary embodiment, the end tensioning mechanism 605A has been displaced or moved away from the central longitudinal member 625, causing the central section 610C to be displaced from the central longitudinal member. The movement of the tensioning mechanism 605A and the central section 610C causes the tensioning members 610A,B to move in a direction towards the central longitudinal member 625 and therefore, pulling ends of the tissue 10A,B towards each other while contracting the sponge 315.

A locking mechanism 655 is further illustrated in which it is positioned between the end tensioning mechanism 605A and the central longitudinal member 625. The locking mechanism 655 can comprise a device which pinches or grasps the tensioning members 610A, 610B as they are pulled through the central longitudinal member 625.

Figure 6I:
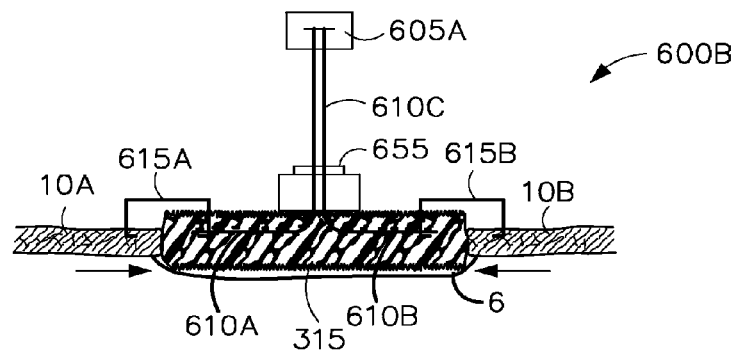
FIG. 6I is a diagram illustrating a cross-sectional view of the dressing system of FIG. 6H with additional tensile forces applied to the dressing system according to one exemplary embodiment of the invention.

FIG. 6I is a diagram illustrating a cross-sectional view of the dressing system 600B of FIG. 6H with additional tensile forces applied to the dressing system 600B according to one exemplary embodiment of the invention. According to this view, relative to FIG. 6H, the tensioning members 610A,B have been further contracted and pulled through the central longitudinal member 625 causing the sponge 315 to be compressed further while the ends of the tissue 10A,B have been drawn closer together.

FIG. 6H and FIG. 6I illustrate how tensile forces can be applied to a wound 6 over time, and specifically to the ends of the healthy tissue 10A, 10B that surround the wound 6. By applying these tensile forces over time, the size of the wound 6 can be decreased over time and can promote natural healing of the wound 6 without any additional surgical procedures, such as skin grafts, that are often used to help heal large, open wounds 6.

Figure 6J:
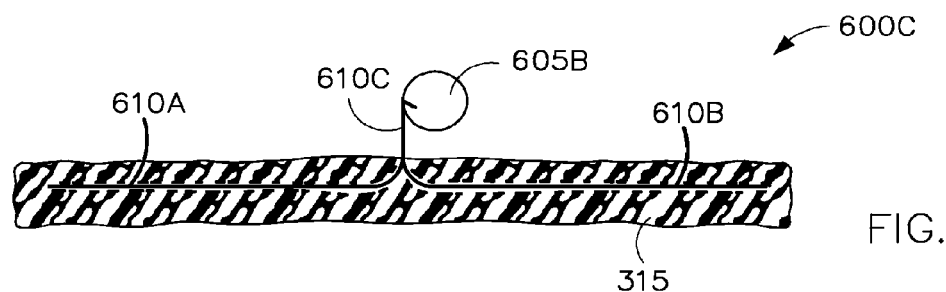
FIG. 6J is a diagram illustrating a cross-sectional view of another dressing system having another type of end tensioning mechanism in the tensioning device according to one exemplary embodiment of the invention.

FIG. 6J is a diagram illustrating a cross-sectional view of another dressing system 600C having another type of end tensioning mechanism 605B in the tensioning device 610 according to one exemplary embodiment of the invention. In this dressing system 600C, the end tensioning mechanism 605B can comprise a spool that operates similar to the central longitudinal member 625 of FIG. 6D. In this exemplary embodiment, a central longitudinal member 625 is not present.

While not illustrated in this figure, the tensioning members 610 A, B can be coupled to ends of the tissue 10 with staples 615. This exemplary embodiment has a simpler design relative to FIG. 6D because it has fewer parts. In other words, this exemplary embodiment does not have a central longitudinal member 625 and NIRS sensors 310 like those of FIG. 6D.

Figure 6K:
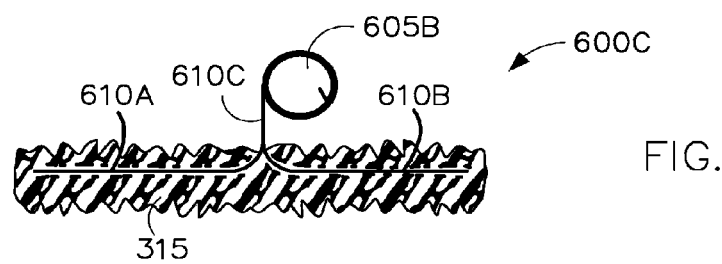
FIG. 6K is a diagram illustrating the dressing system of the FIG. 6J with tensile forces applied to the dressing system according to one exemplary embodiment of the invention.
Figure 6L:
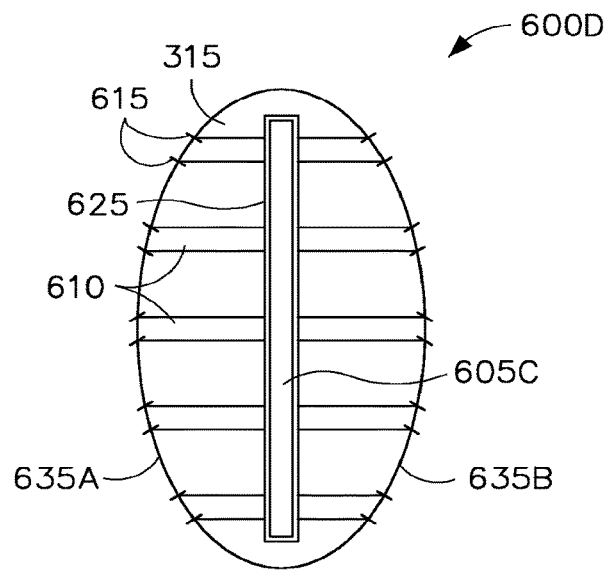
FIG. 6L is a diagram illustrating an elevation view of a dressing system with another type of end tensioning mechanism according to one exemplary embodiment of the invention.
Figure 6M:
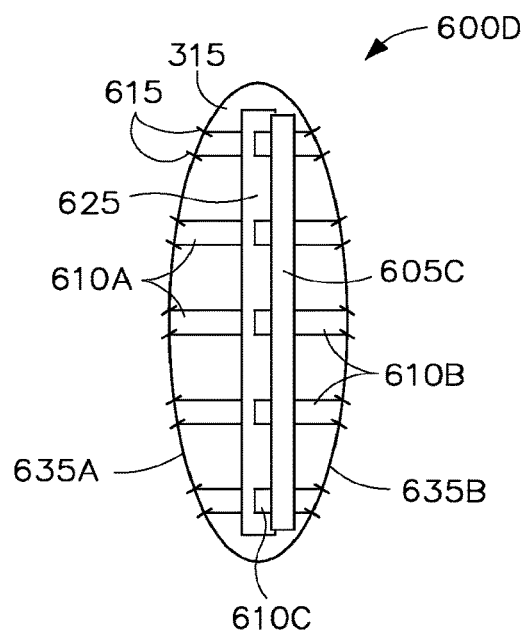
FIG. 6M is a diagram illustrating an elevation view of the dressing system of FIG. 6L after further tensile forces have been applied according to one exemplary embodiment of the invention.

FIG. 6K is a diagram illustrating the dressing system 600C of the FIG. 6J with tensile forces applied to the dressing system 600C according to one exemplary embodiment of the invention. In this exemplary embodiment, the tensioning members 610 A, B have been reeled up or further wound onto the spool 605B causing the sponge 315 to further contract or compress.

Figure 6N:
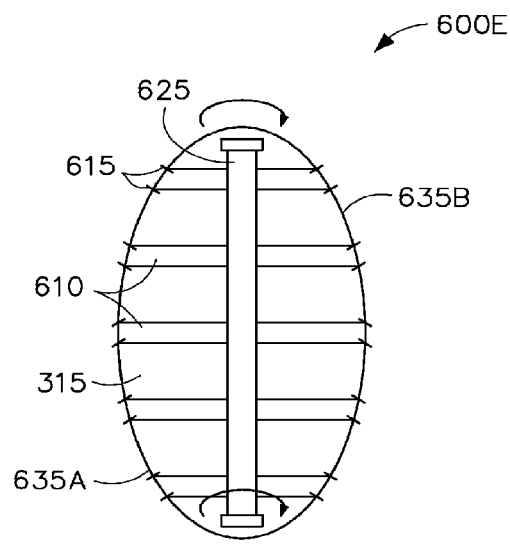
FIG. 6N is a diagram illustrating an elevation view of a dressing system with the tensioning device of FIGS. 6D-E according to one exemplary embodiment of the invention.

FIG. 6N is a diagram illustrating an elevation view of a dressing system 600E with the tensioning device 610 of FIGS. 6D-E according to one exemplary embodiment of the invention. The dressing system 600E illustrated in FIG. 6N shares several elements which are similar to those of the dressing system 600A in FIGS. 6D-6E. Therefore, only the differences between these figures will be discussed and described in further detail below.

In this exemplary embodiment, the dressing system 600 E does not have a NIRS sensor 310 or a vacuum system with a pump 340. The tensioning members 610A,B of this exemplary embodiment can be reeled or wound up on the central longitudinal member 625.

Figure 6O:
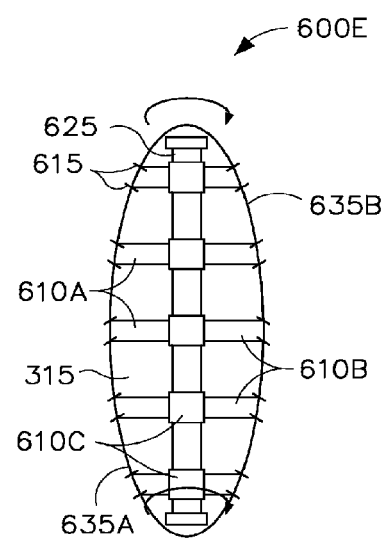
FIG. 6O is a diagram illustrating an elevation view of the dressing system of FIG. 6N after further tensile forces have been applied according to one exemplary embodiment of the invention.

FIG. 6O is a diagram illustrating an elevation view of the dressing system 600E of FIG. 6N after further tensile forces have been applied according to one exemplary embodiment of the invention. In this exemplary embodiment, as the tensioning members or ribs 610A, B are wound around the central longitudinal member 625, this causes the sponge 315 two contract while shrinking the size of the wound 6.

Figure 6P:
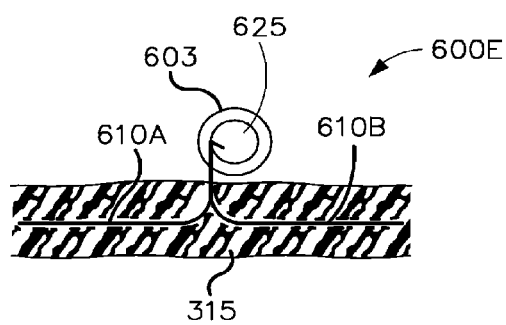
FIG. 6P is a diagram illustrating a cross-sectional view of the dressing system of FIG. 6N according to one exemplary embodiment of the invention.

FIG. 6P is a diagram illustrating a cross-sectional view of the dressing system 600E of FIG. 6N according to one exemplary embodiment of the invention. In this exemplary embodiment, a housing 603 comprising a tubular member may enclose or encompass the central longitudinal member 625 on which the tensioning members or ribs 610 A,B may be wound. In this view, the tensioning members 610A,B have not been wound.

Figure 6Q:
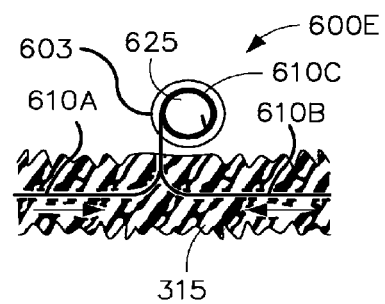
FIG. 6Q is a diagram illustrating a cross-sectional view of the dressing system of FIG. 6O according to one exemplary embodiment of the invention.

FIG. 6Q is a diagram illustrating a cross-sectional view of the dressing system 600E of FIG. 6O according to one exemplary embodiment of the invention. In this exemplary embodiment, the tensioning members 610A,B have been wound around the central longitudinal member 625. As noted previously, the central longitudinal member 625 is encased by a housing 603 which can contain and protect the tensioning members 610A,B as they are wound around the central longitudinal member 625. The movement of the tensioning members 610A,B as indicated by the arrows causes the sponge 315 to contract and/or compress.

FIG. 6R is a diagram illustrating a cross-sectional view of a dressing system 600F with another type of locking mechanism 655A for the end tensioning mechanism 605 according to one exemplary embodiment of the invention. Specifically, this diagram depicts a safety mechanism that will allow for a controlled/measured failure mechanism for the tensioning system in order to prevent too much tension to be applied to the skin edges.

According to this exemplary embodiment, the locking mechanism 655A may comprise a housing 662, springs 660, and force applicators 665. The housing 662, springs 660, and force applicators 665 can comprise a material such as plastic or metal. The springs 660 are made of metal in preferred exemplary embodiments. While the springs 660 have been illustrated as compression springs, other types of springs such as tension or torsional springs are within the scope of the invention as recognized by one of ordinary skill in art.

The springs 660 can be coupled to the housing 662 and may exert forces against the force applicators 665. Each force applicator 665 can press against a tension member 610A,B. The opposing compression forces of the two springs 665 illustrated in FIG. 6R can lock or can prevent movement of the tensioning members 610 A,B through the locking mechanism 655A.

The forces of the two springs 665 may have a magnitude that prevents movement of the tensioning members 610 A,B through the locking mechanism 655A when no tensile forces are applied to the tensioning members 610 A,B. However, the forces of the two springs 665 may have a magnitude which also permits movement of the tensioning members 610 A,B through the locking mechanism 655A when tensile forces are applied to the end tensioning mechanism 605A.

This embodiment also serves as a safety feature. This force of the locking mechanism 655A can be set so that too much tension cannot be applied by medical personnel. This mechanism would prevent medical personnel from pulling the tensioning system too tight and locking it down. The release mechanism would not catastrophically fail but simply release the excess tension but not completely release all tension. Once the tension is released to an acceptable level the lock would maintain the appropriate tension. This aspect will prevent tissue ischemia from over tensioning.

FIG. 6S is a diagram illustrating a cross-sectional view of a dressing system 600G with another type of locking mechanism 655B according to one exemplary embodiment of the invention. According to this exemplary embodiment, the locking mechanism 655B comprises a ratcheting system that includes a ratchet gear 670 and a pawl 675 that engages the teeth of the gear 670. The locking mechanism 655B allows the tension member 610A, B to be wound upon the central longitudinal member 625 such that the tensioning members 610A, B are held in place and locked as they are wound around the central longitudinal member 625. This diagram depicts a safety mechanism for a locking mechanism 655B that will allow for a "controlled/measured failure mechanism" for the tensioning system in order to prevent too much tension to be applied to the skin edges. The controlled failure mechanism relieves tension if medical personnel attempt to apply to great of a tension. The latches in FIG. 6S will release and reset at a lower tension or as in FIG. 6T, described below, the tensioning cords will slide back until a safe tension is reached & maintained by the two compression applicators depicted.

The pawl 675 may have a certain predetermined stiffness to accommodate a predetermined level of tension. If medical personnel cranks the tensioning device too far, the locking mechanism 655B will slip back until an appropriate tension is obtained. Once reached, the mechanism 655B would reengage preventing complete loss of tension on the skin edges. This aspect may prevent tissue ischemia from over tensioning.

Figure 6T:
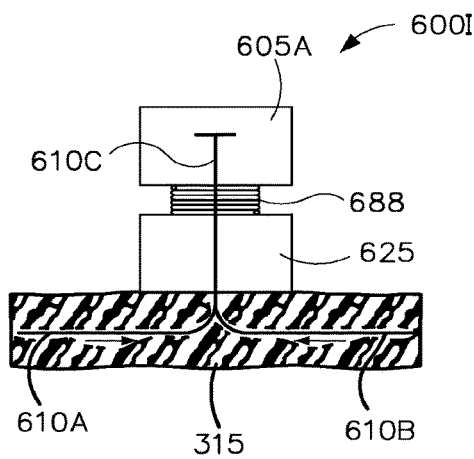
FIG. 6T is a diagram illustrating a cross-sectional view of a dressing system with a spring-biased end tensioning mechanism according to one exemplary embodiment of the invention.

FIG. 6T is a diagram illustrating a cross-sectional view of a dressing system 6001 with a spring-biased end tensioning mechanism 605A according to one exemplary embodiment of the invention. This illustration depicts a safety mechanism for preventing excessive tension by applying a constant tension provided by a spring 688 which does not allow medical personnel to alter the tension. Additionally, this tension system 6001 does not require medical personnel to serially increase the tension as the other embodiments may require. The system 6001 may constantly apply tension through the spring 688. According to this exemplary embodiment, the end tensioning mechanism 605A, which is similar to the ones described above in connection with FIGS. 6A-6C, has a spring 688 which provides a bias or expansion force against the end tensioning mechanism 605A. The spring 688 can be coupled to the longitudinal block 625 and the end tensioning mechanism 605A.

The spring 688 may be held in a compressed state by some sort of locking mechanism (not illustrated). Exemplary locking mechanisms may include, but are not limited to, hooks, wires, and the like. The dressing would arrive in a package locked without tension. Once the dressing is attached to the skin edges the tensioning mechanism may then be unlocked to allow the application of tension.

One benefit of this embodiment is that tension may be constantly applied at a known level of tension provided by the spring. There would usually be no times where there was no tension placed on the wound because medical personnel did not manually tension the device on a sequential basis. Additionally, there would be limited concern for over tensioning by medical personnel since the tension would be supplied at a constant and controlled level. This exemplary embodiment provides both safety feature as well as a measure of safety measure for tension. A spring controlled mechanism could be applied to the crank mechanism in a similar fashion.

Figure 6U:
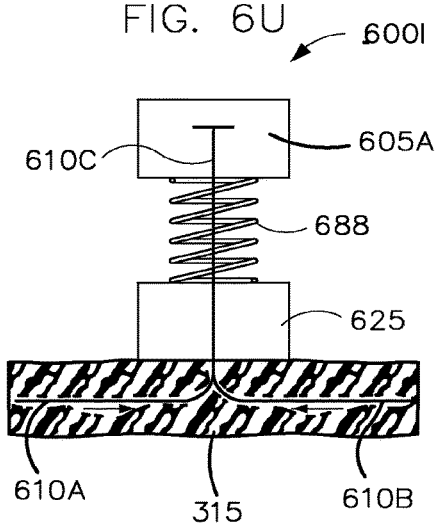
FIG. 6U is a diagram illustrating a cross-sectional view of the dressing system of FIG. 6T after further tensile forces have been applied according to one exemplary embodiment of the invention.

FIG. 6U is a diagram illustrating a cross-sectional view of the dressing system of FIG. 6T after further tensile forces have been applied according to one exemplary embodiment of the invention. In this exemplary embodiment, the spring 688 is allowed to expand so that its expansion forces can press upon the end tensioning mechanism 605A so that the end tensioning mechanism 605A is displaced or moves away from the longitudinal member 625.

This action causes section 610C of the tension device 610 to move upward and through the longitudinal member 625. This also causes the tensioning members 610A,B to contract and move upward through the longitudinal member 625. This also causes the sponge 315 to compress and/or contract.

Figure 6V:
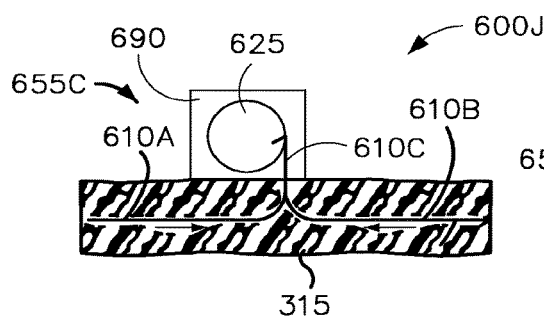
FIG. 6V is a diagram illustrating a cross-sectional view of a dressing system with another type of locking mechanism for the longitudinal member according to one exemplary embodiment of the invention

FIG. 6V is a diagram illustrating a cross-sectional view of a dressing system 600J with another type of locking mechanism 655C for the longitudinal member 625 according to one exemplary embodiment of the invention. According to this exemplary embodiment, the housing 690 of the locking mechanism 655C which contains the longitudinal member 625 on which the tensioning members 610A,B are wound may comprise a rectilinear, prismatic shape. Longitudinal member may roll backwards until a safe tension is applied and may be reset at that point. The tension may be preset by the medical pesonnel.

Specifically, the housing 690 may comprise a square or rectangular shape. However, one of ordinary skill in the art recognizes that other cross-sectional shapes for the housing 690 as well as for the longitudinal member 625 are within the scope of the invention. The portions of the locking mechanism 655C which hold the longitudinal member 625 in place after the longitudinal member 625 has been rotated are not depicted in this illustration. The portions of the locking mechanism 655C which holds the longitudinal member 625 in place may comprise the ratchet of FIG. 6S.

Figure 6W:
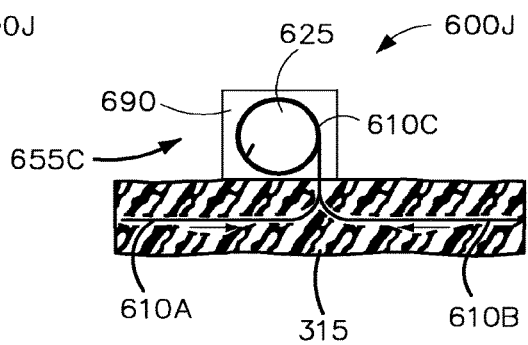
FIG. 6W is a diagram illustrating a cross-sectional view of the dressing system of FIG. 6T after further tensile forces have been applied according to one exemplary embodiment of the invention.

FIG. 6W is a diagram illustrating a cross-sectional view of the dressing system 600J of FIG. 6T after further tensile forces have been applied according to one exemplary embodiment of the invention. In this exemplary embodiment, the tensioning members 610A, B have been reeled up or further wound around the central longitudinal member 625. Section 610 C of the tensioning device 610 may form a spool comprising the reeled in tensioning members 610A, 610B, which are protected and contained by the housing 690.

Figure 6X:
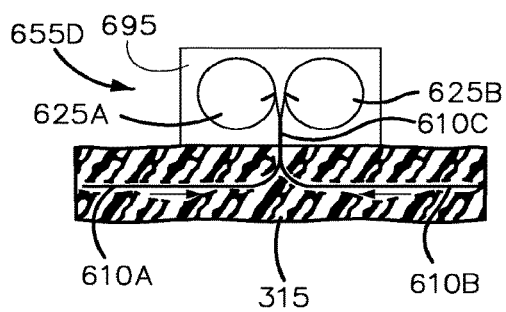
FIG. 6X is a diagram illustrating a cross-sectional view of a dressing system with another type of locking mechanism for the longitudinal member according to one exemplary embodiment of the invention.

FIG. 6X is a diagram illustrating a cross-sectional view of a dressing system 600K with another type of locking mechanism 655D for the longitudinal member 625 according to one exemplary embodiment of the invention. This exemplary embodiment employs two separate longitudinal members or cranks 625A, 625B versus one to allow for different tensions to be applied to different edges. As noted, the locking mechanism 655D of this exemplary embodiment may comprise two separate longitudinal members 625A, B that are moved by a motor. This means that one side of tensioning members 610A,B can be wound up or reeled upon a respective separate rotating longitudinal member 625 in which each member 625 is rotated by a motor. Each side could be wound independently of each other in order to allow for maximum tensioning for each side.

In other words, the first set of tensing members 610A present in one half of a sponge 315 can be reeled up and stored on a first central, longitudinal member 625A. Similarly, a second set of tensioning members 610B occupying the second half of sponge 315 can be reeled up in stored on the second central, longitudinal member 625B.

The portions of the locking mechanism 655D which hold the two longitudinal members 625A,B in place after the longitudinal members 625A,B have been rotated are not depicted in this illustration. The portions of the locking mechanism 655C which holds the longitudinal member 625 in place may comprise the ratchet of FIG. 6S. Exemplary motors may include, but are not limited to, electric motors like an AC motor that includes a synchronous motor, an induction motor, DC motors such as a brushed DC electric motor or a brushless DC motor, an electrostatic motor, a servo motor, and a pneumatic motor.

Figure 6Y:
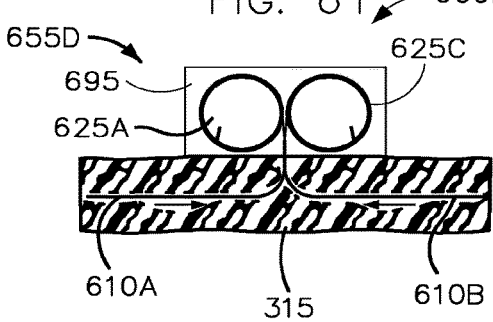
FIG. 6Y is a diagram illustrating a cross-sectional view of the dressing system of FIG. 6T after further tensile forces have been applied according to one exemplary embodiment of the invention.

FIG. 6Y is a diagram illustrating a cross-sectional view of the dressing system 600K of FIG. 6T after further tensile forces have been applied according to one exemplary embodiment of the invention. According to this exemplary embodiment, the two longitudinal members 625A, B have been further rotated by a motor relative to FIG. 6X, causing the tension members 610A,B to contract and compress or contract the sponge 315 while moving into the housing 695 around the respective rotating central longitudinal members 625A, B.

Figure 7A:
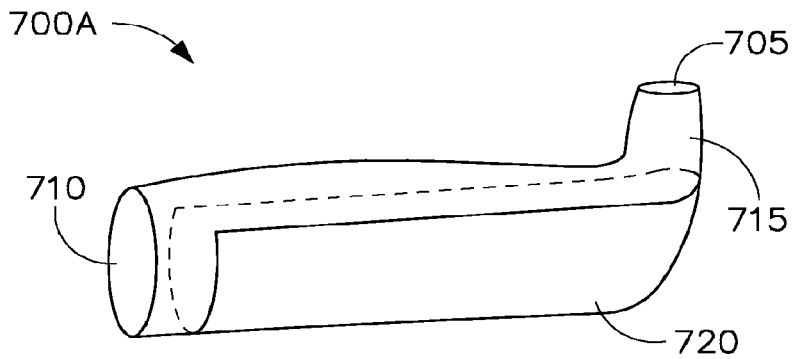
FIG. 7A is a diagram illustrating an expandable splint designed for an extremity of an animal, such as for a leg of a human, according to one exemplary embodiment of the invention.

FIG. 7A is a diagram illustrating an expandable splint 700A designed for an extremity of an animal, such as for a leg of a human, according to one exemplary embodiment of the invention. The expandable splint 700A may comprise two sections: a first inner section 715 and a second outer section 720. The inner section 715 may comprise an envelope dressing similar to the one discussed above in connection with FIG. 1A. The inner section 715 has a first end 705 and a second end 710.

According to the exemplary embodiment illustrated in FIG. 7A, the first end 705 of the inner section 715 may be smaller and its cross-sectional area relative to the second end 710. The first end 705 may be designed to receive a foot of the human body while the second end 710 is designed to receive the leg of a human body. However, one of ordinary skill in the art recognizes that the inner section 715 and outer section 720 can be sized appropriately depending upon the extremity that is injured and which requires stability from the expandable splint 700A. Other exemplary extremities include, but are not limited to, face, head, chest, abdomen, pelvis, torso, hands, forearms, and the shoulder, feet, foot to knee, and foot to groin, etc. The expandable splint 700A may replace other conventional splints such as the (arm) sugar tong, volar slab, coaptation (humerus fxs), posterior splint, cadillac, posterior splint, and knee immobilizer.

The outer section 720 may comprise an expandable bladder made from a synthetic material like plastic or rubber. The expandable splint 700A, and specifically, the outer section 720, may be inflated with a fluid such as air or with a fluid that hardens over time such as to a hardening plastic material or an epoxy. Fluids that may harden over time may be prepackaged and stored in the outer section 720.

To start the hardening process for prepackaged fluids contained within the outer section 720, a chemical reaction can be initiated by a user. In other words, the outer section 720 may store or house two fluids that are separated by a thin membrane material (not illustrated) that can be broken in order to initiate a chemical reaction to cause hardening of the fluids contained within the outer section 720. This chemical could also be injected or added in some way to begin the reaction.

Prior to any chemical reaction between the two or more fluids (not illustrated) housed in the outer section 720, the outer section 720 may be very soft and flexible for easy storage and for not providing any structural support. Alternatively, when structural support or hardening of the outer section 720 is desired, it can be filled with a fluid from an external source such as air from a pneumatic pump. The outer section 720 may be used to provide structural support and for stabilizing broken bones.

Figure 7B:
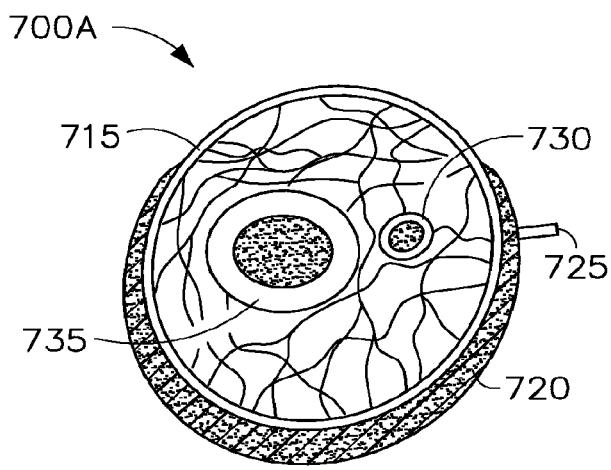
FIG. 7B is a diagram illustrating a cross-sectional view of the expandable splint illustrated in FIG. 7A according to one exemplary embodiment of the invention.

FIG. 7B is a diagram illustrating a cross-sectional view of the expandable splint 700A illustrated in FIG. 7A according to one exemplary embodiment of the invention. According to this exemplary embodiment, the outer section 720 has been expanded with a fluid such as air or fluids that may harden over time such as in a chemical reaction described above. Meanwhile, the inner section 715 comprising the envelope addressing may completely encompass or surround the extremity being treated.

In the exemplary embodiment illustrated in FIG. 7B, the extremity being treated comprises a human leg having the tibia 735 and fibula 730 bones being immobilized with the expandable splint 700A. The outer section 720 comprises a valve 725 through which the fluid is introduced into the inflatable outer section 720. The valve 725 may comprise a one-way valve said that any fluid introduced into the inflatable outer section 720 cannot exit through the valve 725.

Figure 7C:
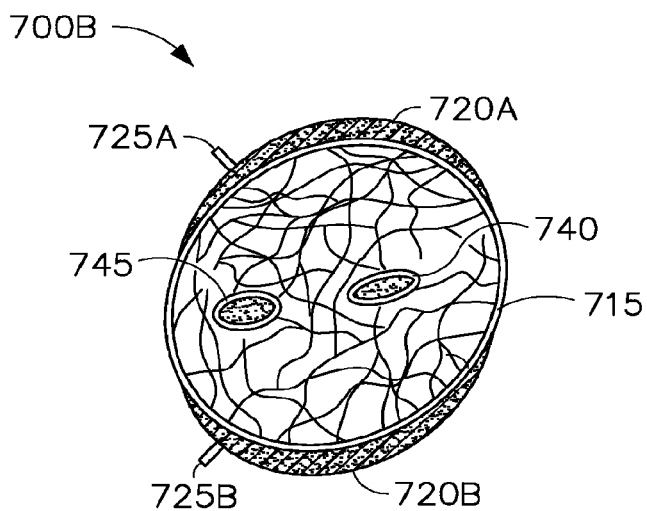
FIG. 7C is a diagram illustrating a cross-sectional view of an expandable splint for another kind of extremity, such as an arm for human, according to one exemplary embodiment of the invention.

FIG. 7C is a diagram illustrating a cross-sectional view of an expandable splint 700B for another kind of extremity, such as an arm for human having the ulna 745 and radius 740 bones immbolized, according to one exemplary embodiment of the invention. The expandable splint 700B illustrated in FIG. 7C shares several elements which are similar to those of the expandable splint 700A in FIGS. 7A-7B. Therefore, only the differences between these figures will be discussed and described in further detail below.

In the exemplary embodiment illustrated in FIG. 7C, two expandable outer section 720s along with two separate valve 725A, B are illustrated. The first outer section 720A can be positioned on one side of the extremity while the second outer section 720B can be positioned on an opposing side of the extremity. Both outer sections 720 can be inflated at the same time or they can be inflated in a sequential manner depending upon the conditions of the extremity being treated and immobilized.

Figure 8A:
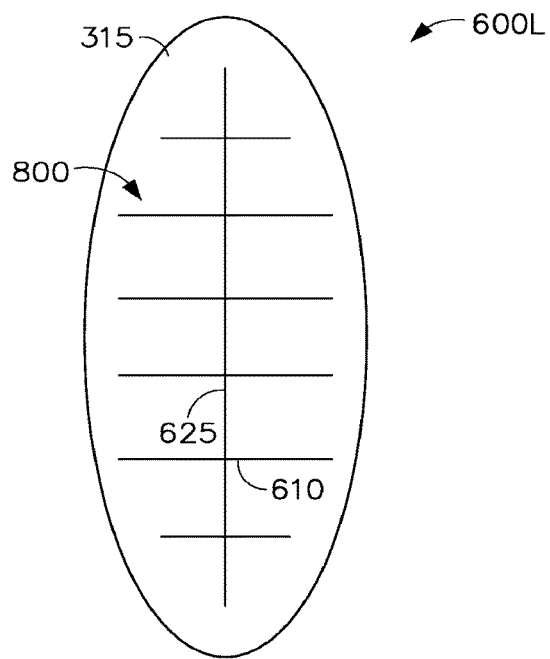
FIG. 8A is a diagram illustrating an irrigation and/or suction system for a dressing system according to one exemplary embodiment of the invention.

FIG. 8A is a diagram illustrating an irrigation and/or suction system 800 for a dressing system 600L according to one exemplary embodiment of the invention. The dressing system 600L illustrated in FIG. 8A shares several elements which are similar to those of the dressing system 600B of FIGS. 6F-6G. Therefore, only the differences between these two figures will be discussed and described in further detail below.

The tensioning members 610 of FIG. 8A are very similar to those illustrated in FIGS. 6F-6G except that the tensioning number 610 of the exemplary embodiment illustrated in FIG. 8A are generally hollow instead of being solid. Further, each tensioning member 610 may have a plurality of holes 805 for propagating a fluid. The fluid can be propagated into the sponge 315 or fluid can be removed from the sponge 315 or both depending upon the cycling of the pump 340 (see FIGS. 8B-8C).

Each tensioning member 610 can be hollow and made from a materials such as plastic. Each tensioning member 610 should be made from a material that is soft enough that will allow for trimming through the use of scissors in an operating room but that is also strong enough to support any negative pressure or vacuum without collapsing in order to remove fluid from the sponge 315 when used as a suction system.

In other words, each tensioning member 610 and the central longitudinal member 625 of the endoskeleton can support the propagation of fluid towards the sponge 315 or it may support a vacuum in which fluid can be removed from the sponge 315. Further details of the holes 805 present in each tensioning member 610 are further illustrated in FIGS. 8B-8C.

When used for irrigation, the irrigation system 800 can supply a fluid such as, but not limited to, antibiotics, enzymes, growth factors, pain medicine, anesthetics, and the like. The antibiotics can be used to treat or prevent infections for a wound covered by the sponge 315. When used for fluid removal, the suction system 800 can support a vacuum for removing exudate from the wound covered by the sponge 315 and for preventing any hematomas adjacent to the wound.

Figure 8B:
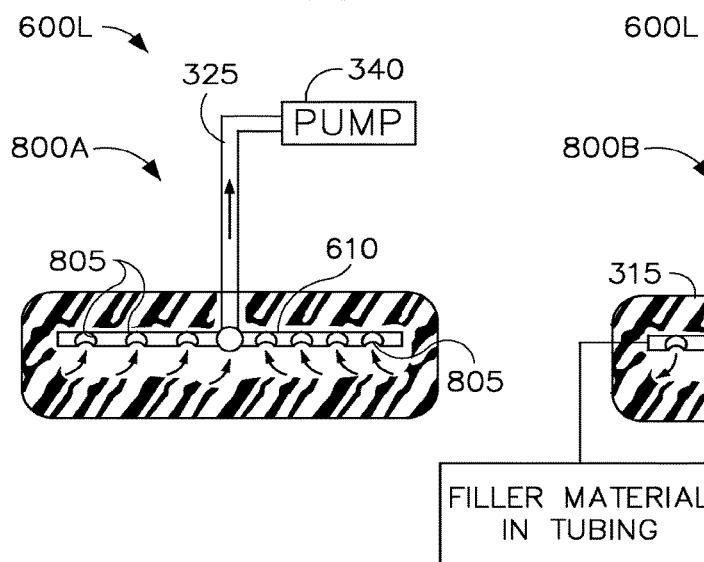
FIG. 8B is a diagram illustrating a cross-sectional view of a suction system for a dressing system according to one exemplary embodiment of the invention.

FIG. 8B is a diagram illustrating a cross-sectional view of a suction system 800A for a dressing system 600L according to one exemplary embodiment of the invention. According to this exemplary embodiment, the pump 340 creates a vacuum which is supported by the tubing 325. The tubing 325 is coupled to the hollowed tension members 610 which also have apertures or holes 805. The apertures or holes 805 can be randomly positioned over the entire surface of each hollow tension member 610.

Alternatively, the apertures or holes 805 can be uniformly distributed across each tension member 610. The holes can have diameters that range between approximately one millimeter to five millimeters. However, one of ordinary skill in the art recognizes that other ranges above or below this range are included within the scope of the invention. When a vacuum is created in the suction system 800A by the pump 340, any fluid present in the sponge 315 is sucked into the apertures or holes 805 present within each tension member 610. From each tension member 610, the fluid flows towards the pump 340 through the tubing 325.

Figure 8C:
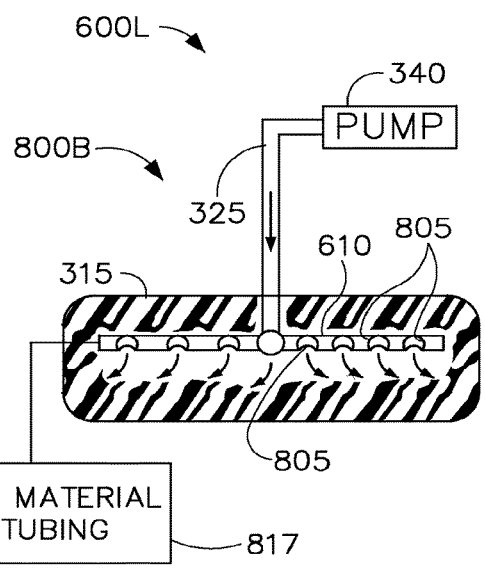
FIG. 8C is a diagram illustrating a cross-sectional view of an irrigation system for a dressing system according to one exemplary embodiment of the invention.

FIG. 8C is a diagram illustrating a cross-sectional view of an irrigation system 800B for a dressing system 600L according to one exemplary embodiment of the invention. The dressing system 600L illustrated in FIG. 8B shares several elements which are similar to those of the dressing system 600L of FIG. 8B. Therefore, only the differences between these two figures will be discussed and described in further detail below.

According to this exemplary embodiment, the pump 340 pushes a fluid through the tubing 325 and through the tension members 610 and out through the apertures or holes 805 and into the sponge 315. As noted previously, the pumped fluid may include, but is not limited to, antibiotics, enzymes, growth factors, pain medicine, anesthetics, and the like.

The tubing 325 in this exemplary embodiment could be filled with a porous material (filler material 817) such as but not limited to a sponge, microspheres, or a screen at the interface of the hole and tissue. The purpose of filling the tube 325 with filler material 817 would be to prevent or limit the ability of the soft tissue to in-grow. Additionally, if there is any sponge or micro-sphere residue, it would be significantly reduced or limited. The "filler" material would allow suction transmission or fluid injection but prevent or limit clogging and in-growth of soft tissue.

Figure 9A:
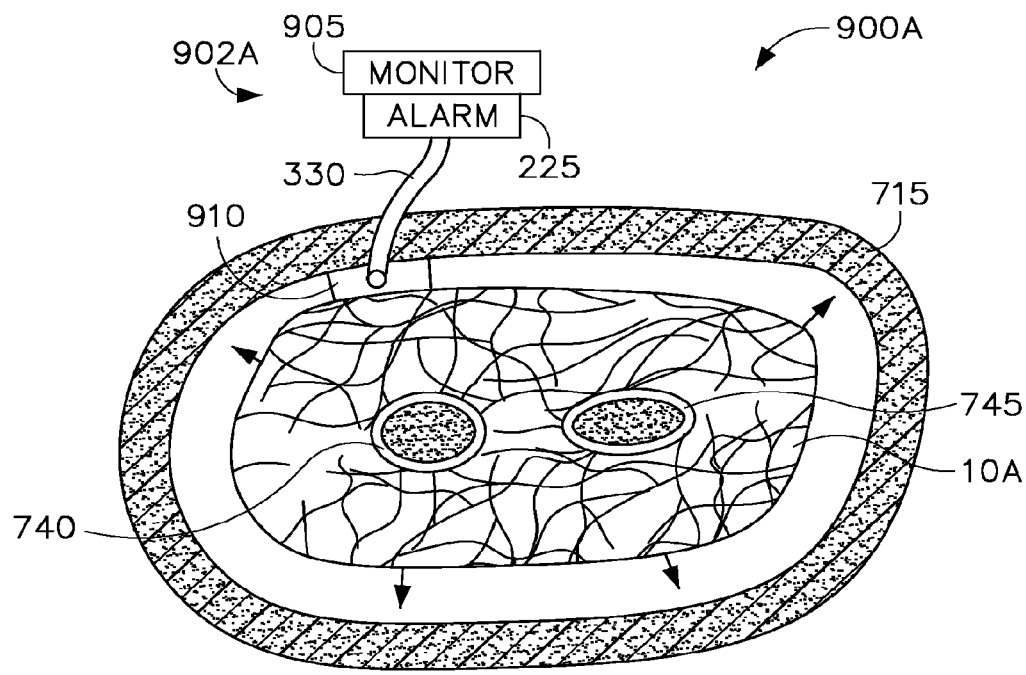
FIG. 9A is a diagram illustrating a cross-sectional view of a pressure monitor to evaluate the pressure placed on tissue by the external dressing for a dressing system according to one exemplary embodiment of the invention.

FIG. 9A is a diagram illustrating a cross-sectional view of a pressure monitor 902A to evaluate the pressure placed on tissue by the external dressing system 900A according to one exemplary embodiment of the invention. The dressing system 900A of this exemplary embodiment may comprise an envelope dressing 715, a pressure transducer 910, tubing 330, a pressure monitor 905, and an alarm 225. The envelope dressing 715 may be similar or identical to the inner section 715 of the expandable splint 700A of FIG. 7A. The pressure transducer 910 can be positioned between the envelope dressing 715 and tissue 10A. The tissue 10A may comprise an arm having a radius 740 and ulna 745 bone structures.

The pressure transducer 910 may be coupled to a computer monitor 905 through tubing 330 or wiring depending upon the type of pressure transducer 910 being employed. The pressure transducer 910 can monitor the pressure in which the external envelope dressing 715 is placing on the tissue 10A, such as an arm of a human body. The alarm 225 can be activated by the computer monitor 905 is the pressure transducer 910 measures pressure within a predetermined range. For example, if the pressure transducer 910 measures pressure of approximately 40 mmHg of diastolic pressure, the computer monitor 905 may activate the alarm 225.

An exemplary embodiment of this design would comprise a main computer that would allow for input of external devices such as an ICU monitor or sphygmomanometer, etc. This application would allow the blood pressure information to be incorporated to insure adequate perfusion pressures and blood flow.

Figure 9B:
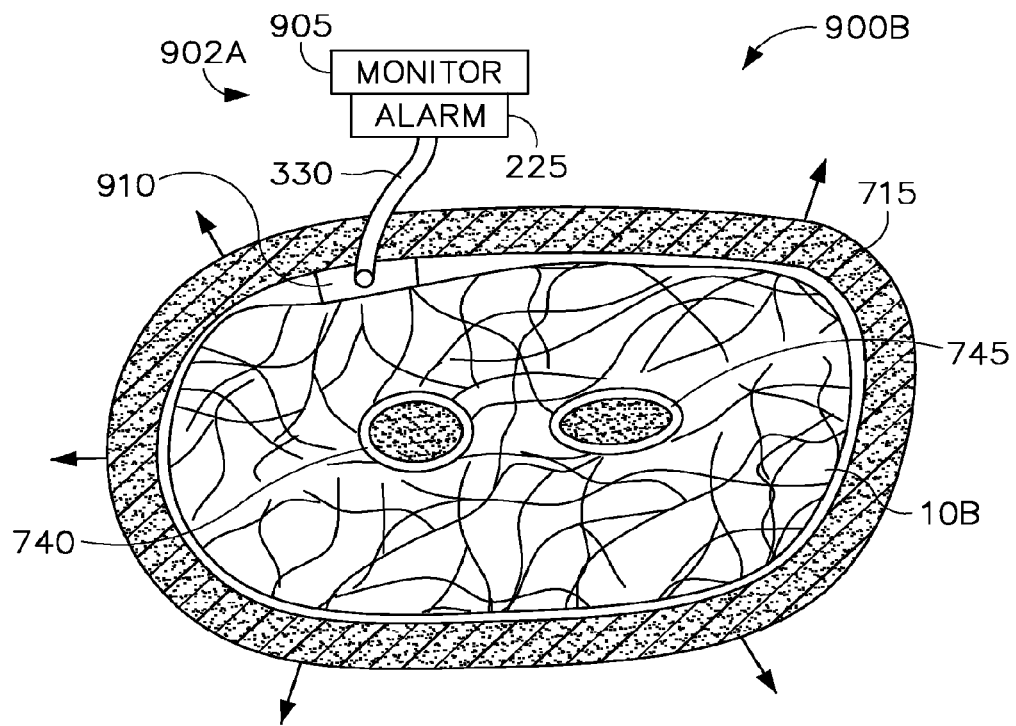
FIG. 9B is a diagram illustrating another cross-sectional view of the pressure monitor of FIG. 9A according to one exemplary embodiment of the invention.

FIG. 9B is a diagram illustrating another cross-sectional view of the pressure monitor 902A of FIG. 9A according to one exemplary embodiment of the invention. In this exemplary embodiment, the tissue 10B has become swollen and has started pressing against the envelope dressing 715 as indicated by the directional arrows adjacent to the analog dressing 715. The tissue 10B has expanded and pushed the pressure transducer 910 against the envelope dressing 715. If the pressure measured by the pressure transducer 910 reaches a predetermined value, such as 40 mm Hg of mercury, then the computer monitor 905 can activate the alarm 225 to alert medical personnel of the condition being measured.

FIG. 9C is a diagram illustrating another pressure monitor 902 for dressing systems 900B1, 900B2 according to one exemplary embodiment of the invention. The dressing systems 900B1 and 900B2 illustrated in FIG. 9C share several elements which are similar to those of the dressing system 900A-B of FIGS. 9A-9B. Therefore, only the differences between these two figures will be discussed and described in further detail below.

According to this exemplary embodiment, the pressure monitor 902B can comprise a conventional computer 345, an alarm 225, tubing 330, and a plurality of pressure transducers 910 at different site locations 915. The first dressing system 900B1 comprises an envelope dressing 715 shaped for treating an extremity such as the human arm or the torso 10C. Pressure transducers 910 can be placed at various site locations 915 throughout the envelope dressing 715 and preferably between the envelope dressing 715 and the body 10C, similar to FIG. 9A.

The second dressing system 900B2 comprises an envelope dressing 715 shaped for treating an extremity such as the human leg 10D. Pressure transducers 910 can be placed at various site locations 915 throughout the envelope dressing 715 and preferably between the envelope dressing 715 and the body 10C, similar to FIG. 9A.

FIG. 9D is a diagram illustrating the environment for an exemplary pressure transducer 910A according to one exemplary embodiment of the invention. The pressure gauge or transducer 910A can comprise anyone of a number of electronic pressure sensors. The pressure monitor 902C may detect movement or strain from the tissue 10 expanding against the gauge into the dressing 715.

Exemplary pressure transducers 910A may include, but are not limited to, piezoresistive strain types (using the piezoresistive effect of bonded or formed strain gauges to detect strain due to applied pressure), capacitive types (using a diaphragm and pressure cavity to create a variable capacitor to detect strain due to applied pressure), magnetic types (measures the displacement of a diaphragm by means of changes in inductance-reluctance, LVDT, Hall Effect, or by eddy current principal), and piezoelectric types (using the piezoelectric effect in certain materials such as quartz to measure the strain upon the sensing mechanism due to pressure).

FIG. 9E is a diagram illustrating a pressure transducer 910B for a pressure monitoring system according to one exemplary body of the invention. The pressure transducer 910A may comprise a movable member 930, a spring 925, and a stationary housing 920. The movable member 930 can be moved into the housing 920 which causes the movable member to press against the spring 925.

The spring 925 can be monitored for its displacement or change in electrical properties such as inductance when the movable member 930 compresses the spring 925 against the stationary housing 920. One of ordinary skill in the art recognizes that other types of transducers 910 besides the one illustrated in FIG. 9E are within the scope of the invention.

FIG. 9F is a diagram illustrating another pressure transducer 910C for a pressure monitoring system according to one exemplary embodiment of the invention. The pressure transducer 910C may comprise a movable button 930, a housing 935, tubing 325, and a manometer 905. The button 930 may be pushed by swollen tissue 10 into the housing 935.

The housing 935 may comprise a bladder filled with a liquid in which can be compressed by the button 930. The liquid from the bladder can flow out of the tubing 325 and into the manometer 905. Changes in the liquid levels present in the manometer 905 can indicate changes in pressure.

FIG. 9G is a diagram illustrating another pressure transducer 910D for a pressure monitoring system according to one exemplary embodiment of the invention. The pressure transducer hundred 2F may comprise a flat pad/sensor pressure gauge 940 that is coupled by wires 332 a digital monitor, such as a computer 345 as illustrated in FIG. 9C. Such flat pad/sensor pressure gauges 940 are sold under the trade name ConTacts™ by Pressure Profile Systems, Inc., of 5757 Century Boulevard, Suite 600, Los Angeles, Calif. 90045 USA.

Figure 10A:
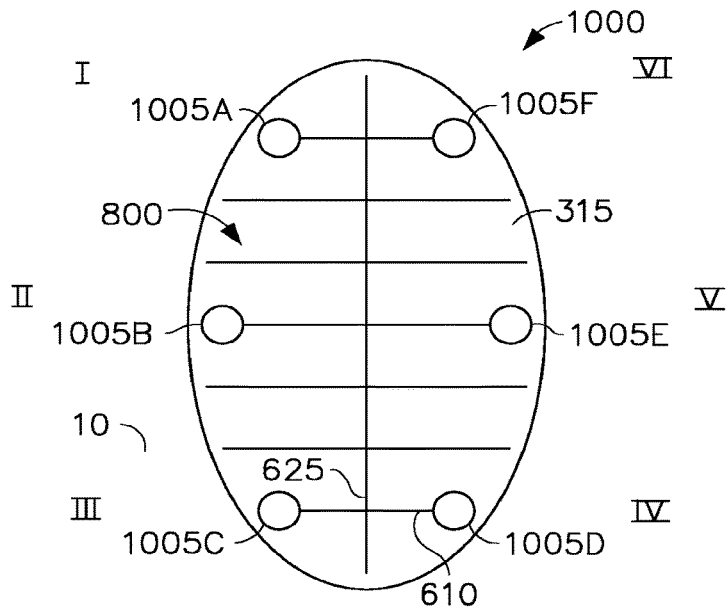
FIG. 10A is a diagram illustrating an irrigation and/or suction system with pressure gauges to monitor the negative pressure being supplied by the device for a dressing system and which are embedded within the sponge or dressing according to one exemplary embodiment of the invention.

FIG. 10A is a diagram illustrating an irrigation and/or suction system 800 with pressure gauges or transducers 910 to monitor the negative pressure being supplied by the dressing system 1000 and which are embedded within the sponge 315 of the dressing system 1000 according to one exemplary embodiment of the invention. The dressing system 1000 illustrated in FIG. 10A shares several elements which are similar to those of the dressing system 600L of FIGS. 8A-8C. Therefore, only the differences between these figures will be discussed and described in further detail below.

According to this exemplary embodiment, pressure transducers 910 are coupled to the tension members 610 which extend from the central longitudinal member 625. The pressure transducers 910 can comprise any of the ones discussed and described above in connection with FIGS. 9D-9G. While the pressure transducers 910 have been illustrated as positioned adjacent to the ends of each tension member 610, one of ordinary skill the art will appreciate that other positions on each tension member 610 are well within the scope of the invention. Further, a plurality of pressure transducers 910 may be provided on each tension member 610 depending upon the sensitivity desired for a particular application.

The pressure transducers 910 can monitor the dressing system 1000 to insure there is adequate negative pressure within the system 1000. If a leak occurs within the airtight system 1000 in which negative pressure is lost, the pressure transducers 910 can activate an alarm 225 as described in further detail below in connection with FIGS. 10B-10C.

Each pressure transducer 910 may be assigned an alphanumeric identifier that can be presented on a display (not illustrated) that may be part of the monitor 905. In this way, the monitor 905 can indicate a specific region of the dressing system 1000 that may be experiencing a leak so that medical personnel can patch a specific area of the dressing system 1000 without removing the entire dressing system 1002 to repair a leak. This embodiment will allow for isolated and targeted reinforcement of the dressings and assist medical personnel in quick management of leaks.

Figure 10B:
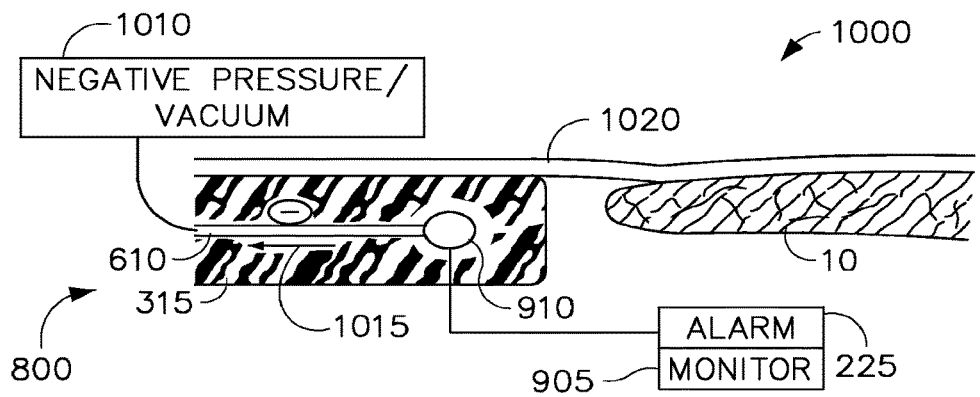
FIG. 10B is a diagram illustrating a cross-sectional view of a suction system with pressure gauges for a dressing system in a non-alarm or inactive state according to one exemplary embodiment of the invention.

FIG. 10B is a diagram illustrating a cross-sectional view of a suction system 800 with pressure gauges 910 for a dressing system 1000 in a non-alarm or inactive state according to one exemplary embodiment of the invention. The dressing system 1000 may further comprise a negative pressure/vacuum generator 1010, the pressure transducer 910, a monitor 905, an alarm 225, and an airtight cover 1020. The airtight cover 1020 can comprise materials similar to those described above in connection with the cover 305 of FIG. 3A.

The alarm 225 can comprise an audio one and/or visual one, similar to the one described above in connection with FIG. 2B. The monitor 905 may comprise a computer, a central processing unit, a hardwired circuit, and/or firmware, software, and the like. The monitor 905 can measure the negative pressure/vacuum that is created by the negative pressure/vacuum generator 1010. The negative pressure/vacuum generator 1010 may comprise a pump, similar to pump 340 of FIGS. 8A-8B. When there is no air pressure within the enclosure formed by the cover 1020, the monitor 905 will keep the alarm 225 in an inactive state.

Figure 10C:
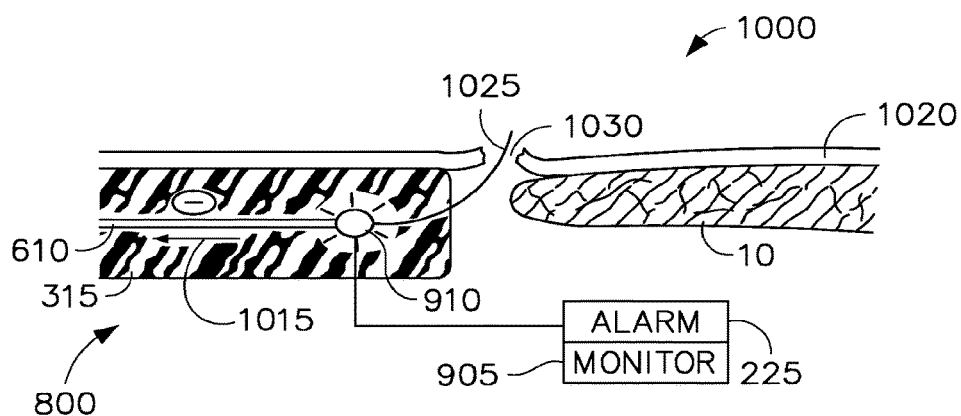
FIG. 10C is a diagram illustrating a cross-sectional view of a suction system with pressure gauges for a dressing system in an alarm state or active state according to one exemplary embodiment of the invention.

FIG. 10C is a diagram illustrating a cross-sectional view of a suction system 800 with pressure gauges 910 for a dressing system 1000 in an alarm state or active state according to one exemplary embodiment of the invention. In this exemplary embodiment, the monitor 905 has detected a decrease or change in the negative pressure/vacuum that is flowing within the tension member 610.

This decrease or change in the negative pressure/vacuum may be caused by a break 1030 in the airtight seal formed by the cover 1020. This break 1030 may permit air to flow through the break within the airtight seal of the cover 1020. Upon detecting a change in the negative pressure/vacuum, the monitor 905 may activate the alarm 225 which may comprise an audio or visual indicator (or both) in order to alert medical personnel of this change in the condition of the dressing system 1000.

Figure 11A:
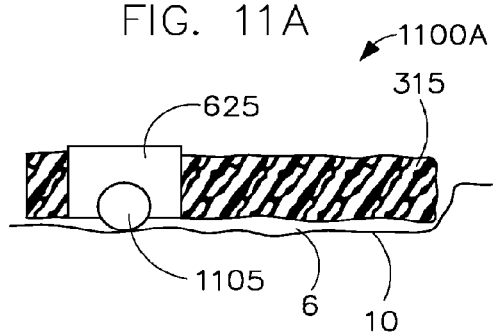
FIG. 11A is a diagram illustrating a cross-sectional view of another dressing system 1100A comprising a wound-vacuum combined with an environmental sensor and a tensioning device according to one exemplary embodiment of the invention.

FIG. 11A is a diagram illustrating a cross-sectional view of another dressing system 1100A comprising a wound-vacuum 800 combined with an environmental sensor 1105 and a tensioning device 610 according to one exemplary embodiment of the invention. The dressing system 1100 illustrated in FIG. 11A shares several elements which are similar to those of the dressing system 600A of FIGS. 6D-6E. Therefore, only the differences between these figures will be discussed and described in further detail below.

In this exemplary embodiment, the environmental sensor 1105 can be positioned within the central longitudinal member 625 of the tension device 610. The environmental sensor 1105 may comprise at least one of, but is not limited to, a pH sensor, a temperature probe/thermometer, an exudates sampling device, and/or a combination thereof.

The pH sensor may comprise an electronic instrument used to measure the pH (acidity or alkalinity) of a liquid. A typical pH sensor or meter may include a special measuring probe (a glass electrode) connected to an electronic meter that measures and displays the pH reading. The pH sensor could also comprise a NIRS device that could be used to monitor pH levels. Wireless pH sensors that are commercially available include those produced by the manufacturer of met Tronic, Inc., of Minneapolis Minn.

The thermometer may comprise an infrared thermometer, a recording thermometer, a thermistor, a thermocouple, a pill thermometer, a liquid crystal thermometer, a resistance thermometer, silicon bandgap temperature sensor, and other similar thermometers.

As illustrated in FIG. 11A, the environmental sensor 1105 may be contained within the central longitudinal member 625 while also protruding beyond the member 625 and against the tissue 10 within the wound 6. The environmental sensors 1105 may be prepackaged and positioned within predetermined locations on the tensioning device 610. Alternatively, the environmental sensors 1105 may be added individually by the clinician after or prior to application of the dressing system 1000 on a wound 6.

A monitored change in the environmental condition of tissue 10 within a wound 6, such as a change in a pH level or a change in temperature, or a combination thereof, may indicate a need for changing a dressing. One of ordinary skill in the art recognizes that clinical infections/abscesses typically change the environment of any surrounding tissue 10, such as pH levels and sometimes temperature. One of ordinary skill the art also recognizes that abscesses typically have or thrive in an acidic environment which can be monitored with a pH sensor.

Figure 11B:
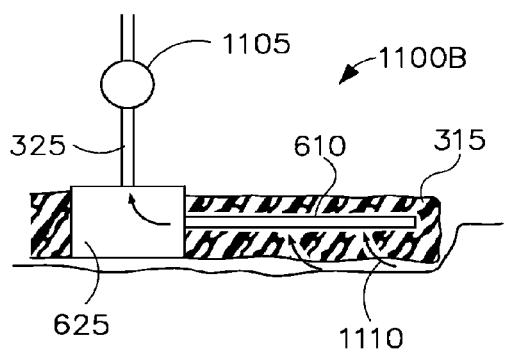
FIG. 11B is a diagram illustrating a cross-sectional view of another dressing system 1100A comprising a wound-vacuum combined with an environmental sensor and a tensioning device according to one exemplary embodiment of the invention.

FIG. 11B is a diagram illustrating a cross-sectional view of another dressing system 1100B comprising a wound-vacuum 800 and combined with an environmental sensor 1105 spaced apart from a tensioning device 610 according to one exemplary embodiment of the invention. In this exemplary embodiment, the environmental sensor 1105 is positioned away and spaced apart from the tension device 610. The environmental sensor 1105 can monitor the fluid/exudate as it is removed from the wound under any form of negative pressure combined with the hollow tension members 610.

Figure 11C:
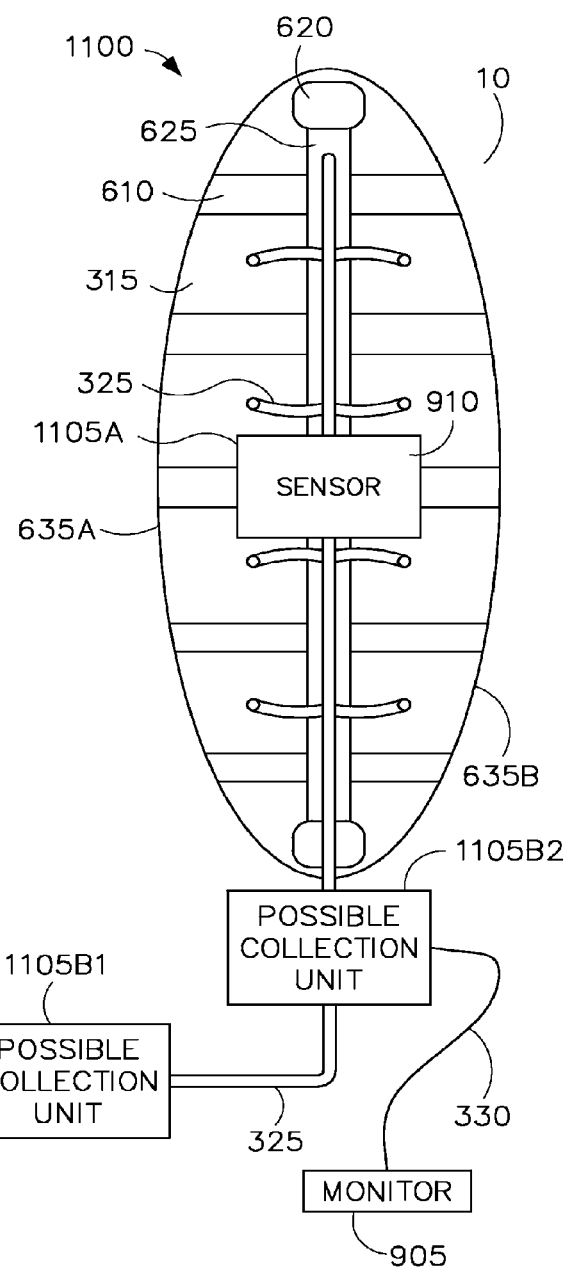
FIG. 11C is a diagram illustrating an elevation view of another dressing system 1100A comprising a wound-vacuum combined with an environmental sensor and a tensioning device according to one exemplary embodiment of the invention.

FIG. 11C is a diagram illustrating an elevation view of the dressing system 1100 comprising a wound-vacuum 800 combined with a environmental sensor 1105 and a tensioning device according to one exemplary embodiment of the invention. In this exemplary embodiment, the environmental sensor 1105 can be positioned within the central longitudinal member 625.

Alternatively, the environmental conditions within the dressing system 1100A may be monitored by taking samples from two different collection units 1105A,B in which the first collection unit 1105B1 may be positioned closer to a pump 340 relative to the dressing system 1100. Alternatively, the second potential collection unit 1105B2 may be monitored by taking samples in which the second unit 1105B2 is positioned closer to the dressing system 1000 relative to the pump 340 and the dressing system 1000. The monitor 905 may also detect other conditions other than pH levels, such as, but not limited to, bacteria, fungi, body chemicals, cytokines, growth factors, proteins, peptides, sugars, and etc.

The monitor 905 coupled to the first and second possible collection units 1105B1, 1105B2 may comprise a computer, a central processing unit, a hardwired circuit, and/or firmware, software, and the like. The pump 340 may comprise the types discussed above in connection with FIGS. 8B-8C.

In addition to or as an alternative exemplary function, the wound-vacuum system 800 may be able to distribute warm or cold water through the dressing system 1100 to promote healing of the wound 6. This means that the wound-vacuum system 800 can pump warm or cold water through the hollow central longitudinal member 625 and hollow tension members 610 and into the sponge 315. After distributing this warm or cold water, the wound-vacuum system 800 can pump and reverse in order to remove the water as well as any exudates, or any other fluid or particulate matter, that may be present within the wound and absorbed by the sponge 315.

Figure 12A:
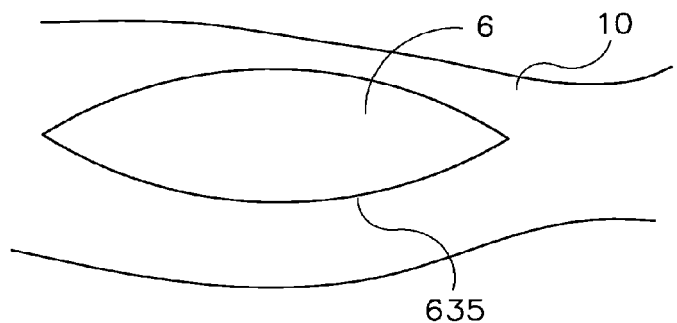
FIG. 12A is a diagram of a side view of a wound 6 that has a wound edge and which is part of the tissue that may comprise a human leg according to an exemplary embodiment of the invention.

FIG. 12A is a diagram of a side view of a wound 6 that has a wound edge 635 which is part of the tissue 10 that may comprise a human leg according to an exemplary embodiment of the invention. Within the wound 6, there could be exposed muscle tissue. The wound 6 may be formed as a result of a fasciotomy or an injury.

Figure 12B:
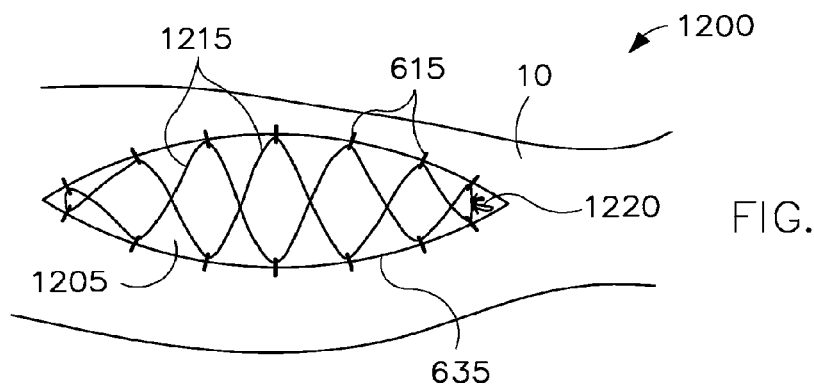
FIG. 12B is a diagram illustrating a Roman sandal or shoelace technique for closing wounds according to an exemplary embodiment of the invention.

FIG. 12B is a diagram illustrating a Roman sandal or shoelace technique for closing wounds 6 according to an exemplary embodiment of the invention. The shoelace 1215 may comprise a single cord and that is attached to skin edges by fastening mechanisms 615. The fastening mechanisms 615 may include, but are not limited to, staples, suture threads, or a combination thereof.

The shoelace 1215 may be crisscrossed over wound 6. The shoelace 1215 may be sequentially pulled to draw the skin edges 635 into a geometric central region relative to the wound 6. Fastening mechanisms 615 on opposite sides of the wound 6 are pulled closer to one another as the shoelace is tightened across the wound 6. The single chord of the shoelace 1215 may comprise materials such as, but not limited to, rubber, or plastic.

Figure 12C:
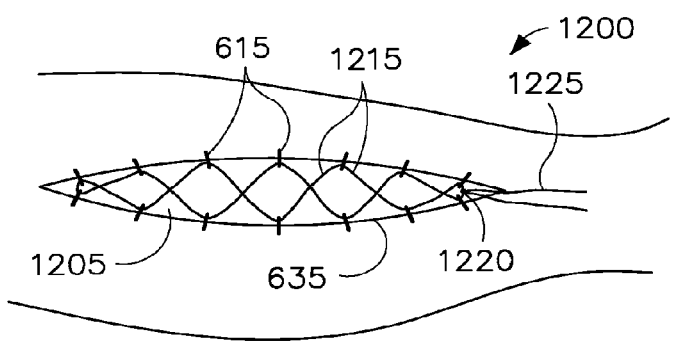
FIG. 12C is a diagram illustrating a Roman sandal or shoelace technique that has further closed the wound illustrated in FIG. 12B according to one exemplary embodiment of the invention.

FIG. 12C is a diagram illustrating a Roman sandal or shoelace technique that has further closed the wound 6 illustrated in FIG. 12B according to one exemplary embodiment of the invention. As illustrated in this exemplary embodiment, the shoelace 1215 has been drawn tighter relative to FIG. 12B.

By pulling the shoelace 1215 tighter, this action has moved opposing sides were wound edges 635 closer toward another since the fastening mechanisms 615 attached to the wound edges 635 are connected to the shoelace 1215. In this figure, the additional or excess shoelace 1215 that has been pulled through the fastening mechanisms 615 has been denoted with reference numeral 1225. The excess shoelace material 1225 that no longer has tension forces applied to it can be wrapped up or it can be removed by cutting from medical personnel.

Figure 12D:
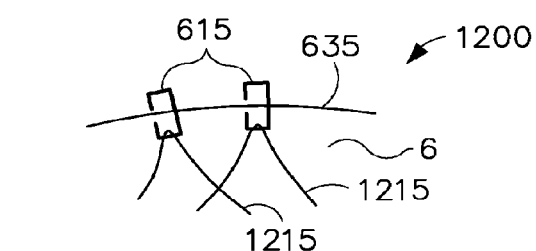
FIG. 12D is a diagram illustrating further details of the fastening mechanisms 615 for the Roman sandal or shoelace technique of FIG. 12 according to one exemplary embodiment of the invention.

FIG. 12D is a diagram illustrating further details of the fastening mechanisms 615 for the Roman sandal or shoelace technique of FIG. 12C according to one exemplary embodiment of the invention. As illustrated in this exemplary embodiment, the fastening mechanisms 615 may comprise staples. The staples may comprise materials such as, but not limited to, metal, hard plastic, and the like. For example, the staples may be made from titanium or stainless steel. Titanium usually produces less reaction with the immune system and, being non-ferrous, does not interfere significantly with MRI scanners, although some imaging artifacts may result. The staples may also comprise synthetic absorbable (bioabsorbable) materials, based on polyglycolic acid. The fastening mechanisms 615 can have one section that engages a wound edge 635 while another section engages a portion of the shoelace 1215.

FIG. 13A is a side view of a sequential compression dressing system 1300 according to one exemplary embodiment of the invention. The sequential compression dressing system 1300 may comprise a pump 340, tubing 325, an inflatable bladder 1305, and an envelope dressing 715. The system may also incorporate the wound monitoring and suction/irrigation systems, such as the system 300A of FIG. 3B that comprises a computer 345. The system 300A via computer 245 may monitor conditions such as, but not limited to, pH, NIRS values, temperature, exudate sampling, and other similar conditions. The envelope dressing 715 may comprise materials similar to those as discussed above in connection with the inner section 715 of FIG. 7 and the envelope dressing 12 of FIG. 1.

The inflatable bladder 1305 may comprise an elastic material such as rubber, plastic, vinyl, a combination thereof, and other like materials. The materials of the bladder 1305 may be sterilized or made from sterile materials in exemplary embodiments in which the bladder 1305 directly contacts tissue 10. The inflatable bladder 1305 may be filled with a fluid, such as air, or a liquid, such as water or inert fluids. The inflating and deflating of the bladder 1305 may comprise or act as a sequential compression of the tissue 10 which may promote blood flow in general, and possibly the return of blood flow towards the heart of an animal, such as a human.

This periodic inflating and deflating of the bladder 1305 may be automated by coupling a controller, such as a computer (not illustrated), to the pump 340. The sequential compression of the extremity or tissue 10 may be varied by time, rate, and magnitude of the pressure applied by the bladder 1305.

The periodic inflating and deflating of the bladder 1305 may also reduce the risk of creating any possible perfusion complications within the extremity that is in contact with the bladder 1305. This action may also prevent blood pooling and possibly prevent a blood clot forming within the extremity that is in contact with the bladder 1305. The sequential compression action may also prevent or reduce the risk of an edema forming in the compartment of the extremity or tissue 10 which is in contact with the bladder 1305.

FIG. 13B is a cross-sectional view of the sequential compression dressing system 1300 of FIG. 13A in a deflated state according to one exemplary embodiment of the invention. According to this exemplary embodiment, two bladders 1305A, 1305B are illustrated and are in a deflated state. The bladders 1305 may come in direct contact with the tissue 10 that may comprise a human leg that has a tibia bone 735 and a fibula bone 730. Alternatively, the bladders 1305 may be positioned or enclosed by the envelope dressing 715 so that they are not in direct contact with the tissue 10 so that only the envelope dressing 715 comes in direct contact with the tissue 10.

FIG. 13C is a cross-sectional view of the sequential compression dressing system 1300 of FIG. 13B in an inflated state according to one exemplary embodiment of the invention. According to this exemplary embodiment, each of the two bladders 1305A, 1305B has been inflated with a fluid such as air or another inert fluid. Each bladder 1305 may press against the tissue 10 such that the tissue 10 may move and/or deform in response to the compressive force produced by the surface of each bladder 1305.

FIG. 14A is a diagram illustrating a cross-sectional view of a first anchoring mechanism 1405 for a tension member 610A of a tensioning device 1400A according to one exemplary embodiment of the invention. The tensioning device 1400A illustrated in FIG. 14A shares several elements which are similar to those of the tensioning device 610 of FIGS. 6A-6E. Therefore, only the differences between these figures will be discussed and described in further detail below.

The tensioning device 1400A may comprise a tension member 610A and an anchoring mechanism 1405. The anchoring mechanism 1405 may comprise a section of the tension member 610A that is positioned in an approximately perpendicular manner relative to a main portion of the tension member 610A. This anchoring mechanism 1405 may comprise a material that is similar to the material of the tension member 610A and it may be uniform with or made in conjunction with the tension member 610A. In other words, the first anchoring mechanism 1405 may be formed integrally with the tension member 610A.

The anchoring mechanism 1405 may increase the surface area that the tension member 610A has in contact with the sponge 315 such that the anchoring mechanism 1405 may pull the sponge 315 when the tension member 610A is contracted as discussed above in connection with FIG. 6. While only a single anchoring mechanism 1405 is illustrated, one of ordinary skill the art recognizes that a plurality of anchoring mechanism 1405 can be disposed upon a length of the tension member 610A and such an exemplary embodiment would be included within the scope of the invention.

FIG. 14B is a diagram illustrating a cross-sectional view of a second anchoring mechanism 1410 for a tension member 610B of a tensioning device 1400B according to one exemplary embodiment of the invention. The tensioning device 1400B illustrated in FIG. 14B shares several elements which are similar to those of the tensioning device 610 of FIGS. 6A-6E. Therefore, only the differences between these figures will be discussed and described in further detail below.

According to this exemplary embodiment, the second anchoring mechanism 1410 may comprise a lattice of linear members that are coupled to an end of a tension member 610B. The lattice of linear members may comprise elements made of similar materials relative to the tension member 610B but which may have a substantially smaller diameter relative to a diameter of the tension member 610B. The anchoring mechanism 1410 may be attached to the tension member 610B by a fastening mechanism such as a plastic weld. Alternatively, the second anchoring mechanism 1405 may be formed integrally with the tension member 610B.

The anchoring mechanism 1410 may provide a secure attachment to the tension member 610B as well as to the sponge 315. While the second anchoring mechanism 1410 may be strong enough to withhold and to move in conjunction with the tension forces applied by the tension member 610B, the respective diameters of the members forming the second anchoring mechanism 1410 may be small enough so that they can be easily trimmed or cut by medical personnel in order to properly size and/or shape the sponge for a wound 6 having a specific or particular shape/geometry.

FIG. 14C is a diagram illustrating a cross-sectional view of a third anchoring mechanism 1415 for a tension member 610C of a tensioning device 1400C according to one exemplary embodiment of the invention. The tensioning device 1400C illustrated in FIG. 14C shares several elements which are similar to those of the tensioning device 610 of FIGS. 6A-6E. Therefore, only the differences between these figures will be discussed and described in further detail below.

According to this exemplary embodiment illustrated in FIG. 14 C, the third anchoring mechanism 1415 may comprise a plurality of barbs or bulged portions having increased and variable sized cross-sectional areas along the length of the tension member 610C. The anchoring mechanism 1415 may increase an amount of surface area of the tension member 610C that is in contact with the sponge 315 so that the tension member 610 C may contract the sponge 315 when tension forces are applied to the tension member 610C. The third anchoring mechanism 1415 may be formed integrally with the tension member 610C.

FIG. 14D is a diagram illustrating a cross-sectional view of a fourth anchoring mechanism 1420 for a tension member 610D of a tensioning device 1400D according to one exemplary embodiment of the invention. The tensioning device 1400D illustrated in FIG. 14D shares several elements which are similar to those of the tensioning device 610 of FIGS. 6A-6E. Therefore, only the differences between these figures will be discussed and described in further detail below.

According to this exemplary embodiment illustrated in FIG. 14D, the fourth anchoring mechanism 1420 may comprise a plurality of angled within barbs or spikes that grasp of the sponge 315. The fourth anchoring mechanism 1420 may be formed integrally with the tension member 610D. The invention is not limited to the angles for the barbs or spikes illustrated in FIG. 14D. One of ordinary skill the art recognizes that other angles for the barbs or spikes along the tension member 610D are within the scope of the invention.

FIG. 15A is a diagram illustrating an elevation view of a dressing system 600M with the tensioning device 610 according to one exemplary embodiment of the invention. The dressing system 600M illustrated in FIG. 15A shares several elements which are similar to those of the dressing system 600B in FIGS. 6F-6I. Therefore, only the differences between these figures will be discussed and described in further detail below.

According to this exemplary embodiment illustrated in FIG. 15A, the sponge 315 may comprise a circular or elliptical shape. To appropriately grasp and compress the circularly shaped sponge 315, the tension members 610 may extend in a radial manner relative to a geometric center of the circularly shaped sponge 315.

In this exemplary embodiment, the end tensioning device 605A in addition to the central member 625 may both comprise a circular or annular shape which corresponds with the circular shape of the sponge 315.

FIG. 15B is a diagram illustrating cross-sectional view of the dressing system with the tensioning device of FIG. 15A according to one exemplary embodiment of the invention. As noted previously, the central member 625 of the tensioning device 610 may comprise a circular shape. Similarly, the end tensioning device 605A may also comprise a circular shape to correspond with the circular shaped sponge 315. The tensioning device 610 may comprise radial tension members 610A and 610B.

FIG. 15C is a diagram illustrating an elevation view of a dressing system 600N with the tensioning device 610 according to one exemplary embodiment of the invention. The dressing system 600N illustrated in FIG. 15C shares several elements which are similar to those of the dressing system 600B in FIGS. 6L-6M. Therefore, only the differences between these figures will be discussed and described in further detail below.

According to this exemplary embodiment illustrated in FIG. 15C, the radial extended tension members 610 can be coupled to the edge of a wound through fastening mechanisms 615. As noted previously, the fastening mechanisms 615 may comprise elements such as staples or suture threads or any combination thereof.

FIG. 15D is a diagram illustrating an elevation view of the dressing system 600N of FIG. 15C with the end tensioning device 605A in an extended position according to one exemplary embodiment of the invention. In this exemplary embodiment, the end tensioning device 605A has been displaced or moved relative to the stationary central member 625.

This causes the tension members 610 to be moved through the central member 625 and in a direction that corresponds with the end tensioning device 605A. This action and movement of the radial tension members 610 through the circularly shaped central member 625 causes the sponge 315 to compress as illustrated in FIG. 15E discussed below.

FIG. 15E is a diagram illustrating cross-sectional view of the dressing systems 600M, N of FIGS. 15A and 15C in a compressed state according to one exemplary embodiment of the invention. In this exemplary embodiment, the radial tension members 610 have been retracted and pulled through the central member 625. The radial tension member 610 are coupled to the end tensioning device 605A which has been moved or displaced relative to the stationary circular central member 625. This movement and action of the radial tension members 610 causes the sponge 315 to compress or contract.

Figure 16A:
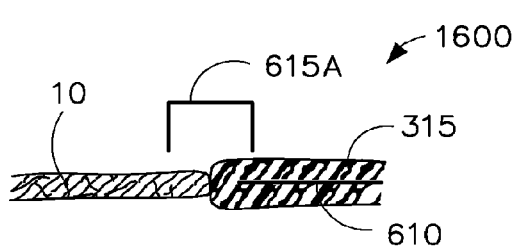
FIGS. 16A-C are diagrams illustrating the sequence of steps that may be employed to secure a fastening mechanisms to tissue and a combination of a tension member and a sponge 315.
Figure 16B:
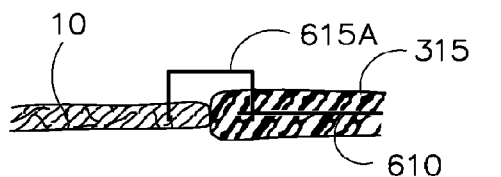
Figure 16C:
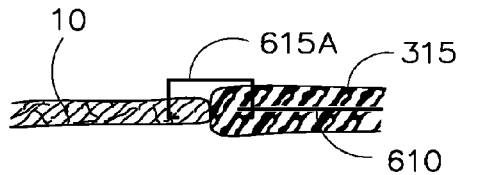

FIGS. 16A-C are diagrams illustrating the sequence of steps that may be employed to secure fastening mechanisms 615A to tissue 10 and a combination of a tension member 610 and a sponge 315 according to one exemplary embodiment of the invention. FIG. 16A illustrates a fastening mechanism 615A comprising a staple positioned above tissue 10 and a sponge 315 that includes a tension member 610.

The attachment of the fastening mechanism 615A to the tissue 10 and sponge 315 will usually be performed by medical personnel and preferably in a sterile environment, such as in a surgical operating room. Each fastening mechanism 615A comprising a staple may be made of a material such as, but not limited to, metal, plastic, or a biodegradable material similar to the material used in suture threads.

FIG. 16B is a diagram illustrating the fastening mechanism 615A comprising a staple that is penetrating both the tissue 10 in the sponge 315 as well as the tensioning member 610. FIG. 16C is a diagram illustrating the fastening mechanism 615A comprising of a staple that has penetrated the tissue 10, sponge 315, and tensioning member 610 and which has been bent slightly under these elements to provide a fuller connection between the fastening mechanism 615A and these elements. In this way, when the tensioning member 610 is retracted or contracted, it will pool the tissue 10 in close contact with the sponge 315 as the sponge 315 contracts with the tensioning member 610.

Figure 17A:
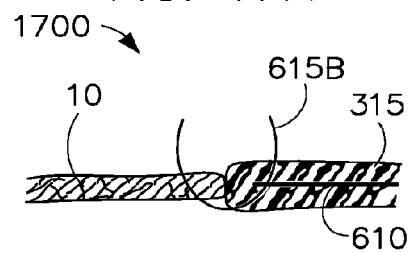
FIGS. 17A-C are diagrams illustrating the sequence of steps that may be employed to secure alternate fastening mechanisms to tissue and a combination of a tension member and a sponge according to one exemplary embodiment of the invention.
Figure 17B:
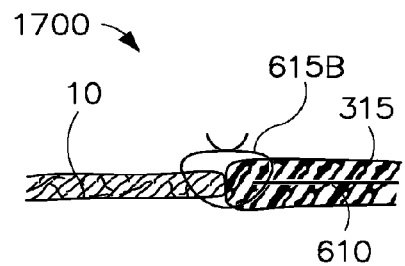
Figure 17C:
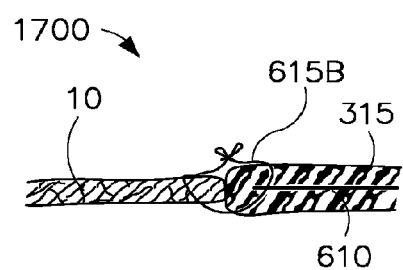

FIGS. 17A-C are diagrams illustrating the sequence of steps that may be employed to secure alternate fastening mechanisms 615B to tissue 10 and a combination of a tension member 610 and a sponge 315 according to one exemplary embodiment of the invention. According to this exemplary embodiment, the fastening mechanisms 615 may comprise suture thread.

The suture thread may be made from numerous materials, such as from biological materials. The suture threads may comprise synthetic materials, including absorbables like polyglycolic acid, polylactic acid, and polydioxanone as well as the non-absorbables nylon and polypropylene, and caprolactone. The suture threads may be coated with antimicrobial substances to reduce the chances of wound infection. The suture threads may have standard sizes and may be either absorbable (naturally biodegradable in the body) or non-absorbable. The suture threads usually must be strong enough to hold tissue securely but flexible enough to be knotted. They generally under most circumstances must be hypoallergenic and avoid any "wick effects" that may allow fluids and thus infection to penetrate the body along the suture thread tract.

FIG. 17A is a diagram illustrating the fastening mechanism 615B comprising suture thread to penetrate through tissue 10 and both the sponge 315 and the tension member 610. A needle (not illustrated) may be used to push and pull the suture thread through the tissue 10, the sponge 315, and the tension member 610.

FIG. 17B is a diagram illustrating the fastening mechanism comprising suture thread that is knotted onto itself.

Preferred, yet exemplary knots, for the suture thread may comprise a figure eight stitch and a horizontal mattress stitch. However, one of ordinary skill the art recognizes that other stitches not particularly identified are included within the scope of the invention. Meanwhile, an ordinary simple not has been illustrated in each of the figures.

FIG. 17C is a diagram illustrating the fastening mechanism 615B in a fully knotted state and for receiving any tension forces that could be exerted by the tensioning member 610. The suture thread should have enough tensile strength to withstand any tensile forces applied by the dancing member 610 in order to slowly pool besides of a wound together in order to promote healing as discussed and described above.

Figure 18A:
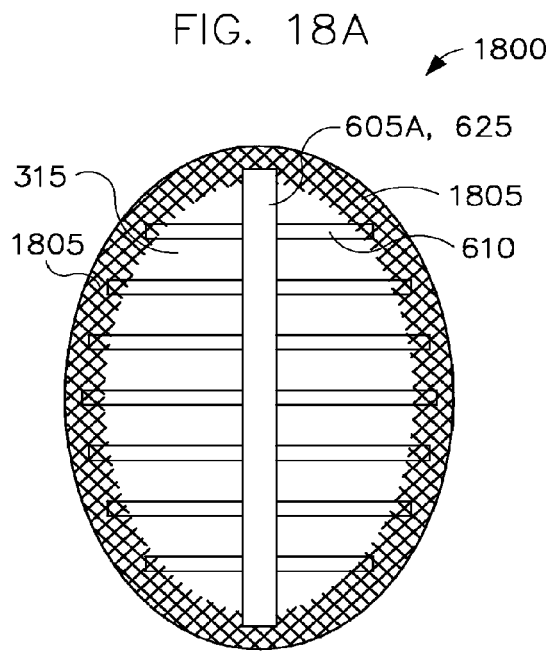
FIG. 18A is a diagram illustrating an elevation view of a dressing system with the tensioning device of FIGS. 6A-6C and a reinforced anchoring system/periphery according to one exemplary embodiment of the invention.

FIG. 18A is a diagram illustrating an elevation view of a dressing system 1800 with the tensioning device of FIGS. 6A-6C and anchoring system 1805 according to one exemplary embodiment of the invention. The dressing system 1800 illustrated in FIG. 18A shares several elements which are similar to those of the dressing system 600B in FIGS. 6F-6I and the anchoring system 1405 of FIG. 14B. Therefore, only the differences between these figures will be discussed and described in further detail below.

In FIG. 18A, the sponge 315 has an oval or a elliptical shape and has a corresponding tensioning device 610 with tensioning members 610 A,B and a central longitudinal member 625 along with an end tensioning device 605A. At an outer edge or circumference of the sponge 315, an anchoring mechanism 1805 may be provided. This anchoring system 1805 may comprise a lattice structure that is similar to the anchoring system 1405 of FIG. 14B. One advantage of the anchoring mechanism 1805 comprising the lattice structure is that it allows medical personnel to trim and customize a shape of the sponge 315 and corresponding tension member 610. Additionally, a perimeter of reinforced anchoring system would allow for anchoring to the skin in any area versus having to anchor the skin to the rib areas only.

Figure 18B:
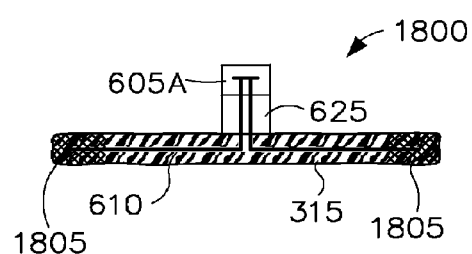
FIG. 18B is a diagram illustrating cross-sectional view of the dressing system of FIG. 18A according to one exemplary embodiment of the invention.

FIG. 18B is a diagram illustrating cross-sectional view of the dressing system of FIG. 18A according to one exemplary embodiment of the invention. The anchoring system 1805 may attach to the sponge 315 as well as the tensioning members 610. The anchoring system 1805 may be made of materials strong enough to withstand the tensile forces applied by the tensioning member 610 while also being pliable or malleable to be cut by medical personnel so that the sponge 315 and its corresponding tension member 610 can be customized with respect to shape.

Figure 19:
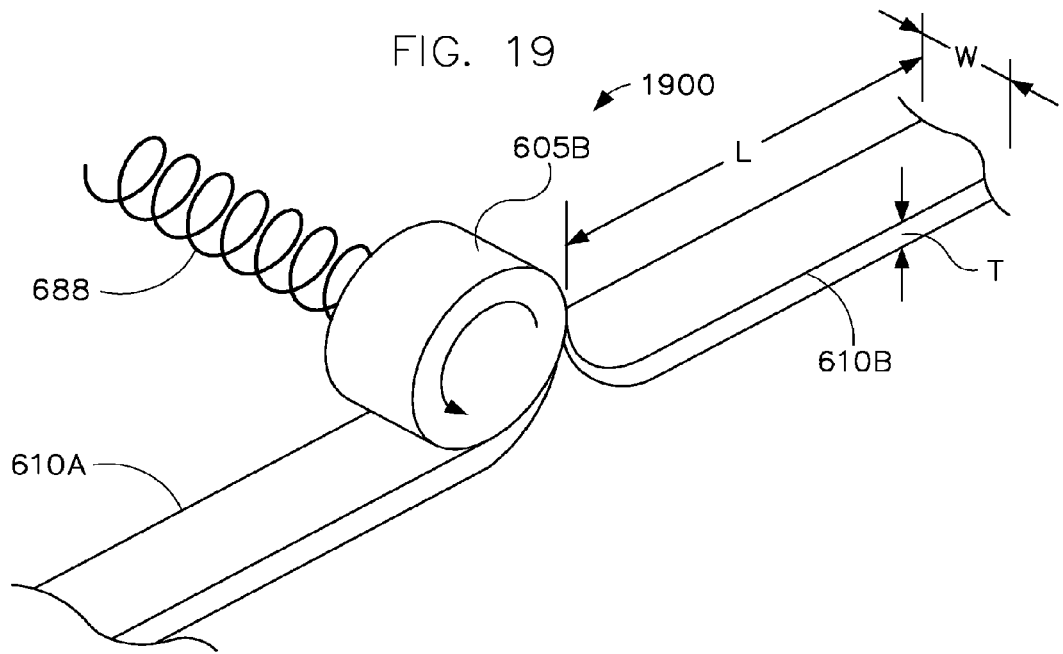
FIG. 19 is a diagram illustrating a perspective view of a tensioning device of a dressing system comprising two tensioning members which may be wound around a central longitudinal member according to one exemplary embodiment of the invention.

FIG. 19 is a diagram illustrating a perspective view of a tensioning device 610 of a dressing system 1900 comprising two tensioning members 610A, 610B which may be wound around a central longitudinal member 625 according to one exemplary embodiment of the invention. Each tensioning member 610 may comprise a planar-like structure in which the length dimension L may be substantially greater than the width dimension W. Similarly, the width dimension W may be substantially greater than the thickness dimension T. Each tensioning member 610 may comprise a material which is both strong yet flexible to permit the tensioning member 610 to wind around the central longitudinal member 625.

According to the exemplary embodiment illustrated in FIG. 19, both the first and second tension members 610A,B may be wound around the central longitudinal member 625 in a counterclockwise direction when tensile forces are desired to be applied to a corresponding sponge 315 (not illustrated). The central longitudinal member 625 may be biased by a spring 688 such that the central longitudinal member 625 constantly applies a tensile force to each tensioning member 610 by winding or rotating the central longitudinal member 625. A continual tensioning device would prevent the need for clinicians to sequentially tension the device while also eliminating the chance that the clinician over tensions the system causing perfusion problems.

Figure 20A:
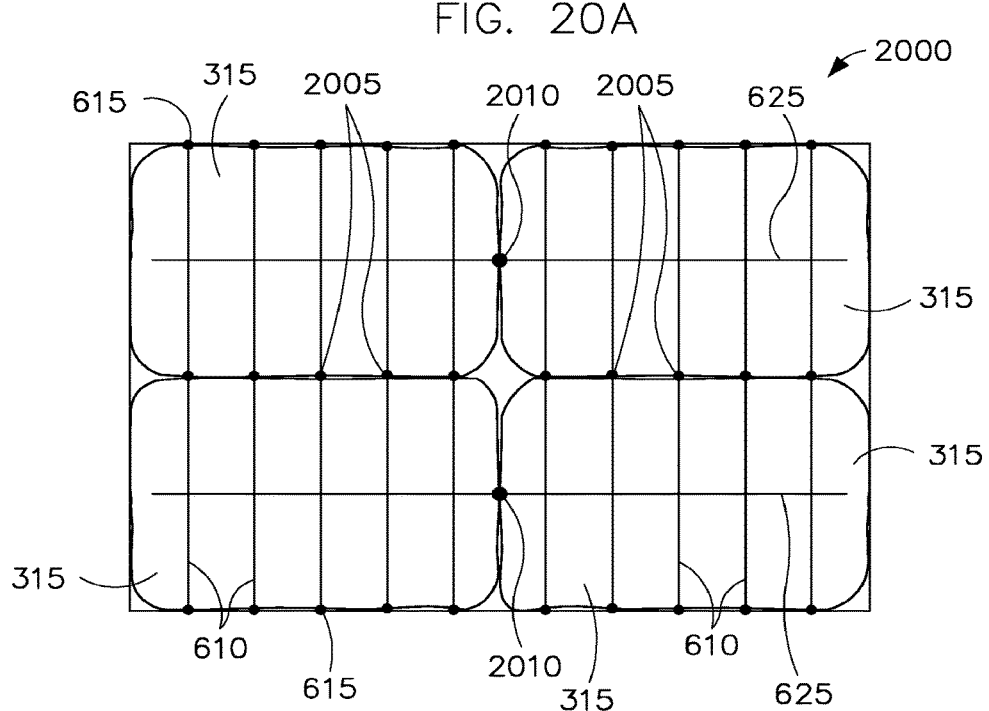
FIG. 20A is a diagram illustrating an elevation view of a system for attaching multiple dressings together in order to manage larger wounds according to one exemplary embodiment of the invention.

FIG. 20A is a diagram illustrating an elevation view of a system 2000 for attaching multiple dressings together according to one exemplary embodiment of the invention. The dressings in FIG. 20A share several elements which are similar to those of the dressing systems 600B in FIGS. 6F-6I. Therefore, only the differences between these figures will be discussed and described in further detail below.

The system 2000 provides at least two different coupling mechanisms 2005, 2010 for linking or connecting several different dressings to one another. In the exemplary embodiment illustrated in FIG. 20A, four separate substantially rectangular dressings that include four separate sponges 315 have been coupled together using the coupling mechanisms 2005, 2010.

Figure 20B:
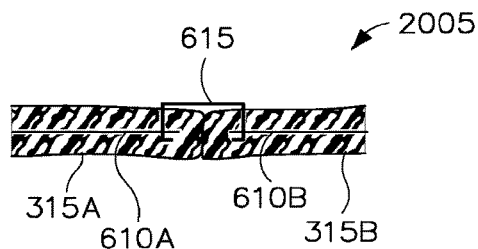
FIG. 20B is a diagram illustrating a cross-sectional view of a first dressing-to-dressing coupling mechanism according to one exemplary embodiment of the invention.
Figure 20C:
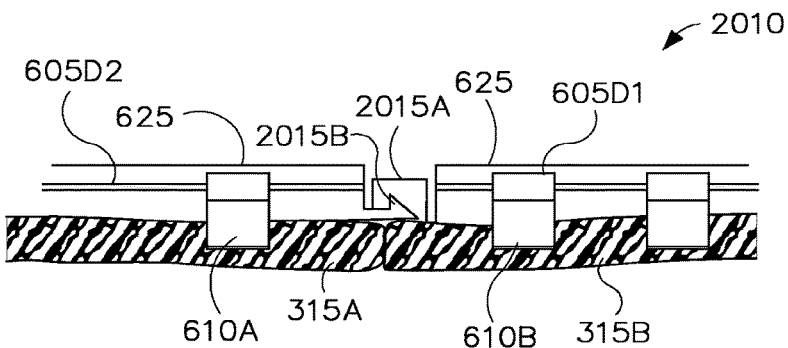
FIG. 20C is a diagram illustrating a cross-sectional view of a second dressing-to-dressing coupling mechanism according to one exemplary embodiment of the invention.

The system 2000 may be ideal for those situations in which a wound 6 is significantly large and which may far exceed the average or standard sized dressing system that has a tensioning device. Further details of the exemplary coupling mechanisms 2005, 2010 are illustrated in FIG. 20B and FIG. 20C and are described in further detail below. By placing the dressings in series, the tensioning mechanism will continue to pull one side towards the other. The tensioning arms can be connected through similar means as the skin using staples or suture or a specific fastening/linking device.

FIG. 20B is a diagram illustrating a cross-sectional view of a first dressing-to-dressing coupling mechanism according to one exemplary embodiment of the invention. In this exemplary embodiment, the first coupling mechanism 2005 may comprise one of the fastening mechanisms 615 described above. Specifically, the fastening mechanism 615 may comprise a staple or a suture thread as discussed above. This first coupling mechanism 2005 may be employed for connecting lateral sides of sponges 315 together in which the lateral sides are parallel to the central longitudinal member 625. The fastening mechanisms 615 can be used to couple one tensioning member 610 of a first dressing to a second tensioning member of a second dressing.

FIG. 20C is a diagram illustrating a cross-sectional view of a second dressing-to-dressing coupling mechanism 2010 according to one exemplary embodiment of the invention. According to this exemplary embodiment, the second coupling mechanism 2010 may comprise a hook system between respective central longitudinal members 625 of at least two different dressings. A first dressing may have a central longitudinal member 625 with a first hook 2015A while a second dressing may have a central longitudinal member 625 with a second hook 2015B.

Each hook 2015 may have a geometrical shape that is opposite to another respective hook 2015 of another dressing. In other words, a single dressing may be provided with a central longitudinal member 625 having mirrored opposite geometrical shapes for its two hooks at the end of the central longitudinal member 625 so that respective dressings may be aligned so that their respective hooks 2015 can be mated with one another. These linking devices can be made pre-installed or come in the package to be attached only if needed.

While hooks 625 have been illustrated as one exemplary coupling mechanism 2010, other types of coupling mechanisms 2010 not particularly described are included within the scope of the invention. For example, other coupling mechanisms 2010 may include, but are not limited to, clasps that have members which open and close, buttons, zippers, wedge anchors, and other like coupling mechanisms.

FIG. 21 is a diagram illustrating a cross-sectional view of a shell system 2100 for covering and protecting a dressing system and allow for an airtight seal according to one exemplary embodiment of the invention. The shell system 2100 may comprise a dressing with a tensioning device 610 and a sponge 315, a shell 320, and an adhesive 305. The materials and parts of the system 2100 may be similar to those illustrated in FIG. 3A and FIGS. 6V-6W. Therefore, only the differences between these figures will be described below.

According to this exemplary embodiment of FIG. 21, the shell 320 may form an air-tight seal over the dressing that comprises the tensioning device 610 and sponge 315. The adhesive 305 may hold the shell 320 over the dressing. The shell 320 can comprise a solid material such as plastic or rubber, or even metal as noted previously. All of the elements of the dressing may be encompassed or encased within the shell 320, such as any wires 330 or tubing 325 (not illustrated in this Figure) and which may be part of a wound-vacuum system 800 that is also part of the dressing. By covering the internal mechanisms by an external shell, the device can be made to be airtight to prevent any air leaks.

FIG. 22A is a diagram illustrating a cross-sectional view of a suction device 2200 that may be used without a sponge for a wound 6 according to one exemplary embodiment of the invention. In this exemplary embodiment, the suction device 2200 may comprise tubing 325 that has an outer diameter 2220 and an inner diameter 2225. A plurality of the holes or apertures 2205 may be present in the outer diameter 2225. These holes 2205 may be part of channels 2215 that lead to the inner diameter 2205 of the main tube.

The tubing 325 in this embodiment could be filled (filler material 817) with a porous material such as but not limited to a sponge, microspheres, or a screen at the interface of the hole and tissue. The purpose of filling the tube 325 with filler material 817 would be to prevent or limit the ability of the soft tissue to in-grow. Additionally, if there is any sponge or micro-sphere residue, it would be significantly reduced or limited. The "filler" material would allow suction transmission or fluid injection but prevent or limit clogging and in-growth of soft tissue.

The tubing 325 can be designed such that a section that does not face a wound 6 also does not have any apertures 2205 or channels 2215. Conversely, any section which does face a wound 6 will have holes 2205 and channels 2215. In this way, an air-tight seal may be formed over a wound 6 when a cover 2207 such as a bandage is placed over the tubing 325.

As noted previously, tubing 325 can be made from a range of polymers, and may include, but is not limited to silicone rubber latex and thermoplastic elastomers. Silicone may be one of the most common choices because it is inert and unreactive to body fluids and a range of medical fluids with which it might come into contact. Other materials may include, but are not limited to, plastic and hard rubbers, or a combination thereof.

FIG. 22B is a diagram illustrating a cross-sectional view of the suction device 2200 of FIG. 22A without the wound environment according to one exemplary embodiment of the invention. In this exemplary embodiment, the inner diameter 2225 of the main channel that couples with the smaller channels 2215 that extend to the outer diameter 2220 can easily be seen.

FIG. 23 is a diagram illustrating a side view of the suction device 2200 of FIG. 22 according to one exemplary embodiment of the invention. According to this exemplary embodiment, the suction device 2200 comprises a long cylindrical tube having a plurality of holes or apertures 2205 that form entrances to channels 2215 that lead to the main channel having the inner diameter 2225.

FIGS. 24A-24E are diagrams illustrating a tubing system 2400 going from an expanded state to a compressed state according to exemplary embodiments of the invention. The materials and parts of the tubing system 2400 may be similar to those illustrated in FIG. 23. Therefore, only the differences between these figures will be described below.

While the individual holes or apertures 2205 and each tube 325 have not been illustrated, these holes 2205 are present but have not been illustrated for the sake of a simple description and illustration. In this exemplary embodiment, the tubing 325 may extend in a radial fashion so that the tubing 325 extends in a substantially linear manner. Further, in this exemplary embodiment, the tubing system 2400 may further comprise a central, planar disc 2405 that is attached to a top surface of each one of the tubes 325. The central disc 2405 may be attached to each one of the two through 25 by a fastening mechanism such as an adhesive or a plastic weld.

Figure 24A:
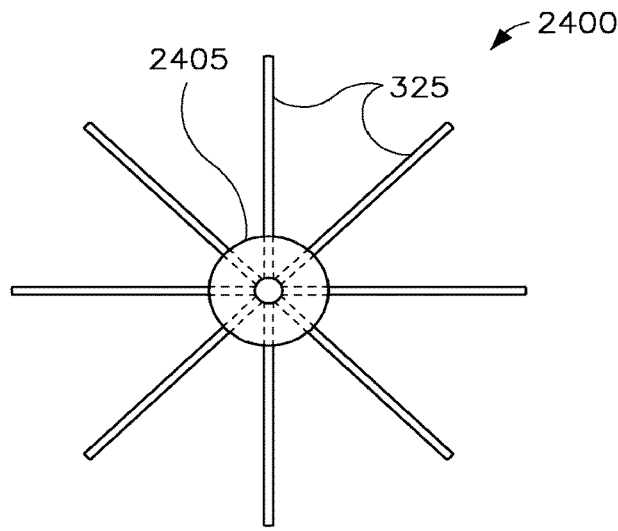
FIGS. 24A-24E are diagrams illustrating a tubing system going from an expanded state to a compressed state according to exemplary embodiments of the invention.
Figure 24B:
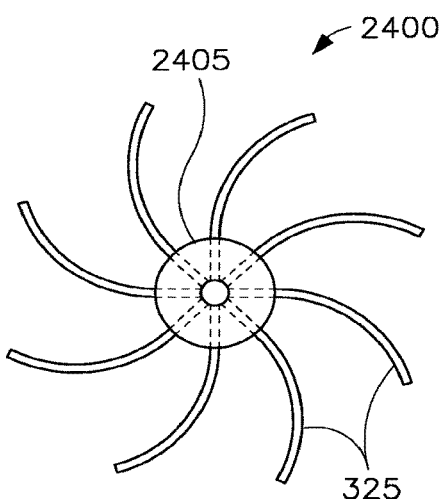

Next, in FIG. 24B, the tubing 325 has been illustrated with curves because the tubing system 2400 has been rotated about a central geometrical axis in order to contract the tubing 325 towards the central geometrical axis. Specifically, the disc 2405 has been rotated in a counter clockwise fashion so that the tubes 325 are drawn closer relative to the disc 2405. This can be accomplished through a crank mechanism (not illustrated).

Figure 24C:
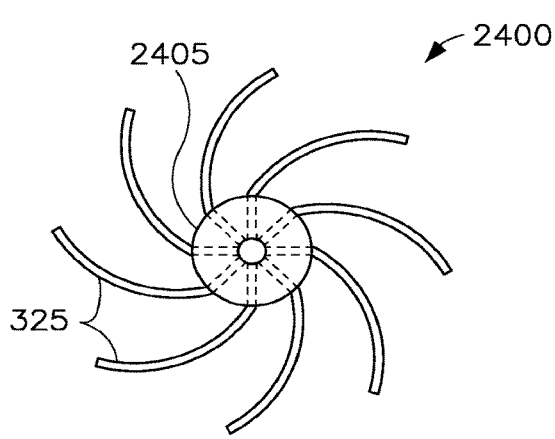
Figure 24D:
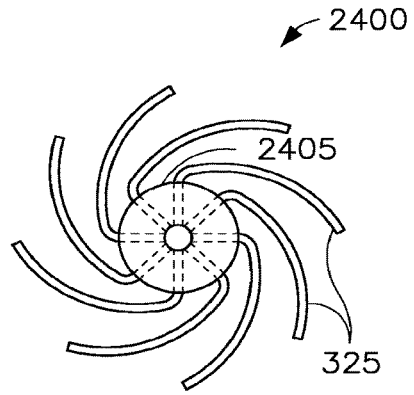

FIGS. 24C and 24D illustrate further rotation of the central disc 2405 so that the tubes 325 are drawn closer towards the central disc 2405. The tubes 325 may be attached to tissue 10 surrounding a wound 6, so that the tubes 225 can grasp the tissue 10 and draw it closer to the central disc 2405 as the central disc 2405 is rotated. Additionally, the dressing is drawn into the middle allowing the skin to granulate in from the periphery. The dressing does not prevent peripheral secondary healing by retracting.

Figure 24E:
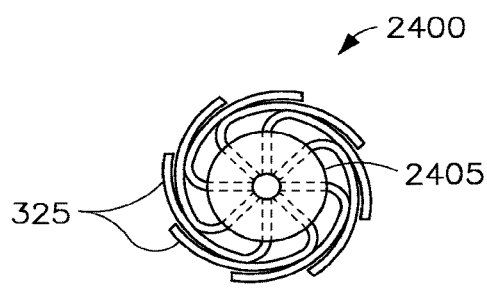

FIG. 24E illustrates further contraction of the tubing 325 relative to the central disc 2405 after the central disc 2405 has been rotated. The central disc 2405 may be rotated over a predetermined time schedule, such as on the order of days, such that the tissue 10 surrounding a wound 6 (not illustrated in FIG. 24) may be pulled in closer while the tubing 325 is contracted towards the central disk 2405 over time.

Figure 25A:
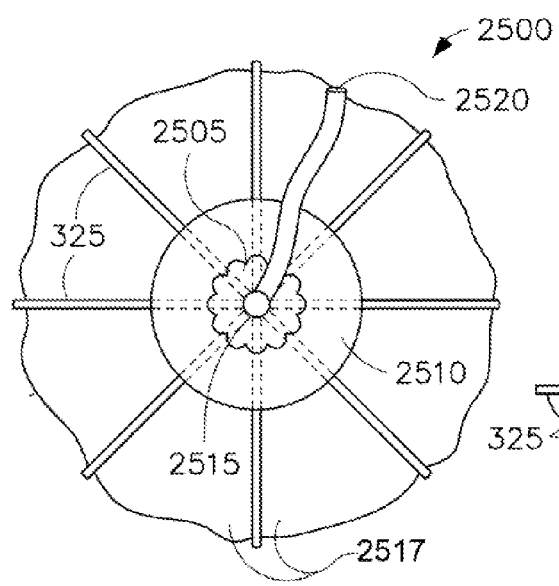
FIGS. 25A-25B are diagrams illustrating a tubing system with a tension device according to one exemplary embodiments of the invention.
Figure 25B:
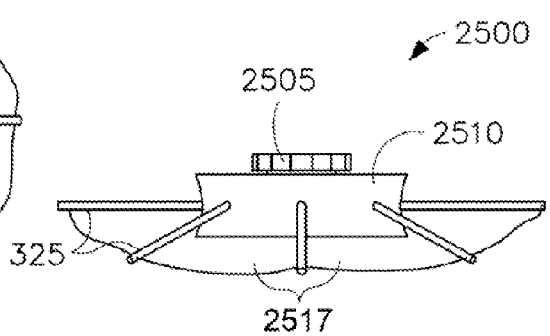

FIGS. 25A-25B are diagrams illustrating a tubing system 2500 with a tension device 2505 according to one exemplary embodiments of the invention. The materials and parts of the tubing system 2500 may be similar to those of the tubing system 2400 illustrated in FIG. 24. Therefore, only the differences between these figures will be described below.

According to this exemplary embodiment, the tubing system 2400 may comprise an integral central housing 2510 that receives each of the tubes 325. The central housing 2510 may direct each of the tubes 325 to a central channel 2515 that is coupled to a feeding or exit tube 2520. The feeding or exit tube 2520 may have a diameter that is larger than the diameters of the tubes 325. Each of the tubes 325 may comprise apertures or holes 2205 but are not illustrated in this figure. A film 2517 may be provided between the tubes 325 to allow for an airtight seal. The film may be made from made from a range of polymers, like the tubes 325, and may include, but is not limited to silicone rubber latex and thermoplastic elastomers. Other materials may include, but are not limited to, plastic and hard rubbers, or a combination thereof.

Positioned on one side of the central housing 2510 can be a tensioning device 2505. The tensioning device 2505 may comprise a knob or gear that can be rotated in order to rotate the central housing 2510. As discussed above in connection with FIG. 24, rotation of the central housing 2510 and the corresponding tubing 325 causes the corresponding tubing to contract and move towards the central housing 2510. Any tissue 10 (not illustrated) coupled to the ends of the tubing 325 may be pulled towards the central housing 2510 so that a wound 6 (not illustrated) may be closed or covered more by the tissue 10.

Figure 26:
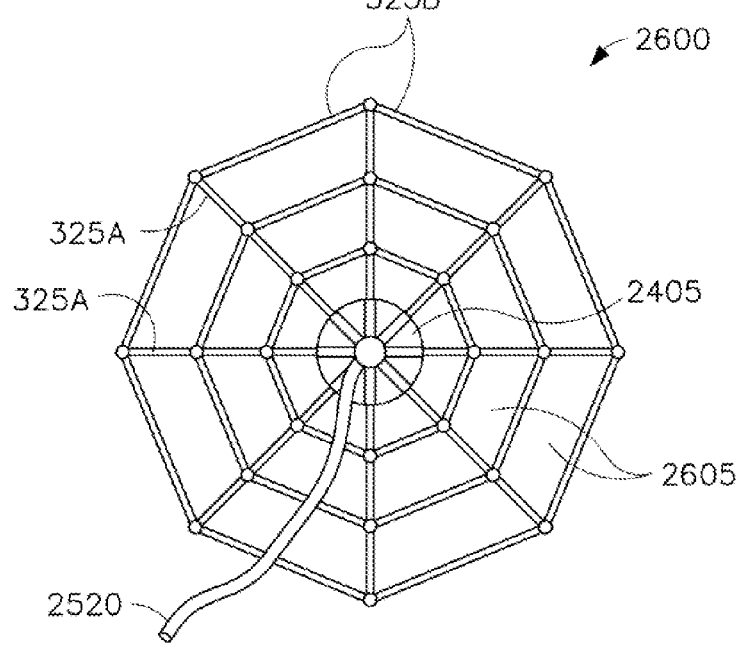
FIG. 26 is a diagram illustrating a web-like tubing system according to one exemplary embodiment of the invention.

FIG. 26 is a diagram illustrating a web-like tubing system 2600 according to one exemplary embodiment of the invention. The materials and parts of the tubing system 2600 may be similar to those of the tubing systems 2400 and 2500 illustrated in FIGS. 24-25. Therefore, only the differences between these figures will be described below.

According to this exemplary embodiment, the web-like tubing system 2600 may further comprise a planar material 2605 that is positioned between each of the first tubes 325A that extend from the central disc 2405 in a radial manner. This planar material 2605 may comprise materials similar to those from which the tubes 325 are made. The planar material 2605 may have a thickness which is typically less than a diameter of the tubes 325. The planar material 2605 may be designed to form an air-tight seal over a wound 6 (not illustrated) when the web-like tubing system 2600 is positioned on top of the wound 6. This film would be significantly pliable and thin to allow the system to collapse on itself and allow for wound contraction.

Also in this exemplary embodiment, each of the first tubes 325A extending from the central disc 2405 in a radial manner may have second tubes 325B that extend in circumferential direction relative to the central disc 2405 and which connect each first tube 325A to a corresponding neighboring first tube 325A. Each of the tubes 325, including the first and second tubes 325A, B, may comprise apertures or holes 2205 but are not illustrated in this figure for simplicity. The web-like tubing system 2600 may be trimmed with scissors to an appropriate size depending upon a particular size of a wound 6 (not illustrated).

Figure 27:
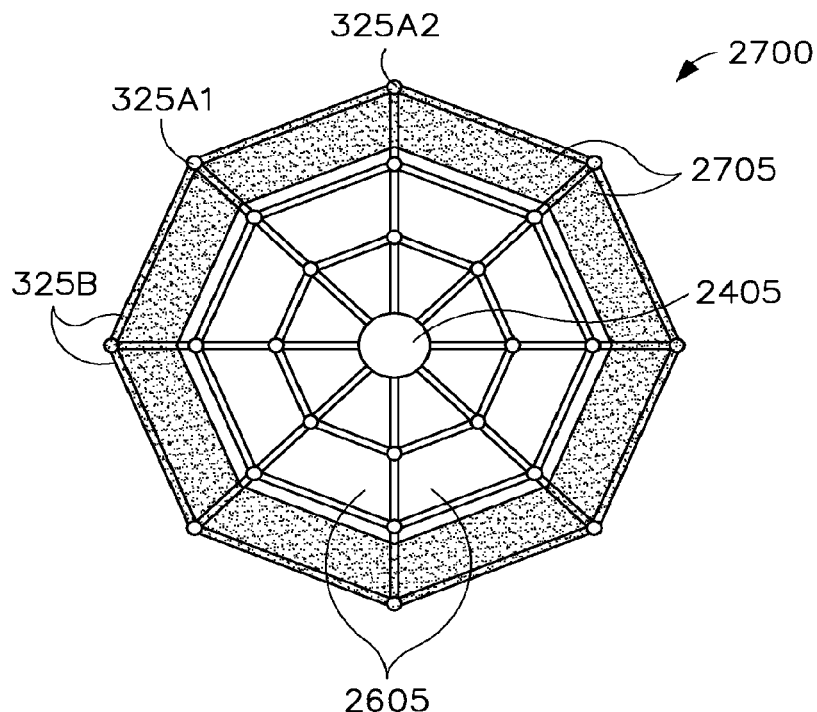
FIG. 27 is a diagram illustrating another web-like tubing system according to one exemplary embodiment of the invention.

FIG. 27 is a diagram illustrating another web-like tubing system 2700 according to one exemplary embodiment of the invention. The materials and parts of the tubing system 2700 may be similar to those of the tubing system 2600 illustrated in FIG. 26. Therefore, only the differences between these figures will be described below.

According to this exemplary embodiment, the web-like tubing system 2700 may comprise planar materials 2705 that have an adhesive so that the planar material 2705 will adhere to wounded tissue 10. The planar material 2705 having the adhesive may be positioned around a perimeter of the web-like tubing system 2700 in order to form an air-tight seal over a wound 6 (not illustrated). The adhesive could be on either the side of the skin/wound as well as on the side opposite the skin/wound. The adhesive on the skin side would assist in forming an airtight seal on the skin and assist in tensioning. The adhesive on the reverse side would assist in adhesion of a thin plastic film for creation of an airtight seal.

Similar to the other exemplary embodiments described above, each of the first and second tubes 325A, 325B may be attached to edges of tissue 10 that surround a wound 6 with fastening mechanisms 615 (not illustrated) that may comprise staples were suture threads. Each of the tubes 325, including the first and second tubes 325A, B, may comprise apertures or holes 2205 but are not illustrated in this figure for simplicity. The web-like tubing system 2700 may be trimmed with scissors to an appropriate size depending upon a particular size of a wound 6 (not illustrated).

Figure 28A:
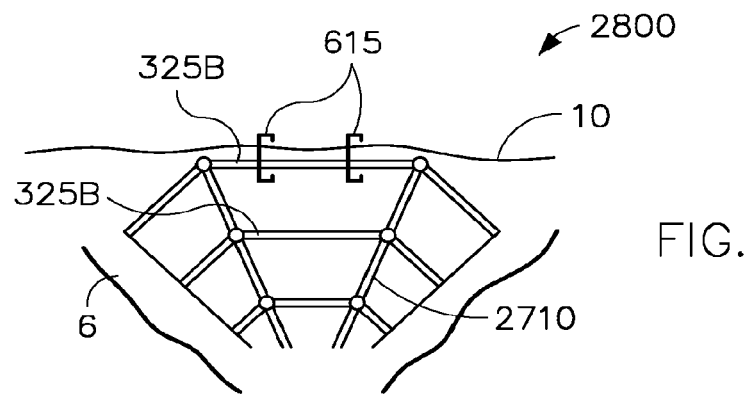
FIGS. 28A-28B are diagrams illustrating applications of a web-like tubing system with a adhesive perimeter to facilitate an airtight seal on the skin and prevent the need to put an airtight seal over the entire dressing (only a peripheral boarder is required) according to exemplary embodiments of the invention.
Figure 28B:
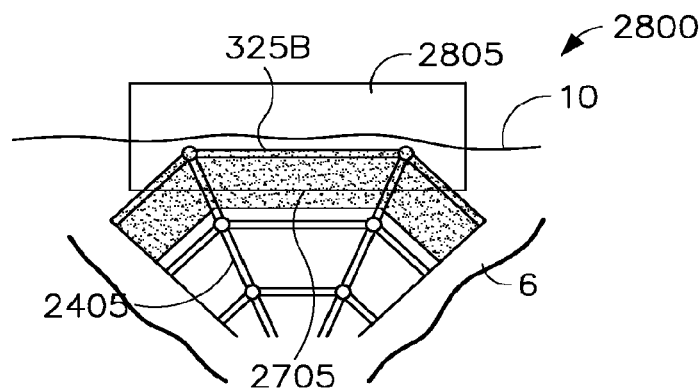

FIGS. 28A-28B are diagrams illustrating applications of a web-like tubing system 2800 with an adhesive perimeter to facilitate an airtight seal on the skin and prevent the need to put an airtight seal over the entire dressing (only a peripheral boarder is required) according to exemplary embodiments of the invention. The materials and parts of the tubing system 2800 may be similar to those of the tubing system 2700 illustrated in FIG. 27. Therefore, only the differences between these figures will be described below.

Similar to the other exemplary embodiments described above, each of the first and second tubes 325A, 325B may be attached to edges of tissue 10 that surround a wound 6 with fastening mechanisms 615 (not illustrated) that may comprise staples or suture threads. Each of the tubes 325, including the first and second tubes 325A, B, may comprise apertures or holes 2205 but are not illustrated in this figure for simplicity. The web-like tubing system 2800 may be trimmed with scissors to an appropriate size depending upon a particular size of a wound 6 (not illustrated).

According to the exemplary embodiment illustrated in FIG. 28A, the second tubes 325B of the system 2800 may be attached to tissue 10 with fastening mechanisms 615 that may comprise staples. In the exemplary embodiment illustrated in FIG. 28A, the wound 6 may have a conical shape and the tubing system 2800 may be shaped appropriately so that it mirrors the shape of the wound 6.

According to the exemplary embodiment illustrated in FIG. 28A, the web-like tubing system 2800 may comprise planar adhesive materials 2705. A separate planar sheet 2805 of another adhesive may be used in combination with the planar adhesive material 2705 in order to fasten or secure the web-like tubing system 2000 to the wound 6 and surrounding tissue 10. Similar to FIG. 28A, the wound 6 of FIG. 28B comprises a conical shape that has depth.

In each of the tubing systems 2400, 2500, 2600, 2700, and 2800, the geometric central region of the tubing systems can be rotated in order to contract the first tubes 325 extending in the radial directions. This contraction of the first tubes 325A may further close a wound 6 when the tubes 325A, 325B are attached to tissue 10 surrounding the wound 6.

In FIG. 28B, the illustration depicts a peripheral strip of adhesive film 2805 is placed only on the periphery of the dressing as appose to the entire dressing. The application of the adhesive film 2805 will create an airtight system despite not covering the entire dressing since the dressing will be airtight by design. This design may limit air leaks and loss of negative pressure since the only location of leaks can occur at the skin-dressing margin. Additionally, adhesive around the periphery of the dressing will facilitate the adhesion between the adhesive film and the dressing itself.

FIGS. 29A-29F are diagrams illustrating a tissue filler system 2900 and its relative movement according to exemplary embodiments of the invention. According to the exemplary embodiment illustrated in FIG. 29A, the tissue filler system 2900 may comprise a first small tube ring 325A2 and a second larger tube ring 325A1. The first small tube ring 325A2 may be coupled to an exit or distribution tube 325A3. The exit or distribution tube 325A3 may be coupled to a pump 340 (not illustrated) which may create a vacuum or which may distribute fluid. The first small tube ring 325A2 and second large ring tube 325A2 may have diameters of approximately 3 mm or less. However, one of ordinary skill the art recognizes that other diameters are included within the scope of the invention.

Since wounds can often be coupled with soft tissue loss as well as skin, the tissue filler system 2900 may be positioned in voids or defects in soft tissue 10. The tissue filler system 2900 may be used for deep wounds 6 requiring deep wound care. The tissue filler system 2900 comprises a three-dimensional vacuum structure that can assist with reducing or eliminating infection in deep wounds 6 by removing fluids from the wounds 6. One treatment goal for deep wounds or sinuses is to allow the wound to heal from the deep to superficial level by preventing the wound from closing at the superficial area first creating a closed space for abscess development.

In a fluid distribution context, fluid would enter the distribution tube 325A3 and then the fluid would proceed to the second smaller ring tube 325A2. From the second smaller ring tube 325A2, the fluid would be disbursed among the longitudinal tubes 325. The fluid then would flow through each of the longitudinal tubes 325 and an exit through the apertures 2205 present in each longitudinal tube 325. According to one exemplary embodiment, the longitudinal tubes 325 may be coupled together by transverse tubes 325B1 which may have holes or apertures similar to the longitudinal tubes 325. The transverse tubes 325B1 may be made from the same materials as the longitudinal tubes 325 oriented at approximately ninety degrees relative to the transverse tubes 325B1.

In the vacuum context, the flow of the fluid described above would be in reverse in which fluid would enter each of the apertures 2205 and then flow towards the exit tube 325A3. The longitudinal tubes 325 may have diameters of approximately 1 mm or less. However, one of ordinary skill the art recognizes that other diameters are included within the scope of the invention.

A plurality of longitudinal tubes 325 are connected between the first small ring tube 325A2 and the larger ring tube 325A1. Each of the longitudinal tubes 325 may further comprise apertures 2205 and channels 2215 (not illustrated), similar to the embodiment described above in connection with FIG. 22A. In the exemplary embodiment illustrated in FIG. 29A, the tissue filler system 2900 is any mid-or halfway expandable state as dictated by the position of the second larger ring tube 325A1.

As noted previously, tubing 325 can be made from a range of polymers, and may include, but is not limited to silicone rubber latex and thermoplastic elastomers. Silicone may be one of the most common choices because it is inert and unreactive to body fluids and a range of medical fluids with which it might come into contact. Other materials may include, but are not limited to, plastic and hard rubbers, or a combination thereof.

Figure 29A:
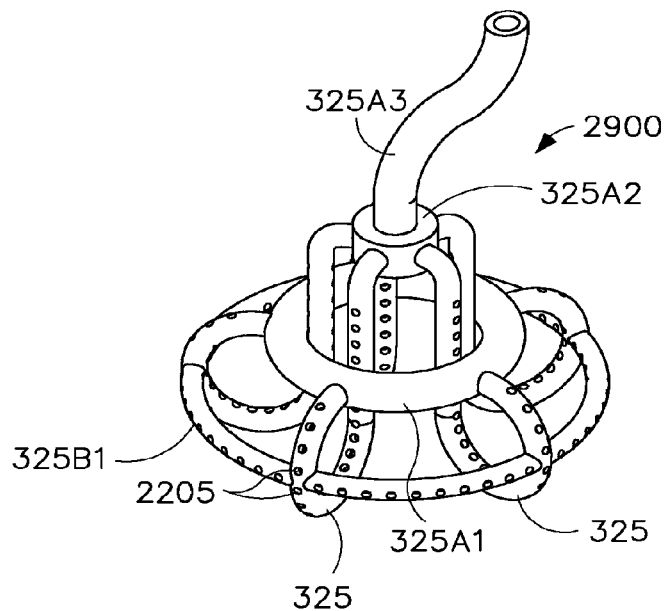
FIGS. 29A-29F are diagrams illustrating a tissue filler system and its relative movement according to exemplary embodiments of the invention.
Figure 29B:
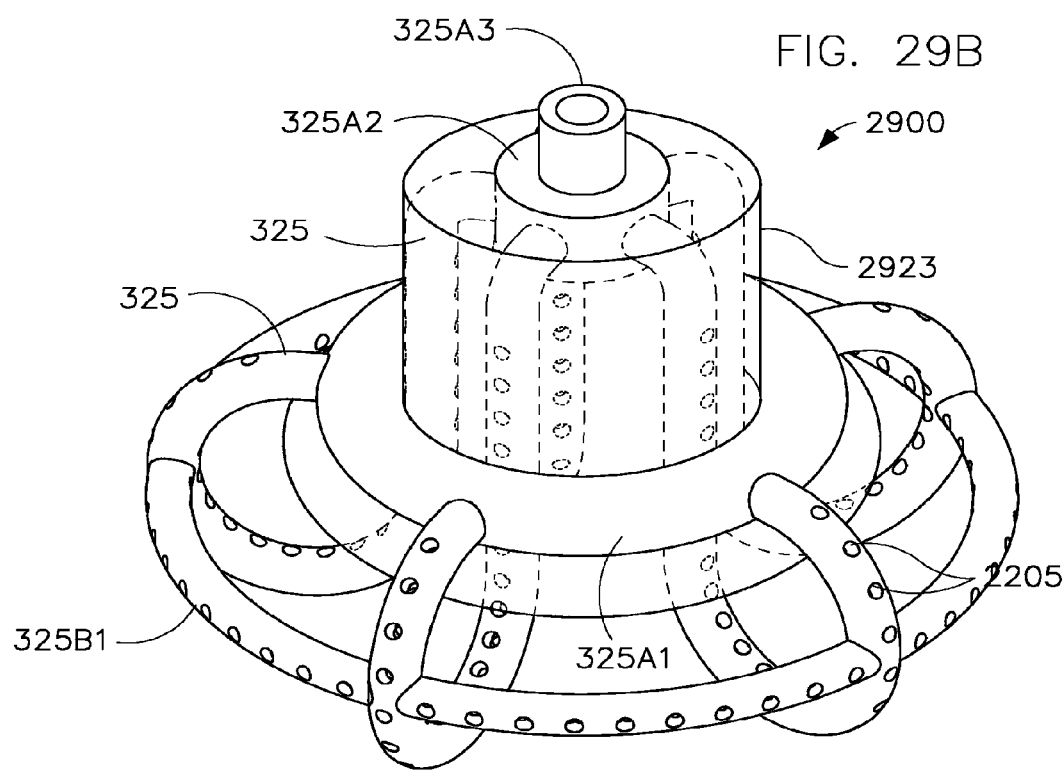

In the exemplary embodiment illustrated in FIG. 29B, the tissue filler system 2900 is illustrated with an increased magnification view to show more detail of the system 2900. The longitudinal tubes 325 may be coupled to the first small ring tube 325A2 and second large ring tube 325A1 using adhesives or plastic welds. Between the longitudinal tubes 325, transverse tubes 325B1 may be provided. The first small ring tube 325A2 and second large ring tube 325A1 in addition to the longitudinal tubes 325 may be formed by a single mold in order to form an integral structure without any discontinuities or separations that require coupling mechanisms.

Figure 29C:
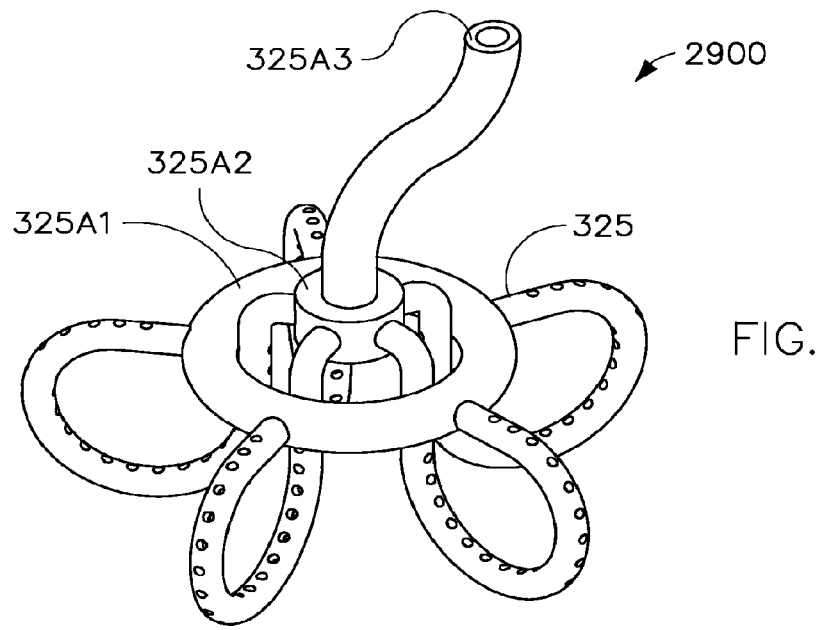

In the exemplary embodiment illustrated in FIG. 29C, the second larger ring tube 325A1 has been positioned closer to the first small ring tube 325A2 which causes the longitudinal tubes 325 to expand in a radial fashion relative to the ring tubes 325A1, 325A2. Further, the transverse tubes 325B1 illustrated in FIGS. 29A-B have been removed. The transverse tubes 325B1 have been removed from this FIG. 29C as well as the remaining FIGS. 29D-F. However, the transverse tubes 325B1 may be added to these embodiments without departing from the invention.

Figure 29D:
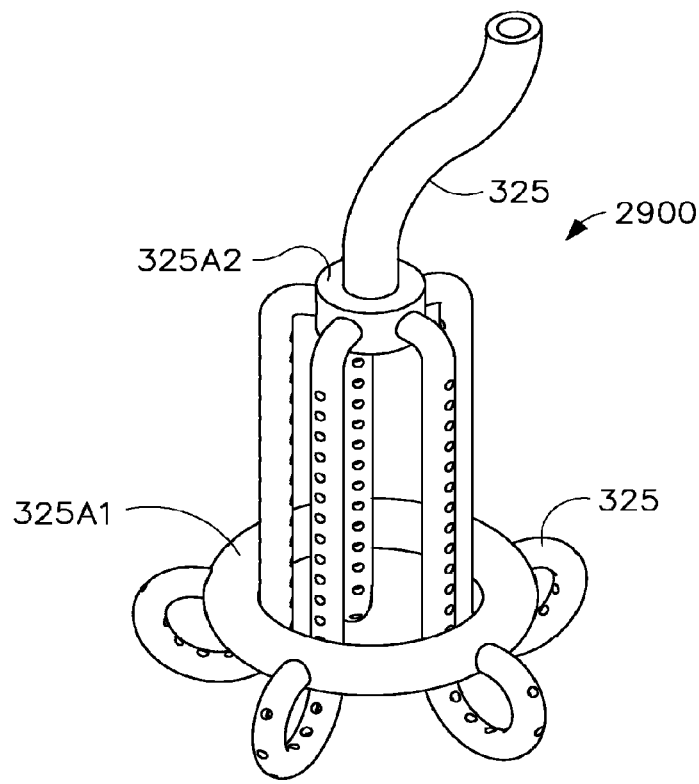

As illustrated in FIG. 29D, the second larger ring tube 325A1 has been displaced or moved apart relative to the first ring tube 325A2. This relative movement of the first and second ring tubes 325A1, A2 as illustrated in FIGS. 29C-D causes the longitudinal tubes 325 to contract relative to their previous position as illustrated in FIG. 29C. This second larger ring tube 325A1 can be incrementally moved relative to these first small ring tube 325A2 so that the displacement or contraction of the longitudinal tubes 325 is relatively small over the course of time which would allow for the closing of healthy tissue 10 surrounding a wound 6.

A pliable and airtight material 2923 (that may be transparent in some exemplary embodiments) may be draped between the two rings 325A1 and 325A2. By allowing this material 2923 to be pliable it will allow for the tensioning or retraction of the loops while maintaining an airtight system. Additionally, as described above an airtight seal between the peripheral skin edge and the dressing (the larger ring) would be obtained through thin adhesive strips.

Figure 29E:
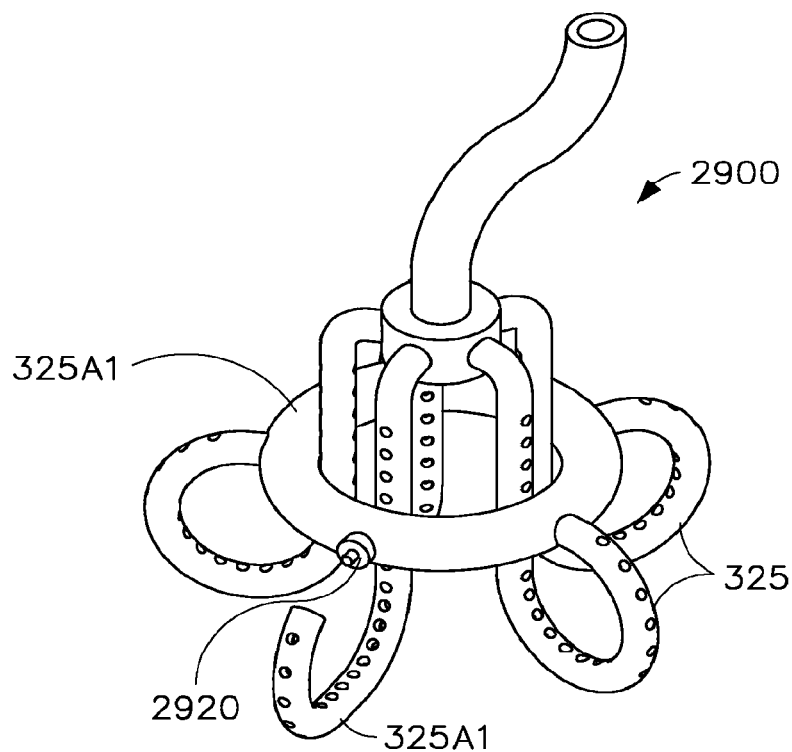
Figure 29F:
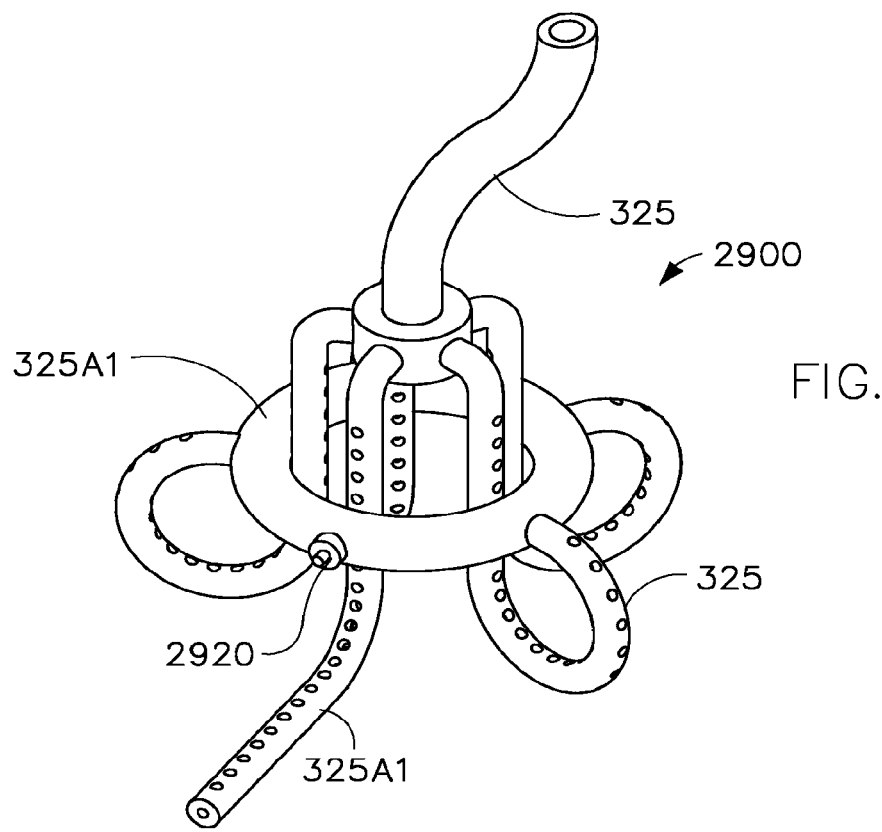

In the exemplary embodiment of the tissue filler system 2900 of FIG. 29E, a coupling mechanism 2920 positioned on the second larger ring tube 325A1 is illustrated. The coupling mechanism 2920 may comprise a valve that mates with a cylindrical end of one of the longitudinal tubes 325.

If a tubular void or sinus is present near a wound 6, then one or more of the longitudinal tubes 325 may be cut away from the second larger ring tube 325A1 such as illustrated in FIG. 29E. In the exemplary embodiment illustrated in FIG. 29E the longitudinal tube 325A4 has been cut so that it is removed from the second larger ring tube 325A1. In the exemplary embodiment illustrated in FIG. 29F, the cut longitudinal tube 325A4 can be moved into tubular voids or a sinus that may be present adjacent to a wound 6. Additionally, other common drains (such as, but not limited to, a JACKSON PRATT™ brand drain) that are available in the market today could be attached to the suction mechanism in order to allow for sinus management or multiple wounds.

For the dressing systems described above which may include a tensioning device 610, locking mechanisms may be employed to prevent loss of traction on the edges of tissue 10. According to some of the exemplary embodiments, traction or tensile forces may be applied to the central longitudinal member 625 allowing for the edges of tissue 10, such as skin, to be brought closer together and to compress a sponge 315. After 3 to 5 days, the sponge 315 may be removed and the edges of the tissue 10, such as skin, may be directly repaired without the need for skin grafts. With the exemplary embodiments described above, closure of wounds 6 may occur over a period of days to weeks while tensile forces are applied to a tensioning device 610. Alternatively, wound management that allows for partial wound closure but not complete closure will reduce the needs for large amounts of skin grafting or even free flaps.

According to one alternate exemplary embodiment (not illustrated), the Roman sandal chord 1215 may be embedded into a dressing system such as in a sponge 315. With such a system, the sponge 315 usually would not be trimmed or cut in order to prevent accidental cutting or damage to the Roman sandal cord 1215.

Certain steps in the processes or process flows described in this specification listed below and mentioned above naturally precede others for the invention to function as described. However, the invention is not limited to the order of the steps described if such order or sequence does not alter the functionality of the invention. That is, it is recognized that some steps may performed before, after, or parallel (substantially simultaneously with) other steps without departing from the scope and spirit of the invention. In some instances, certain steps may be omitted or not performed without departing from the invention. Further, words such as "thereafter", "then", "next", etc. are not intended to limit the order of the steps. These words are simply used to guide the reader through the description of the exemplary method.

Figure 30:
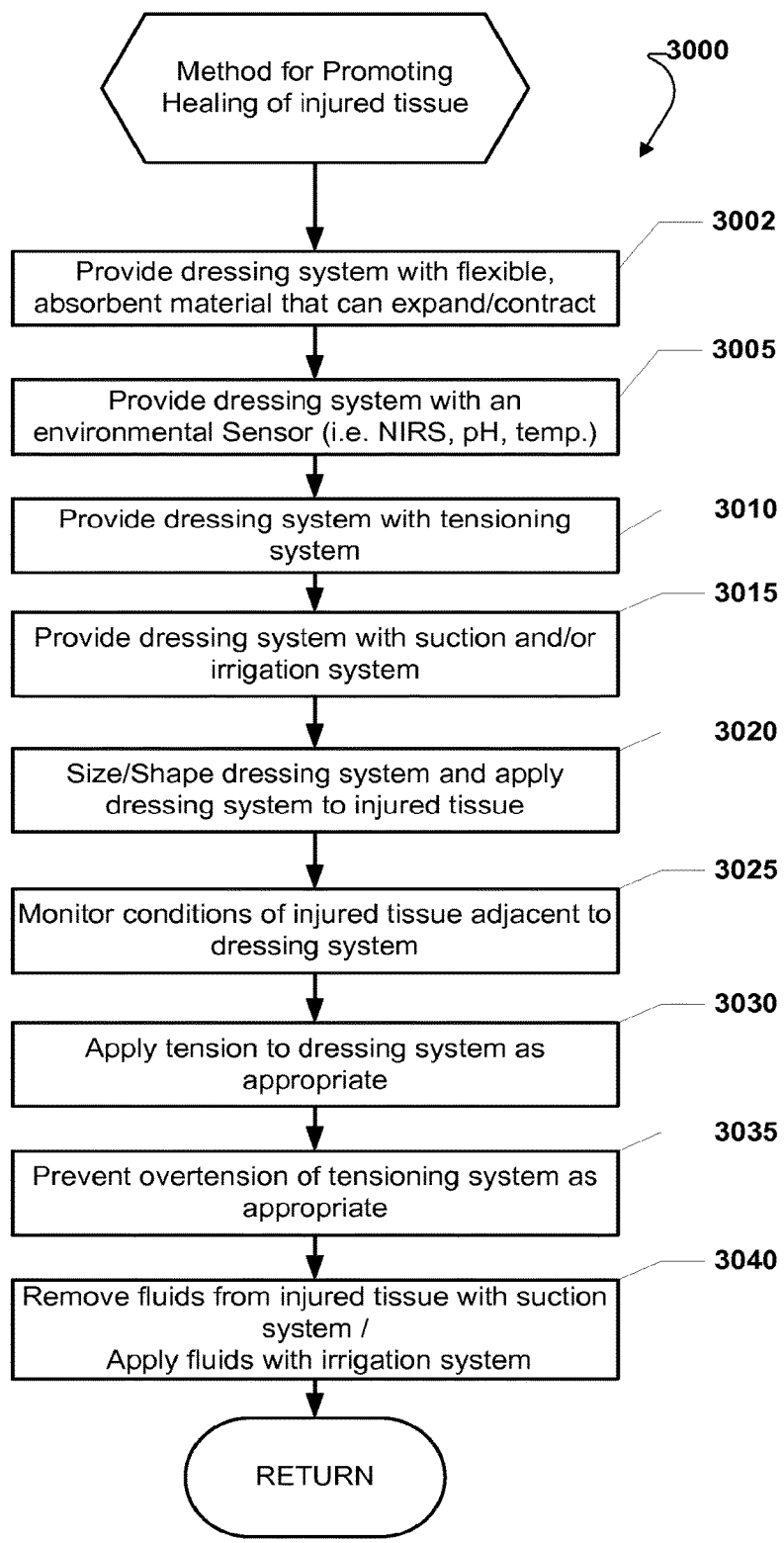
FIG. 30 is a flow chart illustrating some steps of an exemplary method for promoting healing of injured tissue according to one exemplary embodiment of the invention.

Referring now to FIG. 30, this figure is a flowchart illustrating a method 3000 for promoting the healing of injured tissue. Step 3002 is the first step of the method 3000 in which a dressing system may be provided with an absorbent material that may expand or contract for promoting healing of the injured tissue. The dressing system may comprise anyone of those illustrated in FIGS. 1-29 of this disclosure. The absorbent material may comprise a sponge, such as sponge 315 described above.

Next, in step 3005, the dressing system may be provided with an environmental sensor. The environmental sensor may comprise at least one of and/or a combination of a near infrared spectroscopy (NIRS), pH, temperature sensor, or any other similar sensors. As discussed above, a NIRS sensor may detect oxygenation levels adjacent to injured tissue. A pH sensor may detect acid levels near injured tissue while a temperature sensor may provide temperature readings adjacent to injured tissue. One or more computers may be coupled to these environmental sensors.

Subsequently, in step 3010, the dressing system may be provided with a tensioning system such as illustrated in FIGS. 2A-2B and FIG. 6. The tensioning system may apply tensile forces to the dressing system in order to close or move the injured tissue while it heals.

Next, in step 3015, the dressing system may be provided with a suction and/or irrigation system such as illustrated in FIGS. 3-5, 8, and 10-11. This means that the dressing system may be provided with a suction system that removes fluid from the injured tissue. Alternatively, or in combination with the suction system, the dressing system may be provided with a separate irrigation system that applies fluids, such as those containing antibiotics and other health promoting substances, to the injured tissue.

In step 3020, the dressing system may be sized and/or shaped and applied to the injured tissue. In this step, materials that form part of the dressing system, such as a sponge 315, may be cut or manufactured to an appropriate geometrical shape that matches the injured tissue. Alternatively, in this step, when the dressing system is being manufactured, it may be provided with a particular geometric shape to match a specific section of the human anatomy such as an arm, leg, or torso region, such as illustrated in FIG. 1.

In step 3025, one or more environmental conditions of the injured tissue adjacent to the dressing system may be monitored. For example, if a NIRS sensor is provided with the dressing system, then the oxygenation levels adjacent to the injured tissue may be monitored and recorded. Similarly, if a pH sensor or a temperature sensor is provided with the dressing system, then acid levels as well as temperature of the injured tissue may be monitored and recorded. In this step, computer implemented algorithms and software may be provided for operating and monitoring the environmental sensors for the automatic detection of change in various environmental conditions relative to the injured tissue.

In step 3030, tension may be applied to the dressing system as appropriate. This tension may be applied by a medical personnel as well as by a machine such as a motor that is under the control of a computer. In step 3035, over tensioning of the tensioning system may be prevented through mechanical devices and/or various sensors. These sensors may be coupled to a computer. The computer may provide feedback to a medical personnel when tension is applied by the medical personnel or by a machine, or a combination thereof. The computer may sound one or more various alarms if over tensioning is detected by the one or more tension sensors.

In step 3040, fluids adjacent to the dressing system and the injured tissue may be removed with a suction system. The suction system may comprise a vacuum producing device which produces negative pressure that draws fluid produced by injured tissue through one or more various tubes coupled to the dressing system. In step 3040, health promoting substances in the form of fluids may also be applied with an irrigation system coupled to the dressing system which provides liquid delivery of substances such as drugs, antibiotics, and other similar substances. The process then may return and continue with anyone of the aforementioned steps described above.

For any software described in the flow chart discussed above and in the computer-implemented embodiments illustrated in the various Figures of this disclosure, one of ordinary skill in programming is able to write computer code or identify appropriate hardware and/or circuits to implement the disclosed invention without difficulty based on the flow charts and associated description in this specification. Therefore, disclosure of a particular set of program code instructions or detailed hardware devices is not considered necessary for an adequate understanding of how to make and use the invention. The inventive functionality of the claimed computer implemented processes is explained in more detail in the above description and in conjunction with the Figures which may illustrate various process flows.

With respect to computer based systems described in connection with the dressing system described above, in one or more exemplary aspects, the functions described may be implemented in hardware, software, firmware, or any combination thereof. If implemented in software, the functions may be stored on or transmitted as one or more instructions or code on a computer-readable medium. Computer-readable media include both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Although selected aspects have been illustrated and described in detail, it will be understood that various substitutions and alterations may be made therein without departing from the spirit and scope of the present invention, as defined by the following claims.

What is claimed is:

1. A negative pressure wound therapy dressing system, comprising:
   a dressing including a lower layer of porous material to contact a wound and an upper layer of porous material oriented substantially parallel to the lower layer and a wound cover layer having an adhesive perimeter;
   a suction system connected to the dressing at a central region of the wound cover layer;
   a separate irrigation system comprising:
   a central tube connected to the dressing and extending through both the central region of the wound cover layer and a central region of the upper layer of porous material of the dressing; and
   a plurality of irrigation delivery tubes embedded within the dressing between the lower layer of porous material and the upper layer of porous material and extending laterally outward from the central tube in a plane that is substantially perpendicular to the central tube,
   wherein each of the irrigation delivery tubes comprises a plastic material configured to be trimmed contemporaneously with the dressing while the plurality of irrigation delivery tubes are embedded within the dressing,
   wherein each of the irrigation delivery tubes defines an upper tube surface and a lower tube surface with the lower layer of porous material positioned below the lower tube surface and the upper layer of porous material positioned above the upper tube surface, and
   wherein each of the irrigation delivery tubes is connected in fluid communication with the central tube so as to deliver an irrigation fluid from the central tube to at least one irrigation port of each respective irrigation tube and into the lower layer of porous material of the dressing.

2. The system of claim 1, wherein the central tube is positioned in a central location of the dressing and extends normal to a major surface of the dressing as the central tube extends through the wound cover layer and the upper layer of porous material, and wherein the central tube turns at an angle to extend substantially parallel to the major surface of the dressing as the central tube extends away from the dressing.

3. The system of claim 1, wherein said at least one irrigation port of each respective irrigation tube is positioned proximate to an outer periphery region of the lower layer of porous material of the dressing.

4. The system of claim 1, wherein each of the irrigation delivery tubes comprises multiple irrigation ports to deliver the irrigation fluid from the central tube.

5. The system of claim 1, further comprising an irrigation source in communication with the central tube, the irrigation source containing an irrigation fluid comprising a composition selected from a group consisting of antibiotics, enzymes, growth factors, pain medicine, and anesthetics.

6. The system of claim 5, further comprising a pump in fluid communication with the central tube to urge the irrigation fluid through the central tube to said at least one irrigation port of each respective irrigation tube.

7. The system of claim 1, wherein at least one of the lower layer of porous material and the upper layer of porous material comprises a sponge material.

8. The system of claim 1, wherein at least one of the central tube and the irrigation delivery tubes contains with a porous filler material.

9. The system of claim 1, further comprising a vacuum source connected to the suction system for removing exudate from the wound contacted by the lower layer of porous material.

10. The system of claim 1, wherein the lower layer of porous material is positioned below the irrigation port of each respective irrigation tube such that the irrigation delivery tubes lie in a non-wound-contacting layer that is spaced from the wound by the lower layer of porous material.

11. The system of claim 1, wherein each of the irrigation delivery tubes has an outer diameter and an inner diameter, wherein the upper tube surface is defined by an upper portion of the outer diameter and the lower tube surface is defined by a lower portion of the outer diameter.

12. The system of claim 1, wherein at least one of the central tube and the irrigation delivery tubes contains a porous filler material positioned inside the at least one of the central tube and the irrigation tubes.

13. The system of claim 12, wherein the porous filler material is sized and configured to allow fluid flow and to prevent or limit clogging and in-growth of soft tissue.

14. The system of claim 1, wherein the irrigation delivery tubes extend substantially radially outward from proximal ends to distal ends.

15. The system of claim 14, wherein the irrigation system further includes circumferentially extending irrigation delivery tubes connecting the radially extending irrigation delivery tubes.

16. The system of claim 14, wherein the irrigation system includes no circumferentially extending irrigation delivery tubes connecting the radially extending irrigation delivery tubes.

17. A negative pressure wound therapy dressing system, comprising:
   a dressing including a lower layer of porous material to contact a wound and an upper layer of porous material oriented substantially parallel to the lower layer and a wound cover layer having an adhesive perimeter;
   a suction system connected to the dressing at a central region of the wound cover layer;
   a separate irrigation system comprising:
   a central tube connected to the dressing and extending through both the central region of the wound cover layer and a central region of the upper layer of porous material of the dressing and
   a plurality of irrigation delivery tubes embedded within the dressing between the lower layer of porous material and the upper layer of porous material and extending laterally outward from the central tube in a plane that is substantially perpendicular to the central tube,
   wherein each of the irrigation delivery tubes defines an upper tube surface and a lower tube surface with the lower layer of porous material positioned below the lower tube surface and the upper layer of porous material positioned above the upper tube surface,
   wherein each of the irrigation delivery tubes is connected in fluid communication with the central tube so as to deliver an irrigation fluid from the central tube to at least one irrigation port to each respective irrigation tube and into the lower layer of porous material of the dressing,
   wherein the irrigation delivery tubes extend substantially radially outward form proximal ends to distal ends, and
   wherein the irrigation delivery tubes curve in a spiral circumferentially as the irrigation delivery tubes extend substantially radially outward.

18. The system of claim 17, wherein each of the irrigation delivery tubes comprises a plastic material configured to be trimmed contemporaneously with the dressing while the plurality of irrigation delivery tubes are embedded within the dressing.

19. A method of operating a negative pressure wound therapy dressing system comprising a dressing including a lower layer of porous material to contact a wound and an upper layer of porous material oriented substantially parallel to the lower layer and a wound cover layer having an adhesive perimeter; a suction system connected to the dressing at a central region of the wound cover layer; a separate irrigation system comprising: a central tube connected to the dressing and extending through both the central region of the wound cover layer and a central region of the upper layer of porous material of the dressing; and a plurality of irrigation delivery tubes embedded within the dressing between the lower layer of porous material and the upper layer of porous material and extending laterally outward from the central tube in a plane that is substantially perpendicular to the central tube, wherein each of the irrigation delivery tubes defines an upper tube surface and a lower tube surface with the lower layer of porous material positioned below the lower tube surface and the upper layer of porous material positioned above the upper tube surface, and wherein each of the irrigation delivery tubes is connected in fluid communication with the central tube so as to deliver an irrigation fluid from the central tube to at least one irrigation port of each respective irrigation tube and into the lower layer of porous material of the dressing, the method comprising:

trimming plastic material of the irrigation delivery tubes with the dressing while the plurality of irrigation delivery tubes are embedded within the dressing;

applying the trimmed dressing to a wound such that the lower layer of porous material contacts the wound;

covering the wound and the dressing to form an airtight seal over the wound via the wound cover layer having the adhesive perimeter;

irrigating the wound via the irrigation system including the trimmed irrigation delivery tubes; and suctioning the wound via the suction system to perform negative pressure wound therapy.

\* \* \* \* \*

UNITED STATES PATENT AND TRADEMARK OFFICE
CERTIFICATE OF CORRECTION

PATENT NO. : 10,149,930 B2
APPLICATION NO. : 13/867100
DATED : December 11, 2018
INVENTOR(S) : Michael Simms Shuler It is certified that error appears in the above-identified patent and that said Letters Patent is hereby corrected as shown below:

In the Specification

Column 1, Lines 8-9, delete "13/867,100, filed on Apr. 21, 2013," and insert -- 12/855,019 filed on Aug. 12, 2010, --;

In the Claims

Column 43, Line 54 (approx.), Claim 5, delete "an" and insert -- the --;

Column 43, Line 66 (approx.), Claim 8, delete "with a" and insert -- a --;

Column 44, Line 46, Claim 17, delete "dressing" and insert -- dressing; --;

Column 44, Line 60, Claim 17, delete "to" and insert -- of --;

Column 44, Line 64, Claim 17, delete "form" and insert -- from --.

Signed and Sealed this
Fifth Day of May, 2020

Andrei Iancu
*Director of the United States Patent and Trademark Office*